United States Patent [19]
Stomp et al.

[11] Patent Number: 6,040,498
[45] Date of Patent: Mar. 21, 2000

[54] GENETICALLY ENGINEERED DUCKWEED

[75] Inventors: Anne-Marie Stomp; Nirmala Rajbhandari, both of Raleigh, N.C.

[73] Assignee: North Caroline State University, Raleigh, N.C.

[21] Appl. No.: 09/132,536

[22] Filed: Aug. 11, 1998

Related U.S. Application Data

[60] Provisional application No. 60/055,474, Aug. 12, 1997.
[51] Int. Cl.$^7$ .............................. C12N 5/04; C12N 15/82; C12N 15/84; A01H 1/00
[52] U.S. Cl. ........................ 800/294; 435/419; 435/469; 435/69.4; 435/69.51; 435/69.6; 435/70.21; 800/295; 800/300
[58] Field of Search .............................. 435/69.1, 320.1, 435/410, 413, 418, 419, 430, 430.1, 469, 69.4, 69.51, 69.6, 70.21; 536/23.6, 23.51, 23.52; 800/278, 288, 294, 295, 298, 300

[56] References Cited

U.S. PATENT DOCUMENTS

| | | | |
|---|---|---|---|
| 4,693,976 | 9/1987 | Schilperoort et al. | 435/469 |
| 4,956,282 | 9/1990 | Goodman et al. | 435/69.51 |
| 5,102,796 | 4/1992 | Hall et al. | 435/468 |
| 5,149,645 | 9/1992 | Hoekema et al. | 435/468 |
| 5,501,967 | 3/1996 | Offringa et al. | 435/468 |
| 5,504,200 | 4/1996 | Hall et al. | 536/24.1 |
| 5,550,038 | 8/1996 | Goodman et al. | 435/70.1 |
| 5,550,318 | 8/1996 | Adams et al. | 800/278 |
| 5,591,605 | 1/1997 | Hall et al. | 435/70.1 |
| 5,591,616 | 1/1997 | Hiei et al. | 435/468 |
| 5,629,175 | 5/1997 | Goodman et al. | 435/69.1 |
| 5,641,664 | 6/1997 | D'Halluin et al. | 435/468 |
| 5,650,307 | 7/1997 | Sijmons et al. | 435/468 |
| 5,712,135 | 1/1998 | D'Halluin et al. | 435/468 |
| 5,716,802 | 2/1998 | Sijmons et al. | 435/69.1 |
| 5,723,755 | 3/1998 | Fortin | 800/278 |
| 5,731,719 | 3/1998 | Komari et al. | 435/468 |
| 5,792,935 | 8/1998 | Arntzen et al. | 800/294 |

FOREIGN PATENT DOCUMENTS

| | | | |
|---|---|---|---|
| WO 86/03776 | 7/1986 | WIPO | C12N 15/00 |
| WO 95/06722 | 3/1995 | WIPO | C12N 15/00 |
| WO 98/37212 | 8/1998 | WIPO | C12N 15/82 |

OTHER PUBLICATIONS

Viyayachandra et al, Plant Mol.Biol., vol. 29, pp. 125–133, 1995.
Hansen et al, Proc. Natl. Acad. Sci., USA, vol. 91, pp. 7603–7607, 1994.
Chang et al, Z. Pflanzenphysiol., vol. 89, pp. 91–94, 1978.
Hei et al, Plant J., vol. 6, pp. 271–282, 1994.
Sabelli et al, Meth. Plant Biochem., vol. 10, pp. 79–100, 1993.
Flavell, R.B., Proc. Natl. Acad. Sci., USA, vol. 91, pp. 3490–3496, 1994.
Gray et al, Proc. Natl. Acad. Sci., USA, vol. 80, pp. 5842–5846, 1983.
Ma et al, Science, vol. 268, pp. 716–719, 1995.
Hillman, W.S. and Culley, Jr., D.D.; The Uses of Duckweed, American Scientist, vol. 66, pp. 442–451.

PCT International Search Report, Oct. 30, 1998, PCT/US98/16683.
Smith, R.H. and Hood, EE; *Agrobacterium tumefaciens* Transformation of Monocotyledons, Crop Science 35:301–309 (1995).
Schäfer, W. et al.; T–DNA integration and expression in a monocot crop plant after induction of Agrobacterium, Nature, vol. 327, Jun. 11, 1987, pp. 529–532.
Boulton, M.I. et al.; Specificity of Agrobacterium–mediated delivery of maize streak virus DNA to members of the Gramineae, Plant Molecular Biology 12: 31–40 (1989).
Jach, G et al.; Enhanced quantitative resistance against fungal disease by combinatorial expression of different barley antifungal proteins in transgenic tobacco, Plant Journal (1995) 8(1), 97–109.
Komari, T. et al.; Vectors carrying two separate T–DNAs for co–transformation of higher plants mediated by *Agrobacterium tumefaciens* and segregation of transformants free from selection markers, The Plant Journal (1996) 10(1), 165–174.
Jones, J.T. et al.; Isolation and characterization of a putative collagen gene from the potato cyst nematode *Globodera pallida*, Parasitology, 1996, vol. 113, pp. 581–588.
Hoever, M. et al.; Overexpression of wild–type p53 interferes with normal development in *Zenopus laevis* embryos, Oncogene (1994), 9, 109–120.
Bates, G.W.; Electroporation of Plant Protoplasts and Tissues, Methods in Cell Biology, vol. 50, 1995, pp. 363–373.
Okubara, P.A. et al.; Analysis of Genes Negatively Regulated by Phytochrome Action in *Lemna gibba* and Identification of a Promoter Region Required for Phytochrome Responsiveness, Plant Physical (1993) 101: 915–924.
Moon, H.K. and Stomp, A.M.; Effects of Medium Components and Light on Callus Induction, Growth, and Frond Regeneration in *Lemna Gibba* (Duckweed), In Vitro Cell Dev. Biol–Plant. 33:20–25, Jan. 1997.
Slovin, J.P. and Cohen, J.D.; Levels of Indole–3–Acetic Acid in *Lemna gibba* G–3 and in a Large Lemna Mutant Regenerated from Tissue Culture, Plant Physical (1988) 86: 522–526.
Sanford, J.C. et al.; Optimizing the Biolistic Process for Different Biological Applications, Methods iin Enzymology, vol. 217, 1993, pp. 483–509.
Rolfe et al.; Deletion Analysis of a Phytochrome–regulated Monocot rbcS Promoter in a Transient Assay System; Proc. Nat'l. Acad. Sci. USA, 88 (Apr. 1991), pp. 2683–2686.

*Primary Examiner*—Gary Benzion
*Assistant Examiner*—Ashwin D. Mehta
*Attorney, Agent, or Firm*—Myers Bigel Sibley & Sajovec, P.A.

[57] ABSTRACT

Methods and compositions for the efficient transformation of duckweed are provided. Preferably, the methods involve transformation by either ballistic bombardment or Agrobacterium. In this manner, any gene or nucleic acid of interest can be introduced and expressed in duckweed plants. Transformed duckweed plants, cells, tissues are also provided. Transformed duckweed plant tissue culture and methods of producing recombinant proteins and peptides from transformed duckweed plants are also disclosed.

65 Claims, 1 Drawing Sheet

GENETICALLY ENGINEERED DUCKWEED

RELATED APPLICATION INFORMATION

This application claims the benefit of United States Provisional Application No. 60/055,474 filed Aug. 12, 1997, which is incorporated by reference herein in its entirety.

This invention was made with Government support under grant number R823570-01-1 from the United States Environmental Protection Agency. The government has certain rights in this invention.

FIELD OF THE INVENTION

The present invention relates to methods and compositions for the transformation of duckweed, particularly to methods for transformation utilizing ballistic bombardment and Agrobacterium.

BACKGROUND OF THE INVENTION

The duckweeds are the sole members of the monocotyledonous family, Lemnaceae. The four genera and 34 species are all small, free-floating, fresh-water plants whose geographical range spans the entire globe. Landolt, *Biosystematic Investigation on the Family of Duckweeds: The family of Lemnaceae—A Monograph Study.* Geobatanischen Institut ETH, Stiftung Rubel, Zurich (1986). Although the most morphologically reduced plants known, most duckweed species have all the tissues and organs of much larger plants, including roots, stems, flowers, seeds and fronds. Duckweed species have been studied extensively and a substantial literature exists detailing their ecology, systematics, life-cycle, metabolism, disease and pest susceptibility, their reproductive biology, genetic structure, and cell biology. Hillman, *Bot. Review* 27, 221 (1961); Landolt, *Biosystematic Investigation on the Family of Duckweeds: The family of Lemnaceae—A Monograph Study.* Geobatanischen Institut ETH, Stiftung Rubel, Zurich (1986).

The growth habit of the duckweeds is ideal for microbial culturing methods. The plant rapidly proliferates through vegetative budding of new fronds, in a macroscopic manner analogous to asexual propagation in yeast. Duckweed proliferates by vegetative budding from meristematic cells. The meristematic region is small and is found on the ventral surface of the frond. Meristematic cells lie in two pockets, one on each side of the frond midvein. The small midvein region is also the site from which the root originates and the stem arises that connects each frond to its mother frond. The meristematic pocket is protected by a tissue flap. Fronds bud alternately from these pockets. Doubling times vary by species and are as short as 20–24 hours. Landolt, *Ber. Schweiz. Bot. Ges.* 67, 271 (1957); Chang et al., *Bull. Inst. Chem. Acad. Sin.* 24, 19 (1977); Datko and Mudd., *Plant Physiol.* 65,16 (1980); Venkataraman et al., *Z. Pflanzenphysiol.* 62, 316 (1970).

Intensive culture of duckweed results in the highest rates of biomass accumulation per unit time (Landolt and Kandeler, *The family of Lemnaceae—A Monographic Study. Vol.2: Phytochemistry, Physiology, Application, Bibliography,* Veroffentlichungen des Geobotanischen Institutes ETH, Stiftung Rubel, Zurich (1987)), with dry weight accumulation ranging from 6–10% of fresh weight (Tillberg et al., *Physiol. Plant.* 46, 5 (1979); Landolt, *Ber. Schweiz. Bot. Ges.* 67, 271 (1957); Stomp, unpublished data). Protein content of a number of duckweed species grown under varying conditions has been reported to range from 15–45% dry weight (Chang et al, *Bull. Inst. Chem. Acad. Sin.* 24, 19 (1977); Chang and Chui, *Z. Pflanzenphysiol.* 89, 91 (1978); Porath et al., *Aquatic Botany* 7, 272 (1979); Appenroth et al., *Biochem. Physiol. Pflanz.* 177, 251 (1982)). Using these values, the level of protein production per liter of medium in duckweed is on the same order of magnitude as yeast gene expression systems. Prior to now, the systematic optimization of medium components and culturing conditions for maximal growth and protein content for specific duckweed strains has not been done.

Sexual reproduction in duckweed is controlled by medium components and culturing conditions, including photoperiod and culture density. Flower induction is a routine laboratory procedure with some species. Plants normally self-pollinate and selfing can be accomplished in the laboratory by gently shaking cultures. By this method, inbred lines of *Lemna gibba* have been developed. Spontaneous mutations have been identified (Slovin and Cohen, *Plant Physiol.* 86, 522 (1988)), and chemical and gamma ray mutagenesis (using EMS or NMU) have been used to produce mutants with defined characteristics. Outcrossing of *L. gibba* is tedious but can be done by controlled, hand pollination. The genome size of the duckweeds varies from 0.25–1.63 pg DNA/2C with chromosome counts ranging from 20 to 80 and averaging about 40 across the Lemnaceae (Landolt, *Biosystematic Investigation on the Family of Duckweeds: The family of Lemnaceae—A Monograph Study.* Geobatanischen Institut ETH, Stiftung Rubel, Zurich (1986)). Ploidy levels are estimated to range from 2–12 C. Id. Genetic diversity within the Lemnaceae has been investigated using secondary products, isozymes, and DNA sequences. McClure and Alston, *Nature* 4916, 311 (1964); McClure and Alston, *Amer. J. Bot.* 53, 849 (1966); Vasseur et al., *Pl. Syst. Evol.* 177, 139 (1991); Crawford and Landolt, *Syst. Bot.* 10, 389 (1993).

Accordingly, the characteristics described above make duckweed an ideal choice to develop as an efficient, plant-based, gene expression system.

SUMMARY OF THE INVENTION

The present invention is drawn to methods and compositions for the efficient transformation of duckweed. The methods involve the use of ballistic bombardment, Agrobacterium, or electroporation to stably introduce and express a nucleotide sequence of interest in transformed duckweed plants. In this manner, any gene(s) or nucleic acid(s) of interest can be introduced into the duckweed plant. Transformed duckweed cells, tissues, plants and seed are also provided.

As a first aspect, the present invention provides a method for transforming duckweed with a nucleotide sequence of interest, wherein said nucleotide sequence comprises at least an expression cassette containing a gene which confers resistance to a selection agent, the method comprising the steps of: (a) providing a duckweed tissue target, the cells of the duckweed tissue including cell walls; and (b) propelling the nucleotide sequence at the duckweed tissue target at a velocity sufficient to pierce the cell walls and deposit the nucleotide sequence within a cell of the tissue to thereby produce a transformed tissue, wherein the nucleotide sequence is carried by a microprojectile; and wherein the nucleotide sequence is propelled at the tissue by propelling the microprojectile at the tissue.

As a second aspect, the present invention provides a method for transforming duckweed with a nucleotide sequence of interest, the method comprising the steps of: (a) inoculating a duckweed plant tissue with an Agrobacterium comprising a vector which comprises the nucleotide sequence, wherein the nucleotide sequence comprises at least an expression cassette containing a gene which confers resistance to a selection agent; and (b) co-cultivating the tissue with the Agrobacterium to produce transformed tissue.

As a third aspect, the present invention provides a method of transforming duckweed by electroporation.

As a fourth aspect, the present invention provides transformed duckweed plants and transformed duckweed tissue culture produced by the methods described above.

As a fifth aspect, the present invention provides a transformed duckweed plant and methods of using transformed duckweed plants to produce a recombinant protein or peptide.

Duckweed offers an ideal plant-based gene expression system. A duckweed gene expression system provides the pivotal technology that would be useful for a number of research and commercial applications. For plant molecular biology research as a whole, a differentiated plant system which can be manipulated with the laboratory convenience of yeast provides a very fast system in which to analyze the developmental and physiological roles of isolated genes. Model plants such as tobacco and Arabidopsis are currently used for this purpose by plant molecular biologists. These plants require greenhouse or field facilities for growth (often difficult for plant molecular biologists to obtain). Alternative gene expression systems are based on microbial or cell cultures where tissue and developmentally regulated gene expression effects are lost. Heterologous gene expression systems also require restructuring of the gene of interest prior to insertion, an expensive and time-consuming process. A duckweed system overcomes both of these problems and is far easier to grow and maintain in a laboratory setting. If it is desirable to harvest the expressed proteins or peptides (or molecules produced thereby), this can be accomplished by any suitable technique known in the art, such as mechanical grinding or lysing of cells.

For commercial production of valuable proteins, a duckweed-based system has a number of advantages over existing microbial or cell culture systems. In the area of mammalian protein production, plants show post-translational processing that is similar to mammalian cells, overcoming one major problem associated with microbial cell production of mammalian proteins. Duckweed is also far cheaper to produce than mammalian cell cultures. It has already been shown by others (Hiatt, *Nature* 334, 469 (1990)) that plant systems have the ability to assemble multi-subunit proteins, an ability often lacking in microbial systems. Plant production of therapeutic proteins also limits the risk from contaminating substances, including animal viruses, produced in mammalian cell cultures and in microbial systems. Contaminating substances are a major concern in therapeutic protein production. Unlike other suggested plant production systems, e.g., soybeans and tobacco, duckweed can be grown in fermentor/bioreactor vessels, making the system's integration into existing protein production industrial infrastructure far easier.

As a manufacturing platform for lower cost industrial enzymes and small molecules, duckweed offers the advantage that production is readily scaleable to almost any quantity because it can be grown under field conditions using nutrient-rich wastewater. A genetically engineered duckweed system growing on wastewater could produce a valuable product while simultaneously cleaning up wastewater for reuse. Such a system would turn a net capital loss (remediation of wastewater from discharge) into a chemical or enzyme production system with a positive economic balance. Duckweeds' advantage over chemical syntheses in field crops is that production does not require arable crop land or irrigation water necessary to increase food production for the world's increasing population.

These and other aspects of the present invention are disclosed in more detail in the description of the invention given below.

DETAILED DESCRIPTION OF THE INVENTION

Figure 1:
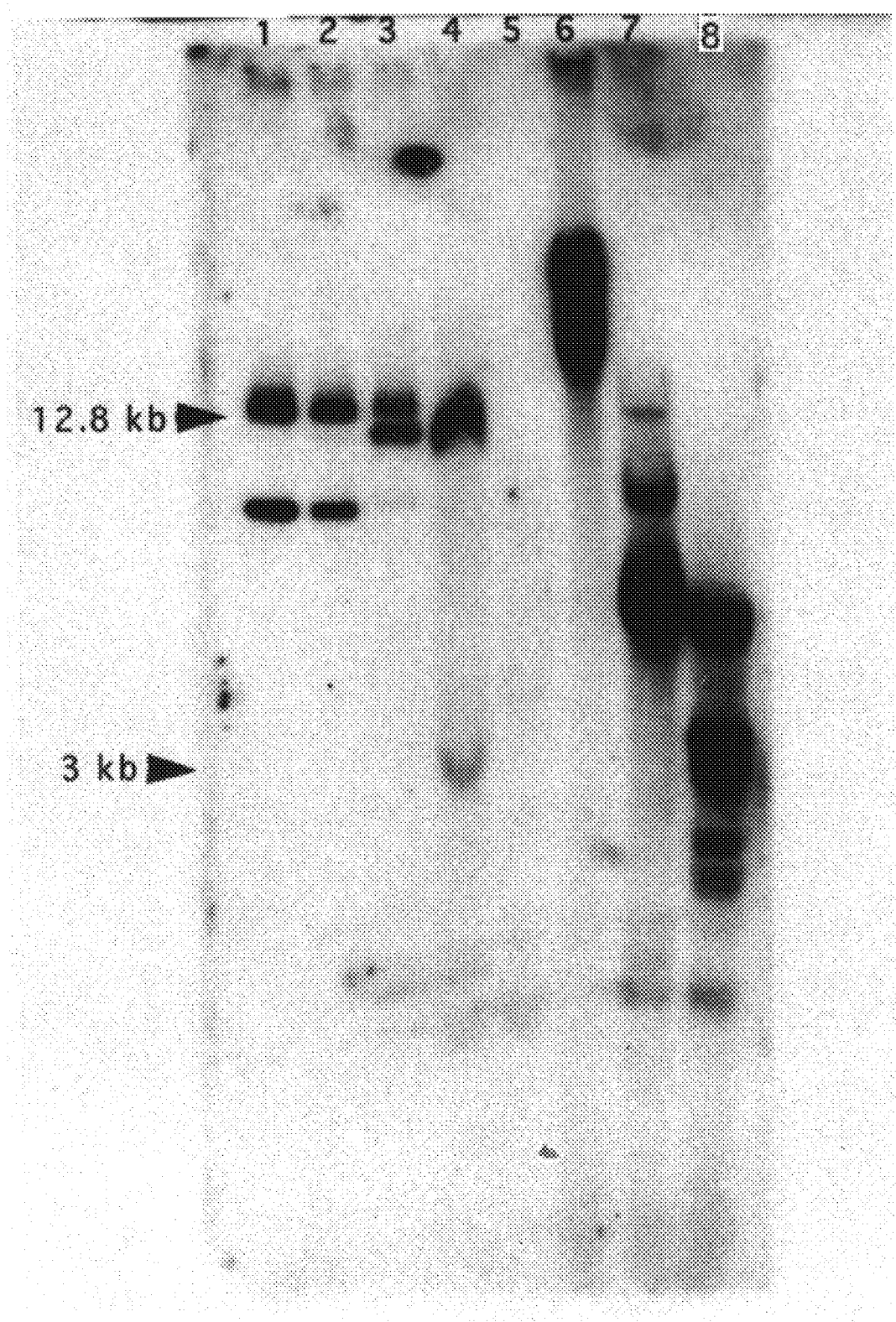
FIG. 1 presents an autoradiograph produced by Southern hybridization of untransformed duckweed DNA and transformed duckweed DNA from line D with a radioactively labeled 3.2 kb fragment from pBI121 containing the GUS gene. Channels: 1) Isolated, undigested pBI121 DNA. The expected major band is at 12.8 kb. The lower molecular weight band is probably represents the supercoiled plasmid. 2) HindIII digested, pBI121 DNA. This digestion linearizes the plasmid and shows the expected 12.8 kb band. The lower molecular weight band indicates incomplete digestion. 3) pBI121 DNA digested with both HindIII and EcoR1. Digestion was incomplete but yielded the expected bands: 12.8 kb (left from incomplete digestion), the approximately 9 kb band, and a faint supercoiled band. The 3.2 kb band did not give visible hybridization in this exposure. 4) DNA from untransformed duckweed with the equivalent of 1 copy of doubly-digested, pBI121 DNA giving the expected 9 and 3.2 kb bands. 5) Untransformed duckweed DNA. 6) Undigested DNA from transformed duckweed line D. 7) HindIII digested DNA from transformed duckweed line D. 8) HindIII and EcoR1 digested DNA from transformed duckweed line D.

The present invention is directed to methods for transforming duckweed. In preferred embodiments, the methods utilize ballistic bombardment or Agrobacterium to stably transform the duckweed cells. Alternately, the methods use electroporation to transform duckweed. The methods and transformed plants of the present invention find use as a plant-based gene expression system possessing many of the advantages of yeast.

As far as the inventors are aware, there are no previous reports of stable gene transfer in duckweed nor of regeneration of transformed duckweed plants. In the present investigations two strategies have been utilized for the production of transgenic duckweed plants: (1) By directly transferring and inserting foreign DNA into meristematic frond cells followed by asexual propagation and selfing to produce transgenic duckweed (a plant-to-plant system), and (2) Transformation of undifferentiated callus cells, followed by selection of proliferating callus, and frond regeneration (a callus-to-plant system). Limited tissue culture systems for callus production from *L. gibba* and *L. minor* have previously been reported by Chang's group (Chang and Chui, *Bot. Bull. Academia Sinica* 17, 106 (1976); Chang and Chui, *Z. Pflanzenphysiol. Bd.* 89.S, 91 (1978)) and Frick (Frick, *J. Plant Physiology* 137, 397 (1991)), respectively. The present investigations have significantly extended the work in this area by developing an organized callus system that regenerates fronds.

Preferably, the present invention utilizes one of two systems to stably transform duckweed: ballistic transformation using microprojectile bombardment or Agrobacterium-mediated transformation. Although duckweeds would be expected to be refractory to Agrobacterium transformation because they are monocotyledonous plants, it has unexpectedly been found that duckweed can be transformed using Agrobacterium. Transformed duckweed plants according to the present invention may also be generated by electroporation. See, e.g., Dekeyser et al., *Plant Cell* 2, 591 (1990); D'Halluin et al., *Plant Cell* 4, 1495 (1992); U.S. Pat. No. 5,712,135 to D'Halluin et al. One advantage of electroporation is that large pieces of DNA, including artificial chromosomes, can be transformed into duckweed by this method. Any suitable duckweed cell or tissue type can be transformed according to the present invention. For example, nucleic acids can be introduced into duckweed cells in tissue culture. Alternately, the small size and aquatic growth habit of duckweed plants allows for nucleic acids to be introduced into duckweed cells of intact embryos, fronds, roots, and other organized tissues, such as meristematic tissue. As a further alternative, nucleic acids can be introduced into duckweed callus.

It is preferred that the transformed duckweed plants produced by the claimed methods exhibit normal morphology and are fertile by sexual reproduction. Preferably, transformed plants of the present invention contain a single copy of the transferred nucleic acid, and the transferred nucleic acid has no notable rearrangements therein. Also preferred are duckweed plants in which the transferred nucleic acid is present in low copy numbers (i.e., no more than five copies, alternately, no more than three copies, as a further alternative, fewer than three copies of the nucleic acid per transformed cell).

The term "duckweed", as used herein, refers to members of the family Lemnaceae. There are known four genera and 34 species of duckweed as follows: genus Lemna (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus Spirodela (*S. intermedia, S. polyrrhiza, S. punctata*); genus Wolffia (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus Wolfiella (*Wl. caudata, Wl. denticulata, Wl. gladiata, Wl. hyalina, Wl. lingulata, Wl. repunda, Wl. rotunda,* and *Wl. neotropica*). Any other genera or species of Lemnaceae, if they exist, are also aspects of the present invention. *Lemna gibba, Lemna minor,* and *Lemna miniscula* are preferred, with *Lemna minor* and *Lemna miniscula* being most preferred. Lemna species can be classified using the taxonomic scheme described by Landolt, *Biosystematic Investigation on the Family of Duckweeds: The family of Lemnaceae—A Monograph Study.* Geobatanischen Institut ETH, Stiftung Rubel, Zurich (1986)).

As will be evident to one of skill in the art, now that a method has been provided for the efficient transformation of duckweed, any nucleic acid of interest can be used in the methods of the invention. For example, a duckweed plant can be engineered to express disease and insect resistance genes, genes conferring nutritional value, antifungal, antibacterial or antiviral genes, and the like. Alternatively, therapeutic (e.g., for veterinary or medical uses) or immunogenic (e.g., for vaccination) peptides and proteins can be expressed using transformed duckweed according to the present invention.

Likewise, the method can be used to transfer any nucleic acid for controlling gene expression. For example, the nucleic acid to be transferred can encode an antisense oligonucleotide. Alternately, duckweed can be transformed with one or more genes to reproduce enzymatic pathways for chemical synthesis (e.g. for the synthesis of plastics) or other industrial processes (e.g., keratinase). The nucleic acid may be from duckweed or from another organism (i.e., heterologous). Moreover, nucleic acids of interest can be obtained from prokaryotes or eukaryotes (e.g., bacteria, fungi, yeast, viruses, plants, mammals) or the nucleic acid sequence can be synthesized in whole or in part. In particular preferred embodiments, the nucleic acid encodes a secreted protein or peptide.

Preferably, the transferred nucleic acid to be expressed in the transformed duckweed encodes a protein hormone, growth factor, or cytokine, more preferably, insulin, growth hormone (in particular, human growth hormone), and α-interferon. Alternatively, it is also preferred that the nucleic acid expresses β-glucocerebrosidase.

Also preferred are nucleic acids that encode peptides or proteins that cannot effectively be commercially-produced by existing gene expression systems, because of cost or logistical constraints, or both. For example, some proteins cannot be expressed in mammalian systems because the protein interferes with cell viability, cell proliferation, cellular differentiation, or protein assembly in mammalian cells. Such proteins include, but are not limited to, retinoblastoma protein, p53, angiostatin and leptin. The present invention can be advantageously employed to produce mammalian regulatory proteins; it is unlikely given the large evolutionary distance between higher plants and mammals that these proteins will interfere with regulatory processes in duckweed. Transgenic duckweed can also be used to produce large quantities of proteins such as serum albumin (in particular, human serum albumin), hemoglobin and collagen, which challenge the production capabilities of existing expression systems.

Finally, as described in more detail below, higher plant systems can be engineered to produce (i.e., synthesize, express, assemble) biologically-active multimeric proteins (e.g., monoclonal antibodies, hemoglobin, P450 oxidase, and collagen, and the like) far more easily than can mammalian systems. Those skilled in the art will appreciate that the term "biologically active" includes multimeric proteins in which the biological activity is altered as compared with the native protein (e.g, suppressed or enhanced), as long as the protein has sufficient activity to be of interest for use in industrial or chemical processes or as a therapeutic, vaccine, or diagnostics reagent.

One exemplary approach for producing biologically-active multimeric proteins in duckweed uses an expression vector containing the genes encoding all of the polypeptide subunits. See, e.g., During et al. (1990) *Plant Molecular Biology* 15:281; van Engelen et al., (1994) *Plant Molecular Biology* 26:1701. This vector is then introduced into duckweed cells using any known transformation method, such as a gene gun or Agrobacterium-mediated transformation. This method results in clonal cell lines that express all of the polypeptides necessary to assemble the multimeric protein. As one alternate method, independent vector constructs are made that encode each polypeptide subunit. Each of these vectors is used to generate separate clonal lines of transgenic plants expressing only one of the necessary polypeptides. These transgenic plants are then crossed to create progeny that express all of the necessary polypeptides within a single plant. See Hiatt et al., (1989) *Nature* 342:76; U.S. Pat. Nos. 5,202,422 and 5,639,947 to Hiatt et al. A variation on this approach is to make single gene constructs, mix DNA from these constructs together, then deliver this mixture of DNAs into plant cells using ballistic bombardment or Agrobacterium-mediated transformation, more preferably ballistic bombardment. As a further variation, some or all of the vectors may encode more than one subunit of the multimeric protein (i.e., so that there are fewer duckweed clones to be crossed than the number of subunits in the multimeric protein). Finally, in some instances, it may be desirable to produce less than all of the subunits of a multimeric protein, or even a single protein subunit, in a transformed duckweed plant, e.g., for industrial or chemical processes or for diagnostic, therapeutic or vaccination purposes.

A. Expression Cassettes

According to the present invention, the nucleic acid to be transferred is contained within an expression cassette. The expression cassette comprises a transcriptional initiation region linked to the nucleic acid or gene of interest. Such an expression cassette is provided with a plurality of restriction sites for insertion of the gene or genes of interest (e.g., one gene of interest, two genes of interest, etc.) to be under the transcriptional regulation of the regulatory regions. Preferably, the expression cassette encodes a single gene of interest. In particular embodiments of the invention, the nucleic acid to be transferred contains two or more expression cassettes, each of which encodes at least one gene of interest (preferably one gene of interest).

The transcriptional initiation region, (e.g., a promoter) may be native or homologous or foreign or heterologous to the host, or could be the natural sequence or a synthetic sequence. By foreign, it is intended that the transcriptional initiation region is not found in the wild-type host into which the transcriptional initiation region is introduced. As used herein a chimeric gene comprises a coding sequence operably linked to a transcription initiation region that is heterologous to the coding sequence.

Any suitable promoter known in the art can be employed according to the present invention (including bacterial, yeast, fungal, insect, mammalian, and plant promoters). Plant promoters are preferred, with duckweed promoters being most preferred. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art. Silverthrone et al., (1990) *Plant Mol. Biol.* 15:49. Other promoters from viruses that infect plants, preferably duckweed, are also suitable including, but not limited to, promoters isolated from Dasheen mosaic virus, Chlorella virus (e.g., the Chlorella virus adenine methyltransferase promoter; Mitra et al., (1994) *Plant Molecular Biology* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, and the like.

Finally, promoters can be chosen to give a desired level of regulation. For example, in some instances, it may be advantageous to use a promoter that confers constitutive expression (e.g, the ubiquitin promoter, the RubP carboxylase gene family promoters, and the actin gene family promoters). Alternatively, it other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid). As a further alternative, promoters can be chosen that give tissue-specific expression (e.g., root, leaf and floral-specific promoters).

The transcriptional cassette includes in the 5'-3' direction of transcription, a transcriptional and translational initiation region, a nucleotide sequence of interest, and a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens,* such as the octopine synthetase and nopaline synthetase termination regions. See also, Guerineau et al., *Mol. Gen. Genet.* 262, 141 (1991); Proudfoot, *Cell* 64, 671 (1991); Sanfacon et al., *Genes Dev.* 5, 141 (1991); Mogen et al., *Plant Cell* 2, 1261 (1990); Munroe et al., *Gene* 91, 151 (1990); Ballas et al., *Nucleic Acids Res.* 17, 7891 (1989); and Joshi et al., *Nucleic Acids Res.* 15, 9627 (1987). Additional exemplary termination sequences are the pea RubP carboxylase small subunit termination sequence and the Cauliflower Mosaic Virus 35S termination sequence. Other suitable termination sequences will be apparent to those skilled in the art.

Alternatively, the gene(s) of interest can be provided on any other suitable expression cassette known in the art. Where appropriate, the gene(s) may be optimized for increased expression in the transformed plant. Where mammalian, yeast or bacterial or plant dicot genes are used in the invention, they can be synthesized using monocot or duckweed preferred codons for improved expression. Methods are available in the art for synthesizing plant preferred genes. See, e.g., U.S. Pat. Nos. 5,380,831; 5,436,391; and Murray et al., *Nucleic Acids. Res.* 17, 477 (1989); herein incorporated by reference.

The expression cassettes may additionally contain 5' leader sequences. Such leader sequences can act to enhance translation. Translation leaders are known in the art and include: picornavirus leaders, e.g., EMCV leader (Encephalomyocarditis 5' noncoding region; Elroy-Stein et al., *Proc. Natl. Acad. Sci* USA, 86, 6126 (1989)).; potyvirus leaders, e.g., TEV leader (Tobacco Etch Virus; Allison et al., *Virology,* 154, 9 (1986)); human immunoglobulin heavy-chain binding protein (BiP; Macajak and Sarnow, *Nature* 353, 90 (1991)); untranslated leader from the coat protein mRNA of alfalfa mosaic virus (AMV RNA 4; Jobling and Gehrke, *Nature* 325, 622 (1987)); tobacco mosaic virus leader (TMV; Gallie, MOLECULAR BIOLOGY OF RNA, 237–56 (1989)); and maize chlorotic mottle virus leader (MCMV; Lommel et al., *Virology* 81, 382 (1991)). See also, Della-Cioppa et al., *Plant Physiology* 84, 965 (1987). Other methods known to enhance translation can also be utilized, e.g., introns and the like.

The exogenous nucleic acid of interest may additionally be operably associated with a nucleic acid sequence that encodes a transit peptide that directs expression of the encoded peptide or protein of interest to a particular cellular compartment. Transit peptides that target protein accumulation in higher plants cells to the chloroplast, mitochondrion, vacuole, nucleus, and the endoplasmic reticulum (for secretion outside of the cell) are known in the art. Preferably, the transit peptide targets the protein expressed from the exogenous nucleic acid to the chloroplast or the endoplasmic reticulum. Transit peptides that target proteins to the endoplasmic reticulum are desirable for correct processing of secreted proteins. Targeting protein expression to the chloroplast (for example, using the transit peptide from the RubP carboxylase small subunit gene) has been shown to result in the accumulation of very high concentrations of recombinant protein in this organelle. A duckweed nucleic acid encoding an RubP carboxylase transit peptide has already been cloned. Stiekma et al., (1983) *Nucl. Acids Res.* 11:8051–61; see also U.S. Pat. Nos. 5,717,084 and 5,728,925 to Herrera-Estrella et al. The pea RubP carboxylase small subunit transit peptide sequence has been used to express and target mammalian genes in plants. U.S. Pat. Nos. 5,717,084 and 5,728,925 to Herrera-Estrella et al. Alternatively, mammalian transit peptides can be used to target recombinant protein expression, for example, to the mitochondrion and endoplasmic reticulum. It has been demonstrated that plant cells recognize mammalian transit peptides that target endoplasmic reticulum. U.S. Pat. Nos. 5,202,422 and 5,639,947 to Hiatt et al.

The expression cassettes may contain more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells. Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See, DeBlock et al., *EMBO J.* 6, 2513 (1987); DeBlock et al., *Plant Physiol.* 91, 691 (1989); Fromm et al., *BioTechnology* 8, 833 (1990); Gordon-Kamm et al., *Plant Cell* 2, 603 (1990). For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding: neomycin phosphotransferase II (Fraley et al., *CRC Critical Reviews in Plant Science* 4, 1 (1986)); cyanamide hydratase (Maier-Greiner et al., *Proc. Natl. Acad. Sci.* USA 88, 4250 (1991)); aspartate kinase; dihydrodipicolinate synthase (Perl et al., *BioTechnology* 11, 715 (1993)); bar gene (Toki et al., *Plant Physiol.* 100, 1503 (1992); Meagher et al., *Crop Sci.* 36, 1367 (1996)); tryptophane decarboxylase (Goddijn et al., *Plant Mol. Biol.* 22, 907 (1993)); neomycin phosphotransferase (NEO; Southern et al., *J. Mol. Appl. Gen.* 1, 327 (1982)); hygromycin phosphotransferase (HPT or HYG; Shimizu et al., *Mol. Cell. Biol.* 6, 1074 (1986)); dihydrofolate reductase (DHFR; Kwok et al., *Proc. Natl. Acad. Sci.* USA vol, 4552 (1986)); phosphinothricin acetyltransferase (DeBlock et al., *EMBO J.* 6, 2513 (1987)); 2,2-dichloropropionic acid dehalogenase (Buchanan-Wollatron et al., *J. Cell. Biochem.* 13D, 330 (1989)); acetohydroxyacid synthase (U.S. Pat. No. 4,761,373 to Anderson et al.; Haughn et al., *Mol. Gen. Genet.* 221, 266 (1988)); 5-enolpyruvyl-shikimate-phosphate synthase (aroA; Comai et al., *Nature* 317, 741 (1985)); haloarylnitrilase (WO 87/04181 to Stalker et al.); acetyl-coenzyme A carboxylase (Parker et al., *Plant Physiol.* 92, 1220 (1990)); dihydropteroate synthase (sulI; Guerineau et al., *Plant Mol. Biol.* 15, 127 (1990)); and 32 kDa photosystem II polypeptide (psbA; Hirschberg et al., *Science* 222, 1346 (1983)).

Also included are genes encoding resistance to: chloramphenicol (Herrera-Estrella et al., *EMBO J.* 2, 987 (1983)); methotrexate (Herrera-Estrella et al., *Nature* 303, 209 (1983); Meijer et al., *Plant Mol. Biol.* 16, 807 (1991)); hygromycin (Waldron et al., *Plant Mol. Biol.* 5, 103 (1985); Zhijian et al., *Plant Science* 108, 219 (1995); Meijer et al., *Plant Mol. Bio.* 16, 807 (1991)); streptomycin (Jones et al., *Mol. Gen. Genet.* 210, 86 (1987)); spectinomycin (Bretagne-Sagnard et al., *Transgenic Res.* 5, 131 (1996)); bleomycin (Hille et al., *Plant Mol. Biol.* 7, 171 (1986)); sulfonamide (Guerineau et al., *Plant Mol. Bio.* 15, 127 (1990); bromoxynil (Stalker et al., *Science* 242, 419 (1988)); 2,4-D (Streber et al., *Bio/Technology* 7, 811 (1989)); phosphinothricin (DeBlock et al., *EMBO J.* 6, 2513 (1987)); spectinomycin (Bretagne-Sagnard and Chupeau, *Transgenic Research* 5, 131 (1996)).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See generally, Yarranton, *Curr. Opin. Biotech.* 3, 506 (1992); Chistophersen et al., *Proc. Natl. Acad. Sci.* USA 89, 6314 (1992); Yao et al., *Cell* 71, 63 (1992); Reznikoff, *Mol. Microbiol.* 6, 2419 (1992); BARKLEY ET AL., THE OPERON 177–220 (1980); Hu et al., *Cell* 48, 555 (1987); Brown et al., *Cell* 49, 603 (1987); Figge et al., *Cell* 52, 713 (1988); Deuschle et al., *Proc. Natl. Acad. Sci.* USA 86, 5400 (1989); Fuerst et al., *Proc. Natl. Acad. Sci.* USA 86, 2549 (1989); Deuschle et al., *Science* 248, 480 (1990); Labow et al., *Mol. Cell. Biol.* 10, 3343 (1990); Zambretti et al., *Proc. Natl. Acad. Sci.* USA 89, 3952 (1992); Baim et al., *Proc. Natl. Acad. Sci.* USA 88, 5072 (1991); Wyborski et al., *Nuc. Acids Res.* 19, 4647 (1991); Hillenand-Wissman, *Topics in Mol. And Struc. Biol.* 10, 143 (1989); Degenkolb et al., *Antimicrob. Agents Chemother.* 35, 1591 (1991); Kleinschnidt et al., *Biochemistry* 27, 1094 (1988); Gatz et al., *Plant J.* 2, 397 (1992); Gossen et al., *Proc. Natl. Acad. Sci.* USA 89, 5547 (1992); Oliva et al., *Antimicrob. Agents Chemother.* 36, 913 (1992); HLAVKA ET AL., HANDBOOK OF EXPERIMENTAL PHARMACOLOGY 78 (1985); and Gill et al., *Nature* 334, 721 (1988). Such disclosures are herein incorporated by reference.

The above list of selectable marker genes are not meant to be limiting. Any selectable marker gene can be used in the present invention.

Where appropriate, the selectable marker genes and other gene(s) and nucleic acids of interest to be transferred can be synthesized for optimal expression in duckweed. That is, the coding sequence of the genes can be modified to enhance expression in duckweed. The synthetic nucleic acid is designed to be expressed in the transformed tissues and plants at a higher level. The use of optimized selectable marker genes may result in higher transformation efficiency.

Methods for synthetic optimization of genes are available in the art. The nucleotide sequence can be optimized for expression in duckweed or alternatively can be modified for optimal expression in monocots. The plant preferred codons may be determined from the codons of highest frequency in the proteins expressed in duckweed. It is recognized that genes which have been optimized for expression in duckweed and other monocots can be used in the methods of the invention. See, e.g., EP 0 359 472, EP 0 385 962, WO 91/16432; Perlak et al., *Proc. Natl. Acad. Sci. USA* 88, 3324 (1991), and Murray et al., *Nuc. Acids Res.* 17, 477 (1989), and the like, herein incorporated by reference. It is further recognized that all or any part of the gene sequence may be optimized or synthetic. In other words, fully optimized or partially optimized sequences may also be used.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

B. Target Tissues and Callus

The methods of the invention are useful for transforming duckweed plant cells, preferably frond and meristematic cells. Such cells also include callus, which can be originated from any tissue of duckweed plants. Preferably, the tissue utilized in initiating callus is meristematic tissue. Alternatively, the callus can be originated from any other frond cells, or in principal from any other duckweed tissue capable of forming callus. Alternatively stated, any tissue capable of subsequent clonal propagation, whether by organogenesis or embryogenesis, may be employed to transform duckweed according to the present invention. The term "organogenesis", as used herein, means a process whereby fronds and roots are developed sequentially from meristematic centers. The term "embryogenesis", as used herein, means a process whereby fronds and roots develop together in a concerted fashion (not sequentially), whether from somatic cells or gametes.

The method can also be used to transform cell suspensions. Such cell suspensions can be formed from any duckweed tissue.

The duckweeds make three kinds of callus: (a) a compact, semi-organized callus (designated Type 1); (b) a friable, white, undifferentiated callus (designated Type II); and (c) a green, differentiated callus (designated Type III). In tissue culture, callus can only regenerate plants two ways: via embryos and via shoot formation (in duckweed the frond is the shoot). Methods of callus induction are known in the art, and the particular conditions to be employed can be optimized for each duckweed species and for the type of callus desired, as demonstrated in the Examples below. Preferably, Type I or Type III callus, more preferably Type I callus, is used to transform duckweed according to the present invention.

Callus can be induced by cultivating duckweed tissue in medium containing plant growth regulators, i.e., cytokinins and auxins. Preferred auxins for callus induction from duckweed tissue include 2,4-dichlorophenoxyacetic acid (2,4-D) and naphthaleneacetic acid (NAA). Preferred auxin concentrations are 1–30 $\mu$M, more preferably 5–20 $\mu$M, yet more preferably 5–10 $\mu$M. The preferred cytokinin is benzyladenine (BA) or thidiazuron (TDZ). Preferred cytokinin concentrations are 0.1–10 $\mu$M, more preferably 0.5–5 $\mu$M, yet more preferably 0.5–1 $\mu$M. In other more preferred embodiments, callus is induced by cultivating duckweed tissue in medium containing both BA or TDZ and either 2,4-D or NAA. In general, low concentrations of auxin or "weak" auxins (e.g., indoleacetic acid) promote frond proliferation rather than callus formation, and high concentrations of auxin or "strong" auxins (e.g. 2,4-D) promote callus formation. Preferred basal media for callus formation include N6 medium (Chu et al., *Scientia Sinica* 18, 659 (1975)) and Murashige and Skoog medium (Murashige and Skoog, *Physiol. Plant.* 15, 473 (1962)), with Murashige and Skoog medium being more preferred. In general, callus induction frequency is variable. In these species, callus may not be visible for two to three weeks in culture, and it may take four to eight weeks of cultivation before calli are of sufficient size for transformation. Preferably, callus induction is carried out for a period of 1–10 weeks, more preferably 2–8 weeks, yet more preferably 3–5 weeks. For callus growth, the preferred media are as for callus induction, but the auxin concentration is reduced.

C. Transformation of Duckweed by Ballistic Bombardment

One embodiment of the invention is a method of transforming duckweed with a nucleotide sequence of interest, wherein the nucleotide sequence contains at least an expression cassette carrying a gene that confers resistance to a selection agent. The nucleotide sequence is carried by a microprojectile. As far as the inventors are aware, there are no previous reports of producing stably transformed duckweed by means of ballistic transformation.

According to preferred embodiments of the present invention, the ballistic transformation method comprises the steps of: (a) providing a duckweed tissue as a target; (b) propelling the microprojectile carrying the nucleotide sequence at the duckweed tissue at a velocity sufficient to pierce the walls of the cells within the tissue and to deposit the nucleotide sequence within a cell of the tissue to thereby provide a transformed tissue. In particular embodiments of the invention, the method further includes the step of culturing the transformed tissue with a selection agent, as described below. In a further alternate embodiment, the selection step is followed by the step of regenerating transformed duckweed plants from the transformed tissue. As noted below, the technique could be carried out with the nucleotide sequence as a precipitate (wet or freeze-dried) alone, in place of the aqueous solution containing the nucleotide sequence.

Any ballistic cell transformation apparatus can be used in practicing the present invention. Exemplary apparatus are disclosed by Sandford et al. (*Particulate Science and Technology* 5, 27 (1988)), Klein et al. (*Nature* 327, 70 (1987)), and in EP 0 270 356. Such apparatus have been used to transform maize cells (Klein et al., *Proc. Natl. Acad. Sci. USA* 85, 4305 (1988)), soybean callus (Christou et al., *Plant Physiol.* 87, 671 (1988)), McCabe et al., *BioTechnology* 6, 923 (1988)), yeast mitochondria (Johnston et al., *Science* 240, 1538 (1988)), and Chlamydomonas chloroplasts (Boynton et al., *Science* 240, 1534 (1988)).

In the investigations presented herein, a commercially-available helium gene gun (PDS-1000/He) manufactured by DuPont was employed. Alternately, an apparatus configured as described by Klein et al. (*Nature* 70, 327 (1987)) may be utilized. This apparatus comprises a bombardment chamber, which is divided into two separate compartments by an adjustable-height stopping plate. An acceleration tube is mounted on top of the bombardment chamber. A macroprojectile is propelled down the acceleration tube at the stopping plate by a gunpowder charge. The stopping plate has a bore hole formed therein, which is smaller in diameter than the microprojectile. The macroprojectile carries the microprojectile(s), and the macroprojectile is aimed and fired at the bore hole. When the macroprojectile is stopped by the stopping plate, the microprojectile(s) is propelled through the bore hole. The target tissue is positioned in the bombardment chamber so that a microprojectile(s) propelled through the bore hole penetrates the cell walls of the cells in the target tissue and deposit the nucleotide sequence of interest carried thereon in the cells of the target tissue. The bombardment chamber is partially evacuated prior to use to prevent atmospheric drag from unduly slowing the microprojectiles. The chamber is only partially evacuated so that the target tissue is not desiccated during bombardment. A vacuum of between about 400 to about 800 millimeters of mercury is suitable.

In alternate embodiments, ballistic transformation is achieved without use of microprojectiles. For example, an aqueous solution containing the nucleotide sequence of interest as a precipitate could be carried by the macroprojectile (e.g., by placing the aqueous solution directly on the plate-contact end of the macroprojectile without a microprojectile, where it is held by surface tension), and the solution alone propelled at the plant tissue target (e.g., by propelling the macroprojectile down the acceleration tube in the same manner as described above). Other approaches include placing the nucleic acid precipitate itself ("set" precipitate) or a freeze-dried nucleotide precipitate directly on the plate-contact end of the macroprojectile without a microprojectile. In the absence of a microprojectile, it is believed that the nucleotide sequence must either be propelled at the tissue target at a greater velocity than that needed if carried by a microprojectile, or the nucleotide sequenced caused to travel a shorter distance to the target tissue (or both).

It is currently preferred to carry the nucleotide sequence on a microprojectile. The microprojectile may be formed from any material having sufficient density and cohesiveness to be propelled through the cell wall, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Metallic particles are currently preferred. Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue. Particles ranging in diameter from about one-half micrometer to about three micrometers are suitable. Particles need not be spherical, as surface irregularities on the particles may enhance their DNA carrying capacity.

The nucleotide sequence may be immobilized on the particle by precipitation. The precise precipitation parameters employed will vary depending upon factors such as the particle acceleration procedure employed, as is known in the art. The carrier particles may optionally be coated with an encapsulating agents such as polylysine to improve the stability of nucleotide sequences immobilized thereon, as discussed in EP 0 270 356 (column 8).

After ballistic bombardment of the target tissue, transformants may be selected and transformed duckweed plants regenerated as described below in Section E.

D. Agrobacterium-mediated Transformation

In one embodiment of the present invention, duckweed is transformed using *Agrobacterium tumefaciens* or *Agrobacterium rhizogenes,* preferably *Agrobacterium tumefaciens.* Agrobacterium-mediated gene transfer exploits the natural ability of *A. tumefaciens* and *A. rhizogenes* to transfer DNA into plant chromosomes. Agrobacterium is a plant pathogen that transfers a set of genes encoded in a region called T-DNA of the Ti and Ri plasmids of *A. tumefaciens* and *A. rhizogenes,* respectively, into plant cells. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease". The ability to cause disease in the host plant can be removed by deletion of the genes in the T-DNA without loss of DNA transfer and integration. The DNA to be transferred is attached to border sequences that define the end points of an integrated T-DNA.

Gene transfer by means of engineered Agrobacterium strains has become routine for many dicotyledonous crop plants. Considerable difficulty has been experienced, however, in using Agrobacterium to transform monocotyledonous plants, in particular, cereal plants. As far as the inventors are aware, there are no reports to date of producing stably transformed duckweed by means of Agrobacterium-mediated transformation.

While the following discussion will focus on using *A. tumefaciens* to achieve gene transfer in duckweed, those skilled in the art will appreciate that this discussion applies equally well to *A. rhizogenes.* Transformation using *A. rhizogenes* has developed analogously to that of *A. tumefaciens* and has been successfully utilized to transform, for example, alfalfa, *Solanum nigrum L.,* and poplar. U.S. Pat. No. 5,777,200 to Ryals et al. As described by U.S. Pat. No. 5,773,693 to Burgess et al., it is preferable to use a disarmed *A. tumefaciens* strain (as described below), however, the wild-type *A. rhizogenes* may be employed. An illustrative strain of *A. rhizogenes* is strain 15834.

The Agrobacterium strain utilized in the methods of the present invention is modified to contain a gene or genes of interest, or a nucleic acid to be expressed in the transformed cells. The nucleic acid to be transferred is incorporated into the T-region and is flanked by T-DNA border sequences. A variety of Agrobacterium strains are known in the art particularly for dicotyledon transformation. Such Agrobacterium can be used in the methods of the invention. See, e.g., Hooykaas, *Plant Mol. Biol.* 13, 327 (1989); Smith et al., *Crop Science* 35, 301 (1995); Chilton, *Proc. Natl. Acad. Sci. USA* 90, 3119 (1993); Mollony et al., *Monograph Theor. Appl. Genet NY* 19, 148 (1993); Ishida et al., *Nature Biotechnol.* 14, 745 (1996); and Komari et al., *The Plant Journal* 10, 165 (1996), the disclosures of which are incorporated herein by reference.

In addition to the T-region, the Ti (or Ri) plasmid contains a vir region. The vir region is important for efficient transformation, and appears to be species-specific. Binary vector systems have been developed where the manipulated disarmed T-DNA carrying foreign DNA and the vir functions are present on separate plasmids. In this manner, a modified T-DNA region comprising foreign DNA (the nucleic acid to be transferred) is constructed in a small plasmid which replicates in *E. coli.* This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. Such binary vectors are useful in the practice of the present invention.

In preferred embodiments of the invention C58-derived vectors are employed to transform *A. tumefaciens*. Alternately, in other embodiments, super-binary vectors are employed. See, e.g., U.S. Pat. No. 5,591,615 and EP 0 604 662, herein incorporated by reference. Such a super-binary vector has been constructed containing a DNA region originating from the hypervirulence region of the Ti plasmid pTiBo542 (Jin et al., *J. Bacteriol.* 169, 4417 (1987)) contained in a super-virulent *A. tumefaciens* A281 exhibiting extremely high transformation efficiency (Hood et al., *Biotechnol.* 2, 702 (1984); Hood et al., *J. Bacteriol.* 168, 1283 (1986); Komari et al., *J. Bacteriol.* 166, 88 (1986); Jin et al., *J. Bacteriol.* 169, 4417 (1987); Komari, *Plant Science* 60, 223 (1987); ATCC Accession No. 37394.

Exemplary super-binary vectors known to those skilled in the art include pTOK162 (Japanese patent Appl. (Kokai) No. 4-222527, EP 504,869, EP 604,662, and U.S. Pat. No. 5,591,616, herein incorporated by reference) and pTOK233 (Komari, *Plant Cell Reports* 9, 303 (1990); Ishida et al., *Nature Biotechnology* 14, 745 (1996); herein incorporated by reference). Other super-binary vectors may be constructed by the methods set forth in the above references. Super-binary vector pTOK162 is capable of replication in both *E. coli* and in *A. tumefaciens*. Additionally, the vector contains the virB, virC and virG genes from the virulence region of pTiBo542. The plasmid also contains an antibiotic resistance gene, a selectable marker gene, and the nucleic acid of interest to be transformed into the plant. The nucleic acid to be inserted into the duckweed genome is located between the two border sequences of the T region. Super-binary vectors of the invention can be constructed having the features described above for pTOK162. The T-region of the super-binary vectors and other vectors for use in the invention are constructed to have restriction sites for the insertion of the genes to be delivered. Alternatively, the DNA to be transformed can be inserted in the T-DNA region of the vector by utilizing in vivo homologous recombination. See, Herrera-Esterella et al., *EMBO J.* 2, 987 (1983); Horch et al., *Science* 223, 496 (1984). Such homologous recombination relies on the fact that the super-binary vector has a region homologous with a region of pBR322 or other similar plasmids. Thus, when the two plasmids are brought together, a desired gene is inserted into the super-binary vector by genetic recombination via the homologous regions.

Any suitable vector for transforming duckweed may be employed according to the present invention. For example, the heterologous nucleic acid sequence of interest and the flanking T-DNA can be carried by a binary vector lacking the vir region. The vir region is then provided on a disarmed Ti-plasmid or on a second binary plasmid. As another alternative, the heterologous nucleic acid sequence and the T-DNA border sequences can be put into the T-DNA site on the Ti-plasmid through a double recombination event by which the new T-DNA replaces the original Ti-plasmid T-DNA. The vir region can be supplied by the Ti-plasmid or on a binary plasmid. As yet a further alternative, the heterologous nucleic acid sequence and flanking T-DNA can be integrated into the bacterial chromosome as described by U.S. Pat. No. 4,940,838 to Schilperoort et al., and the vir region can then be supplied on a Ti-plasmid or on a binary plasmid.

The Agrobacterium-mediated transformation process of the present invention can be thought of as comprising several steps. The basic steps include an infection step and a co-cultivation step. In some embodiments, these steps are followed by a selection step, and in other embodiments by a selection and a regeneration step.

An optional pre-culture step may be included prior to the infection step. The pre-culture step involves culturing the callus, frond, or other target tissue prior to the infection step on a suitable medium. The pre-culture period may vary from about 1 to 21 days, preferably 7 to 14 days. Such a pre-culture step was found to prevent transformation of maize cultures. See, e.g., EP 0 672 752.

In the infection step, the cells to be transformed are exposed to Agrobacterium. The cells are brought into contact with the Agrobacterium, typically in a liquid medium. As noted above, the Agrobacterium has been modified to contain a gene or nucleic acid of interest. The nucleic acid is inserted into the T-DNA region of the vector. General molecular biology techniques used in the invention are well-known by those of skill in the art. See, e.g., SAMBROOK ET AL., MOLECULAR CLONING: A LABORATORY MANUAL (1989).

Agrobacterium containing the plasmid of interest are preferably maintained on Agrobacterium master plates with stock frozen at about $-80°$ C. Master plates can be used to inoculate agar plates to obtain Agrobacterium that is then resuspended in medium for use in the infection process. Alternatively, bacteria from the master plate can be used to inoculate broth cultures that are grown to logarithmic phase prior to transformation.

The concentration of Agrobacterium used in the infection step and co-cultivation step can affect the transformation frequency. Likewise, very high concentrations of Agrobacterium may damage the tissue to be transformed and result in a reduced callus response. Thus, the concentration of Agrobacterium useful in the methods of the invention may vary depending on the Agrobacterium strain utilized, the tissue being transformed, the duckweed species being transformed, and the like. To optimize the transformation protocol for a particular duckweed species or tissue, the tissue to be transformed can be incubated with various concentrations of Agrobacterium. Likewise, the level of marker gene expression and the transformation efficiency can be assessed for various Agrobacterium concentrations. While the concentration of Agrobacterium may vary, generally a concentration range of about $1 \times 10^3$ cfu/ml to about $1 \times 10^{10}$ cfu/ml is employed, preferably within the range of about $1 \times 10^3$ cfu/ml to about $1 \times 10^9$ cfu/ml, and still more preferably at about $1 \times 10^8$ cfu/ml to about $1 \times 10^9$ cfu/ml will be utilized.

The tissue to be transformed is generally added to the Agrobacterium suspension in a liquid contact phase containing a concentration of Agrobacterium to optimize transformation efficiencies. The contact phase facilitates maximum contact of the tissue to be transformed with the suspension of Agrobacterium. Infection is generally allowed to proceed for 1 to 30 minutes, preferably 1 to 20 minutes, more preferably 2 to 10 minutes, yet more preferably 3 to 5 minutes prior to the co-cultivation step.

Those skilled in the art will appreciate that the conditions can be optimized to achieve the highest level of infection and transformation by Agrobacterium. For example, in preferred embodiments of the invention the cells are subjected to osmotic pressure (e.g., 0.6 M mannitol) during the infection and co-cultivation steps. Additionally, to enhance transformation efficiency, tissue may be cultured in medium containing an auxin, such as IAA, to promote cell proliferation (i.e., it is believed that Agrobacterium integrates into the genome during mitosis). As further alternatives, tissue wounding, vacuum pressure, or cultivation in medium containing acetosyringone can be employed to promote the transformation efficiency.

In the co-cultivation step, the cells to be transformed are co-cultivated with Agrobacterium. Typically, the co-cultivation takes place on a solid medium. Any suitable medium, such as Schenk and Hildebrandt medium (Schenk and Hildebrandt, *Can. J. Bot.* 50, 199 (1972)) containing 1% sucrose and 0.6% agar, may be utilized. The optimal co-cultivation time varies with the particular tissue. Fronds are co-cultivated with the Agrobacterium for about 2 to 7 days, preferably 2 to 5 days, more preferably 3 to 5 days, and more preferably 4 days. In contrast, callus is co-cultivated with the Agrobacterium for 0.5 to 4 days, more preferably 1 to 3 days, more preferably 2 days. Co-cultivation may be carried out in the dark or under subdued light conditions to enhance the transformation efficiency. Additionally, as described above for the inoculation step, co-culturing can be done on medium containing IAA or acetosyringone to promote transformation efficiency. Finally, the co-culturing step may be performed in the presence of cytokinins, which act to enhance cell proliferation.

Following the co-cultivation step, the transformed tissue may be subjected to an optional resting and decontamination step. For the resting/decontamination step, the transformed cells are transferred to a second medium containing an antibiotic capable of inhibiting the growth of Agrobacterium. This resting phase is performed in the absence of any selective pressures to permit recovery and proliferation of transformed cells containing the heterologous nucleic acid. An antibiotic is added to inhibit Agrobacterium growth. Such antibiotics are known in the art which inhibit Agrobacterium and include cefotaxime, timetin, vancomycin, carbenicillin, and the like. Concentrations of the antibiotic will vary according to what is standard for each antibiotic. For example, concentrations of carbenicillin will range from about 50 mg/l to about 250 mg/l carbenicillin in solid media, preferably about 75 mg/l to about 200 mg/l, more preferably about 100–125 mg/l. Those of ordinary skill in the art of monocot transformation will recognize that the concentration of antibiotic can be optimized for a particular transformation protocol without undue experimentation.

The resting phase cultures are preferably allowed to rest in the dark or under subdued light, preferably in subdued light. Any of the media known in the art can be utilized for the resting step. The resting/decontamination step may be carried out for as long as is necessary to inhibit the growth of Agrobacterium and to increase the number of transformed cells prior to selection. Typically, the resting/ decontamination step may be carried out for 1 to 6 weeks, preferably 2 to 4 weeks, more preferably 2 to 3 weeks prior to the selection step. In more preferred embodiments, the selection period is started within 3 weeks following co-cultivation. Some strains of Agrobacterium are more antibiotic resistant than are others. For less resistant strains, decontamination is typically performed by adding fresh decontamination medium to the calli every five days or so. For more resistant strains, a stronger antibiotic (e.g., vancomycin) may be added to the calli every other day.

Following the co-cultivation step, or resting/ decontamination step, transformants may be selected and duckweed plants regenerated as described below in Section E.

E. Selection of Transformants and Regeneration of Transformed Duckweed Plants

Duckweed tissue or callus is transformed according to the present invention, for example by ballistic bombardment or Agrobacterium-mediated transformation, each of which is described in more detail above in Sections C and D, respectively. After the transformation step, the transformed tissue is exposed to selective pressure to select for those cells that have received and are expressing the polypeptide from the heterologous nucleic acid introduced by the expression cassette. The agent used to select for transformants will select for preferential growth of cells containing at least one selectable marker insert positioned within the expression cassette and delivered by ballistic bombardment or by the Agrobacterium.

The conditions under which selection for transformants (from any tissue type or callus) is performed are generally the most critical aspect of the methods disclosed herein. The transformation process subjects the cells to stress, and the selection process can be toxic even to transformants. Typically, in response to this concern, the transformed tissue is initially subject to weak selection, utilizing low concentrations of the selection agent and subdued light (e.g., 1–5 $\mu$mol/m$^2$·sec, with a gradual increase in the applied selection gradient by increasing the concentration of the selection agent and/or increasing the light intensity. Selection pressure may be removed altogether for a time and then reapplied if the tissue looks stressed. Additionally, the transformed tissue may be given a "resting" period, as described above in Section D, before any selection pressure is applied at all. The selection medium generally contains a simple carbohydrate, such as 1% to 3% sucrose, so that the cells do not carry out photosynthesis. In addition, the selection is initially performed under subdued light conditions, or even in complete darkness, so as to keep the metabolic activity of the cells at a relatively low level. Those skilled in the art will appreciate that the specific conditions under which selection is performed can be optimized for every species or strain of duckweed and for every tissue type being transformed without undue experimentation.

There is no particular time limit for the selection step. In general, selection will be carried out long enough to kill non-transformants and to allow transformed cells to proliferate at a similar rate to non-transformed cells in order to generate a sufficient callal mass prior to the regeneration step. Thus, the selection period will be longer with cells that proliferate at a slower rate. Type I duckweed callus, for example, proliferates relatively slowly and selection may be carried out for 8–10 weeks prior to regeneration.

Methods of regenerating certain plants from transformed cells and callus are known in the art. See, e.g., Kamo et al., *Bot. Gaz.* 146, 327 (1985); West et al., *The Plant Cell* 5, 1361 (1993); and Duncan et al., *Planta* 165, 322 (1985). Several refinements to these methods are recommended for regenerating duckweed. Frond regeneration following transformation and selection can be achieved most reliably with Type I and Type III callus. Regeneration in Type I calli, for example, can be identified by green centers (sites where fronds are organizing) appearing on the pale yellow callus surface. Typically, duckweed regeneration does not occur under the same medium conditions that support callus proliferation. A lean solid medium (e.g., water-agar or half-strength Schenk and Hildebrandt medium contain 0.5% sucrose and 0.8% agar) is preferred. It is usually necessary, however, to intermittently culture the regenerating duckweed callus for short periods on full-strength medium to maintain nutrient balance in the regenerating cells. In some instances, with slowly regenerating strains or species, this process may have to repeated several times before fronds are regenerated. Typically, plant growth regulators are not added to the frond regeneration medium (because they inhibit the organization of fronds), however, cytokinins, such as BA and adenine sulfate, can increase frond regeneration with some species. Callus cultures do not loose their ability to regenerate fronds over prolonged periods of callus culture.

During the regeneration process, any method known in the art may be utilized to verify that the regenerating plants are, in fact, transformed with the transferred nucleic acid of interest. For example, histochemical staining, ELISA assay, Southern hybridization, Northern hybridization, Western hybridization, PCR, and the like can be used to detect the transferred nucleic acids or protein in the callal tissue and regenerating plants.

Now that it has been demonstrated that duckweed can be transformed utilizing ballistic bombardment and Agrobacterium, alterations to the general methods described herein can be used to increase efficiency or to transform strains that may exhibit some recalcitrance to transformation. Factors that affect the efficiency of transformation include the species of duckweed, the tissue infected, composition of the media for tissue culture, selectable marker genes, the length of any of the above-described step, kinds of vectors, and light/dark conditions. Specifically for Agrobacterium-mediated transformation, the concentration and strain of A. tumefaciens or A. rhizogenes must also be considered. Therefore, these and other factors may be varied to determine what is an optimal transformation protocol for any particular duckweed species or strain. It is recognized that not every species and strain will react the same to the transformation conditions and may require a slightly different modification of the protocols disclosed herein. However, by altering each of the variables, an optimum protocol can be derived for any duckweed line.

The following Examples are offered by way of illustration and not be way of limitation. As used in the Examples, "hr" means hour, "sec" means second, "g" means gram, "mg" means milligram, "l" means liter, "ml" means milliliter, "mmol" means millimole, "mM" means millimolar, "$\mu$M" means micromolar, "m" means meter, "mm" means millimeter, "BA" means benzyladenine, "2,4-D" means 2,4-dichlorophenoxyacetic acid, "NAA" means naphthaleneacetic acid, and "IAA" means indoleacetic acid.

EXAMPLES

Tissue Culture

This section presents experiments pertaining to methods of making duckweed callus. A number of examples use Lemna gibba G3 as the duckweed strain, the strain used to optimize culturing parameters: (1) basal medium formulation, (2) type and concentration of plant growth regulators, and (3) transfer schedule. As knowledge of callus formation increased, it was applied to other duckweed species. The duckweeds make three kinds of callus: (a) a compact, semi-organized callus (designated Type I); (b) a friable, white, undifferentiated callus (designated Type II); and (c) a green, differentiated callus (designated Type III). In tissue culture, callus can only regenerate plants two ways: via embryos and via shoot formation (in duckweed the frond is the shoot). The data presented below demonstrate that transformed duckweed plants can be regenerated from all known pathways of callus regeneration of fronds.

Example 1

Eighteen combinations of an auxin, 2,4-dichlorophenoxyacetic acid (2,4-D), and a cytokinin, benzyladenine (BA), were tested for their effects on callus induction in a duckweed species, Lemna gibba G3.

Duckweed fronds were grown in liquid Hoagland's medium (Hoagland and Snyder, Proc. Amer. Soc. Hort. Sci. 30, 288 (1933)) containing 3% sucrose for two weeks at 23° C. under a 16 hr light/8 hr dark photoperiod with light intensity of approximately 40 $\mu$mol/m$^2$·sec prior to experimentation. For callus induction, eighteen, 100 ml portions of Murashige and Skoog basal medium (Murashige and Skoog, Physiol. Plant. 15, 473 (1962)) containing 3% sucrose, 0.15% Gelrite and 0.4% Difco Bacto-agar were prepared with 2,4-D concentrations of 10, 20 and 50 $\mu$M and BA concentrations of 0, 0.01, 0.1, 1.0, 2.0, and 10.0 $\mu$M. All media were pH adjusted to 5.8, autoclaved at 121° C. for 20 minutes, cooled, and each 100 ml was poured into 4, 100 mm×15 mm petri dishes.

A three 2,4-D concentrations×six BA concentrations, full-factorial experimental design (18 treatments in total) with four replications, with one petri dish per replication and 5 fronds per petri dish was used. For callus induction, 5 individual duckweed fronds were placed abaxial side down on each plate of medium. The 72 plates were incubated at 23° C., for 27 days under a 16 hr light/8 hr dark photoperiod with light intensity of approximately 40 $\mu$mol/m$^2$·sec. After 27 days the duckweed tissue was transferred to fresh media of the same type and incubation was continued another 35 days under the same temperature and light culturing conditions.

The results, measured as the frequency of callus induction (#fronds making any callus/total # fronds) showed three types of callus proliferation after the 62 days of incubation. (1) A compact, white-yellow callus was identified and designated as "Type I". A low frequency of fronds, approximately 5%, proliferated this type of callus. (2) A friable white callus was identified and designated as "Type II". Between 20 and 40% of fronds proliferated this type of callus. (3) A green callus ranging in its degree of cellular organization was identified and designated as "Type III". This callus type was produced by greater than 50% of all fronds proliferated during the incubation time. All three types of callus demonstrated proliferation at all 18 2,4-D and BA combinations in varying frequencies. Callus proliferation was the most vigorous in a broad range of 2,4-D concentrations, from 20–50 $\mu$M, and BA concentrations between 0.01 and 0.1 $\mu$M.

Example 2

Forty concentrations of an auxin, 2,4-dichlorophenoxyaectic acid (2,4-D), and a cytokinin, benzyladenine (BA) were tested to better optimize the auxin and cytokinin concentrations for callus induction from duckweed fronds of Lemna gibba G3.

Duckweed fronds were grown in liquid Hoagland's medium containing 3% sucrose for two weeks at 23° C. under a 16 hr light/8 hr dark photoperiod with light intensity of approximately 40 $\mu$mol/m$^2$·sec. prior to experimentation. For callus induction, forty 100 ml portions of Murashige and Skoog medium with 3% sucrose, 0.15% Gelrite, and 0.4% Difco Bacto-agar were prepared with 2,4-D concentrations of 20, 30, 40, 50, 60, 70, 80, 100 $\mu$M and BA concentrations of 0.01, 0.05, 0.1, 0.5, and 1.0 $\mu$M. All media were pH adjusted to 5.8, autoclaved at 121° C. for 20 minutes, cooled, and each 100 ml was poured into 4, 100 mm×15 mm petri dishes.

An eight 2,4-D concentrations×five BA concentrations, full-factorial experimental design (40 treatments in total)

with four replications, with one petri dish per replication and 5 fronds per petri dish was used. For callus induction, 5 individual duckweed fronds were placed abaxial side down on each plate of medium. The plates were incubated at 23° C., for 27 days under a 16 hr light/8 hr dark photoperiod with light intensity of approximately 40 $\mu$mol/m$^2$·sec. After 27 days, the duckweed tissue was transferred to fresh media of the same type and incubation was continued another 35 days under the same temperature and light culturing conditions.

Results taken after 63 days of incubation showed that three types of callus had proliferated: (1) Type I, (2) Type II, and (3) a Type III callus. Regression analysis (quadratic response surface) of the numerical frequency data (#fronds making any callus/total # fronds) revealed differences in frond response for callus induction of the different types. The frequencies of Type II and Type III callus types were significantly affected by the concentrations of both 2,4-D and BA, however, the frequency of Type I callus was significantly affected by the 2,4-D concentration only. No specific concentration of 2,4-D or BA proved optimal, callus induction occurred over a broad range of both plant growth regulators. Approximately 50% of the fronds produced Type III callus, approximately 25% produced Type II callus, and less than 5% produced Type I callus.

Example 3

Forty combinations of an auxin, dicamba, and a cytokinin, benzyladenine (BA), were tested to compare the relative efficacy of dicamba versus 2,4-D for callus induction in a duckweed species, Lemna gibba G3.

Duckweed fronds were grown in liquid Hoagland's medium containing 3% sucrose for two weeks at 23° C. under a 16 hr light/8 hr dark photoperiod with light intensity of approximately 40 $\mu$mol/m$^2$·sec. prior to experimentation. For callus induction, forty 100 ml portions of Murashige and Skoog medium with 3% sucrose, 0.15% Gelrite, and 0.4% Difco Bacto-agar were prepared with dicamba concentrations of 10, 20, 30, 40, 50, 60, 80, 100 $\mu$M and BA concentrations of 0.01, 0.05, 0.1, 0.5, and 1.0 $\mu$M. All media were pH adjusted to 5.8, autoclaved at 121° C. for 20 minutes, cooled, and each 100 ml was poured into 4, 100 mm×15 mm petri dishes.

An eight dicamba concentrations×five BA concentrations, full-factorial experimental design (40 treatments in total) with four replications, with one petri dish per replication and 5 fronds per petri dish was used. For callus induction, 5 individual duckweed fronds were placed abaxial side down on each plate of medium. The plates were incubated at 23° C., for 27 days under a 16 hr light/8 hr dark photoperiod with light intensity of approximately 40 $\mu$mol/m$^2$·sec. After 28 days the duckweed tissue was transferred to fresh media of the same type and incubation was continued another 45 days under the same temperature and light culturing conditions.

After 73 days of incubation three types of callus proliferation were observed: (1) Type I, (2) Type II, and (3) a Type III callus. Overall, callus proliferation was poor and occurred on dicamba concentrations of 10 and 20 $\mu$M; above 30 $\mu$M callus proliferation did not occur. Type II and Type III callus proliferated in response to dicamba; Type I callus proliferation was rare.

Example 4

Two concentrations of 2,4-D in combination with BA were used determine if callus growth could be maintained and callus lines established from the three types observed with Lemna gibba G3.

Duckweed fronds were grown in liquid Schenk and Hildebrandt medium (Schenk and Hildebrandt, Can. J. Bot. 50, 199 (1972)) containing 1% sucrose for two weeks at 23° C. under a 16 hr light/8 hr dark photoperiod with light intensity of approximately 40 $\mu$mol/m$^2$·sec. prior to experimentation. For callus induction, 400 ml of Murashige and Skoog medium with 3% sucrose, 0.15% Gelrite, 0.4% Difco Bacto-agar, 0.01 $\mu$M BA were prepared with 2,4-D concentrations of 10 and 40 $\mu$M. All media were pH adjusted to 5.8, autoclaved at 121° C. for 20 minutes, cooled, and each 200 ml portion was poured into 8, 100 mm×15 mm petri dishes.

A two treatment, random block experimental design with four replications, with one petri dish per replication and 5 fronds per petri dish was used. For callus induction, 5 individual duckweed fronds were placed abaxial side down on each plate of medium. The plates were incubated at 23° C., for 27 days under a 16 hr light/8 hr dark photoperiod with light intensity of approximately 40 $\mu$mol/m$^2$·sec. After 4 weeks, the duckweed tissue was transferred to fresh media of the same type and incubation was continued another 4 weeks under the same temperature and light culturing conditions.

After 8 weeks of incubation three types of callus proliferation were observed: (1) Type I, (2) Type II, and (3) a Type III callus. All three callus types were transferred to fresh medium of identical composition from that they had been on, and incubation on identical culturing conditions was continued with four week subcultures. After two more months of culture, Type I and Type III callus on 10 $\mu$M 2,4-D and 0.01 $\mu$M BA established healthy, proliferating callus cultures. Type II callus did not proliferate. Although callus proliferation could be maintained on a four-week subculture schedule, callus decline was noted during the third and fourth weeks of the subculture period.

Example 5

The subculture schedule to maintain callus proliferation was tested with Lemna gibba G3. Duckweed fronds were grown in liquid Schenk and Hildebrandt medium containing 1% sucrose for two weeks at 23° C. under a 16 hr light/8 hr dark photoperiod with light intensity of approximately 40 $\mu$mol/m$^2$·sec prior to experimentation. For callus induction, 500 ml of Murashige and Skoog medium with 3% sucrose, 0.15% Gelrite, and 0.4% Difco Bacto-agar, 30 $\mu$M 2,4-D and 0.02 $\mu$M BA was prepared, the pH adjusted to 5.8, autoclaved at 121° C. for 30 minutes, cooled, and poured into 20, 100 mm×15 mm petri dishes.

A two treatment, random block experimental design with two replications, with five petri dish per replication and 5 fronds per petri dish was used. For callus induction, 5 individual duckweed fronds were placed abaxial side down on each plate of medium. The plates were incubated at 23° C., for 2 weeks under a 16 hr light/8 hr dark photoperiod with light intensity of approximately 40 $\mu$mol/m$^2$·sec. After 2 weeks, the duckweed tissue on half the plates (10 plates) was transferred to fresh medium of the same composition and incubation was continued under the same conditions as those of the non-transferred tissue. After 4 weeks the tissue was assessed for callus proliferation. Three types of callus proliferated: Type I, Type II, and Type III. No difference in callus type or proliferation was observed between duckweed tissue transferred at 2 weeks as compared with duckweed tissue incubated for 4 weeks without transfer.

Type I and Type III callus were subcultured away from the original fronds and continued in culture on Murashige and Skoog medium with 3% sucrose, 0.15% Gelrite, 0.4% Difco Bacto-agar, 10 μM 2,4-D and 0.01 μM BA. Proliferating callus was continually subcultured to fresh medium of the same composition at 2 week intervals. Longer intervals between transfer resulted in an abrupt decline in callus health between 2 and 3 weeks. Callus proliferation continued without loss of vigor when a two-week subculture schedule was maintained.

Example 6

Two different basal media, Murashige and Skoog and Nitsch and Nitsch (*Science* 163, 85 (1969)), were tested to compare their relative efficacy for callus induction of *Lemna gibba* G3.

Duckweed fronds were grown in liquid Schenk and Hildebrandt medium containing 1% sucrose for two weeks at 23° C. under a 16 hr light/8 hr dark photoperiod with light intensity of approximately 40 μmol/m$^2$·sec prior to experimentation. For callus induction, 500 ml, each, of Murashige and Skoog and Nitsch and Nitsch media with 3% sucrose, 0.15% Gelrite, 0.4% Difco Bacto-agar, 30 μM 2,4-D, and 0.01 μM BA were prepared, the pH adjusted to 5.8, autoclaved at 121° C. for 30 minutes, cooled, and each used to pour 20, 100 mm×15 mm petri dishes.

A two treatment, random block experimental design with two replications, with five petri dishes per replication and 5 fronds per petri dish was used. For callus induction, 5 individual duckweed fronds were placed abaxial side down on each plate of medium. The plates were incubated at 23° C., for 2 weeks under a 16 hr light/8 hr dark photoperiod with light intensity of approximately 40 μmol/m$^2$·sec. After 2 weeks, the duckweed tissue was transferred to fresh medium of the same composition and incubation was continued under the same conditions.

After 4 weeks the tissue on all the plates was assessed for callus proliferation. Fronds cultured on Nitsch and Nitsch medium failed to proliferate significant amounts of callus. Duckweed tissue on this medium was pale and had begun to yellow. Duckweed fronds cultured on Murashige and Skoog medium proliferated the usual three types of callus: Type I, Type II, and Type III callus.

Type I and Type III callus were subcultured away from the original fronds and continued in culture on Murashige and Skoog medium with 3% sucrose, 0.15% Gelrite, 0.4% Difco Bacto-agar, 10 μM 2,4-D and 0.01 μM BA. Proliferating callus was continually subcultured to fresh medium of the same composition at two-week intervals. Longer intervals between transfer resulted in an abrupt decline in callus health between 2 and 3 weeks. Callus proliferation continued without loss of vigor.

Example 7

Three different basal media, Murashige and Skoog, Schenk and Hildebrandt, and Gamborg's B5 (Gamborg et al., *In Vitro* 12, 473 (1976)) were tested to compare their relative efficacy for callus induction and growth of *Lemna gibba* G3.

Duckweed fronds were grown in liquid Schenk and Hildebrandt medium containing 1% sucrose for two weeks at 23° C. under a 16 hr light/8 hr dark photoperiod with light intensity of approximately 40 μmol/m$^2$·sec prior to experimentation. For callus induction, 500 ml, each, of the three media were prepared with 3% sucrose, 0.15% Gelrite, 0.4% Difco Bacto-agar, 30 μM 2,4-D and 0.02 μM BA, the pH adjusted to 5.8, and autoclaved at 121° C. for 30 minutes, cooled, and each portion was used to pour 20, 100 mm×15 mm petri dishes.

A three treatment, random block experimental design with two replications, with five petri dishes per replication and 5 fronds per petri dish was used. For callus induction, 5 individual duckweed fronds were placed abaxial side down on each plate of medium. The plates were incubated at 23° C., for 2 weeks under a 16 hr light/8 hr dark photoperiod with light intensity of approximately 40 μmol/m$^2$·sec. After 2 weeks, the duckweed tissue was transferred to fresh medium of the same composition and incubation was continued under the same conditions.

After 4 weeks the tissue on all the plates was assessed for callus proliferation. Fronds cultured on Gamborg's B5 medium were pale, and yellow senescent fronds were present. No appreciable callus proliferation had occurred. Fronds cultured on Schenk and Hildebrandt medium were dark green and proliferated aberrant fronds, and no appreciable callus proliferation had occurred. Duckweed fronds cultured on Murashige and Skoog medium proliferated the three usual types of callus: Type I, Type II and Type III callus.

Type I and Type III callus were subcultured away from the original fronds and continued in culture on Murashige and Skoog medium with 3% sucrose, 0.15% Gelrite, 0.4% Difco Bacto-agar, 10 μM 2,4-D and 0.01 μM BA. Proliferating callus was continually subcultured to fresh medium of the same composition at two-week intervals. Longer intervals between transfer resulted in an abrupt decline in callus health between 2 and 3 weeks. Callus proliferation continued without loss of vigor.

Example 8

Four basal media: Murashige and Skoog (MS), Schenk and Hildebrandt (SH), Nitsch and Nitsch (NN), and Gamborg's B5 (B5), were used to compare their efficacy to support *Lemna gibba* G3 Type II callus proliferation in liquid medium.

Duckweed fronds were grown in liquid Schenk and Hildebrandt medium containing 1% sucrose for two weeks at 23° C. under a 16 hr light/8 hr dark photoperiod with light intensity of approximately 40 μmol/m$^2$·sec prior to experimentation. For callus induction, 500 ml of Murashige and Skoog medium was prepared with 3% sucrose, 0.15% Gelrite, 0.4% Difco Bacto-agar, 30 μM 2,4-D and 0.02 μM BA, the pH adjusted to 5.8, and autoclaved at 121° C. for 30 minutes, cooled, and poured into 20, 100 mm×15 mm petri dishes.

For callus induction, 5 individual duckweed fronds were placed abaxial side down on each plate of medium. The 20 plates were incubated at 23° C., for 2 weeks under a 16 hr light/8 hr dark photoperiod with light intensity of approximately 40 μmol/m$^2$·sec. After 2 weeks, the duckweed tissue was transferred to fresh medium of the same composition and incubation was continued under the same conditions.

After 4 weeks Type II callus tissue was used to inoculate liquid medium for callus suspension cultures. For suspension callus establishment, 100 ml, each, of the four basal media, MS, SH, NN, and B5, were prepared with 3% sucrose, 10 μM 2,4-D, and 0.01 μM BA. The media were adjusted to pH 5.8, four 25 ml aliquots were placed in 125 ml flasks, and all 16 flasks of media were autoclaved at 121° C. for 18 minutes. After cooling, each flask was inoculated with 1–2 small pieces of Type II, friable white callus. The flasks were wrapped with aluminum foil and incubated 23° C., for 2 weeks, with constant shaking at 100 rpm, in the dark.

After two weeks the flasks were assessed for callus proliferation. A slight amount of growth was noted with Murashige and Skoog medium and with Nitsch and Nitsch medium. The flasks were incubated for another 2 weeks without change of medium and no further callus proliferation was noted.

Example 9

Thirty-two duckweed strains across 15 species, broadly representative of the genetic diversity of the Lemnaceae, were used to determine the degree to which the methods and media for callus induction developed with *Lemna gibba* G3 will extrapolate across the entire family. Table I lists the strains tested.

Duckweed fronds were grown in liquid Schenk and Hildebrandt medium containing 1% sucrose for two weeks at 23° C. under a 16 hr light/8 hr dark photoperiod with light intensity of approximately 40 $\mu$mol/m$^2$·sec prior to experimentation. For callus induction, six basal media were used: Murashige and Skoog, Schenk and Hildebrand (Schenk and Hildebrandt, *Can. J. Bot.* 50, 199 (1972)), Nitsch and Nitsch, N6 (Chu et al., *Scientia Sinica* 18, 659 (1975)), Gamborg's B5, and Hoagland's. The two plant growth regulator combinations known to elicit callus proliferation in *L. gibba* G3 were used: 30 $\mu$M 2,4-D and 0.02 $\mu$M BA, and 5 $\mu$M 2,4-D and 2 $\mu$M BA. For each strain, 200 ml of each basal medium was prepared with 3% sucrose, 0.15% Gelrite, and 0.4% Difco Bacto-agar. The 200 ml was divided into 2, 100 ml portions, each to be used to prepare the two plant growth regulator concentrations. The pH of all media was adjusted to 5.8, the media were autoclaved for 30 minutes at 121° C., cooled and 4, 100 mm×15 mm petri dishes were poured from each 100 ml portion.

A 6 media×2 plant growth regulator combinations, 12 treatment, random block experimental design was used for each duckweed strain tested. The design was replicated four times, with one petri dishes per replication and 6 fronds per petri dish. For callus induction, 6 individual duckweed fronds were placed abaxial side down on each plate of medium for the larger fronds of Lemna, Spirodela and Wolfiella species. For strains within Wolffia, the small fronds technically prohibited plating of individual fronds, rather, small clumps of fronds were used as the experimental unit. The plates were incubated at 23° C., for 4–5 weeks under a 16 hr light/8 hr dark photoperiod with light intensity of approximately 40 $\mu$mol/m$^2$·sec. At this time the fronds were evaluated for general health (judged by color: green to yellow, and vigor of proliferation) and the frequency of callus initiation of the three types: Type I, Type II, and Type III.

The results showed a variation in responsiveness of the different duckweed species to callus induction medium. In general, species and strains in the genera Lemna and Wolffia were the most responsive. All five *Lemna gibba* strains showed callus induction to varying degrees on MS, B5, and N6 medium containing 5 $\mu$M 2,4-D and 2 $\mu$M BA. Both Lemna minor strains followed the same pattern, with a greater degree of callus induction relative to the *Lemna gibba* strains. Both *Lemna miniscula* strains showed a high frequency of callus induction, with proliferation of a white callus somewhat dissimilar to *Lemna minor* or *Lemna gibba*. *Lemna aequinoctialis* showed frond curling and swelling at the highest auxin concentrations, but the proliferation of a true callus culture was not observed, indicating that the auxin concentrations used were not high enough. *Lemna valdiviana* did not show callus induction. In the Wolffia species, *Wolffia arrhiza* showed a small amount of callus proliferation on B5 medium with 5 $\mu$M 2,4-D and 2 $\mu$M BA. *Wolffia brasiliensis* and *Wolffia columbinana* showed callus induction on Hoaglands medium supplemented with 5 $\mu$M 2,4-D and 2 $\mu$M BA. The remaining Wolffia species, *Wolffia australiana,* did not show callus induction, although fronds showed swelling and somewhat abnormal growth. The Wolffiella and Spirodela species did not show callus induction. Fronds of the Spirodela species did not survive on the higher concentration of 2,4-D and did not grow well at the lower concentration. This pattern of response is consistent with the interpretation that Spirodela is more sensitive to auxin than the Lemna and Wolffia species and that lower auxin concentrations should be used in subsequent experiments to induce callus formation.

TABLE I

| Genus | Species | Strain Designation | Country of Origin |
|---|---|---|---|
| Spirodela | polyrrhiza | 7970 | USA |
| | | 4240 | China |
| | | 8652 | China |
| | | 8683 | Kenya |
| Spirodela | punctata | 7488 | USA |
| | | 7776 | Australia |
| Spirodela | intermedia | 7178 | |
| Wolffia | arrhiza | 7246 | S. Africa |
| | | 9006 | Japan |
| Wolffia | australiana | 7267 | Tasmania |
| | | 7317 | Australia |
| Wolffia | brasiliensis | 7397 | Venezuela |
| | | 7581 | Venezuela |
| | | 8919 | Venezuela |
| Wolffia | columbiana | 7153 | USA |
| | | 7918 | USA |
| Wolffiella | lingulata | 8742 | Argentina |
| | | 9137 | Brazil |
| Wolfiella | neotropica | 7279 | Brazil |
| | | 8848 | Brazil |
| Wolfiella | oblongata | 8031 | USA |
| | | 8751 | Argentina |
| Lemna | aequinoctialis | 7558 | USA |
| Lemna | gibba | G3 | USA |
| | | 6861 | Italy |
| | | 7784 | |
| | | 8405 | France |
| | | 8678 | Kashmir |
| Lemna | minor | 8744 | Albania |
| | | 8627 | Denmark |
| Lemna | miniscula | 6600 | California |
| | | 6747 | California |
| Lemna | valdiviana | 8821 | Argentina |
| | | 8829 | Argentina |

Example 10

Four auxins, napthaleneacetic acid (NAA), 2,4-D, indolebutyric acid (IBA), and dicamba were tested for their ability to induce callus formation from *L. gibba* G3 fronds on three different basal media: SH, MS and N6.

Duckweed fronds were grown in liquid Schenk and Hildebrandt medium containing 1% sucrose for two weeks at 23° C. under a 16 hr light/8 hr dark photoperiod with light intensity of approximately 40 $\mu$mol/m$^2$·sec prior to experimentation. For callus induction, three basal media were tested: Murashige and Skoog, Schenk and Hildebrandt, and N6. Benzyladenine was used as the cytokinin at a concentration of 1 $\mu$M. The auxin concentrations varied with auxin type. For the relatively strong auxins, 2,4-D and dicamba, concentrations were 0, 1, 5, 10 and 20 $\mu$M. For weak auxins, NAA and IBA, the concentrations were 0, 5, 10, 20 and 50 $\mu$M. For each medium dose-response experiment, 2 liters of basal medium were prepared with BA and the pH adjusted to 5.8. The volume was aliquoted as 20, 100 ml portions. To each of these portions, the appropriate amount of auxin was added and the medium was adjusted to 0.15% Gelrite, and 0.4% Difco Bacto-agar. The media were autoclaved for 30 minutes at 121° C., cooled and 4, 100 mm×15 mm petri dishes were poured from each 100 ml portion.

A 3 media×4 auxin×5 concentration combinations, 60 treatment, randomized dose-response experimental design was used. The design was replicated two times, with one petri dish per replication and 5 fronds per petri dish. For callus induction, 5 individual duckweed fronds were placed abaxial side down on each plate of medium. The plates were incubated for five weeks at 23° C. under a 16 hr light/8 hr dark photoperiod with light intensity of approximately 40 $\mu$mol/m$^2$·sec. After five weeks, the fresh weight of duckweed tissue arising from each original frond was measured and these tissue populations were visually examined for the number of calli induced and the type of callus produced.

A number of trends were seen in the results. First, low auxin concentrations and weak auxins promote frond proliferation. This proliferation is greater than that seen without auxin present. When fronds are proliferating, callus induction frequency is low. At high auxin concentration or with stronger auxins, frond curling and greatly reduced proliferation was observed. Callus formation was associated with frond curling. The auxin types ranked (from most curling to least curling) as follows: 2,4-D, dicamba, NAA and IBA. Both N6 and MS supported callus formation, SH did not. N6 supported greater proliferation than MS. Higher concentrations of auxin were required on N6 to elicit callus formation than on MS medium. For compact, Type I callus induction, 2,4-D, dicamba, and NAA all showed some degree of callus induction on MS medium, on N6 medium only 2,4-D and dicamba produced callus. The greatest callus induction was seen on MS medium containing 10 $\mu$M NAA.

Example 11

Four cytokinins: benzyladenine (BA), kinetin, thidiazuron (TDZ), and 2-iP were tested for their ability to induce callus formation from *L. gibba* G3 fronds on three different basal media: SH, MS and N6.

Duckweed fronds were grown in liquid Schenk and Hildebrandt medium containing 1% sucrose for two weeks at 23° C. under a 16 hr light/8 hr dark photoperiod with light intensity of approximately 40 $\mu$mol/m$^2$·sec prior to experimentation. For callus induction, three basal media were tested: Murashige and Skoog, Schenk and Hildebrandt, and N6. 2,4-D was used as the auxin at a concentration of 20 $\mu$M. The cytokinin concentrations used were 0, 0.05, 0.1, 0.5, 1 and 5 $\mu$M. For each medium dose-response experiment, 2400 ml of basal medium were prepared with 2,4-D and the pH adjusted to 5.8. The volume was aliquoted as 24, 100 ml portions. To each of these portions, the appropriate amount of cytokinin was added and the medium was adjusted to 0.15% Gelrite, and 0.4% Difco Bacto-agar. The media were autoclaved for 30 minutes at 121° C., cooled and 4, 100 mm×15 mm petri dishes were poured from each 100 ml portion.

A 3 media×4 cytokinin types×6 cytokinin concentrations combinations, 72 treatment, randomized dose-response experimental design was used. The design was replicated two times, with one petri dish per replication and 5 fronds per petri dish. For callus induction, 5 individual duckweed fronds were placed abaxial side down on each plate of medium. The plates were incubated for five weeks at 23° C. under a 16 hr light/8 hr dark photoperiod with light intensity of approximately 40 $\mu$mol/m$^2$·sec. After five weeks, the fresh weight of duckweed tissue arising from each original frond was measured and these tissue populations were visually examined for the number of calli induced and the type of callus produced.

A number of trends were seen in the results. Frond proliferation did not occur across all treatments due to the 2,4-D concentration of 20 $\mu$M being too high. Frond curling was evident across all treatments. MS and N6 showed callus induction with MS clearly superior. Callus induction did not occur on SH medium. TDZ gave the greatest frequency of callus induction on MS medium across a broad range of concentrations. A trade-off exists between induction of Type I and Type II callus. When Type I callus induction is high, Type II callus induction is low.

Example 12

As *Lemna minor* strains 8744 and 8627 showed greater callus induction and more rapid callus proliferation than *L. gibba* strains (see Example 9 and Table I), further optimization of culturing conditions was done for *L. minor*. Variables tested for callus induction included: a) screening of basal medium composition, b) auxin type and concentration screening, and c) cytokinin type and concentration screening.

In the basal medium screen, three media were tested: Schenck and Hildebrandt, Murashige and Skoog, and F medium as developed by Frick (Frick, (1991) *J. Plant Physiol.* 137:397–401). Stock fronds used for these experiments were grown on F-medium supplemented with 24 $\mu$M 2,4-D and 2 $\mu$M 2 iP for two weeks prior to use. Callus induction media were prepared as in Example 8. Fronds were separated, the roots cut off, and half were forced through a strainer (following the method of Frick) prior to placement on callus induction media, the remaining half of the fronds were plated whole. The fronds were incubated under conditions given in Example 8 for 6 weeks at which time cultures were evaluated for the presence or absence of callus induction, the degree to which the callus proliferated, and the basic morphology of the callus.

Murashige and Skoog medium showed the best callus induction with both *L. minor* strains. Schenk and Hildebrandt medium failed to produce callus, and callus induction was minimal on F medium. Forcing fronds through a sieve prior to plating had no effect on callus induction.

In the auxin type and concentration experiment, four auxins: 2,4-D, NAA, IBA and dicamba were tested, each at four concentrations: 2, 5, 10 and 20 $\mu$M, for their ability to induce callus formation from *L. minor* strains 8744 and 8627. The basal medium used was MS and media and experimental protocol was basically that followed in Example 10. Fronds used in this experiment were grown for 2 weeks prior to plating on callus induction medium under 3 different culture conditions: 1) SH medium without plant growth regulators, 2) F medium with 24 $\mu$M 2,4-D and 2 $\mu$M 2-iP, and 3) SH medium with 24 $\mu$M 2,4-D and 2 $\mu$M 2-iP. Fronds were separated, the roots cut off and then plated on induction medium. The fronds were incubated under conditions given in Example 8 for 6 weeks at which time cultures were evaluated for the presence or absence of callus induction, the degree to which the callus proliferated, and the basic morphology of the callus present.

Callus induction was not observed on any treatment in which the inducing auxin was either NAA or IBA. For strain 8744, prolific callus induction was observed in 2,4-D treatments of either 5 or 10 $\mu$M concentrations, with 5 $\mu$M 2,4-D giving the best induction. Callus induction was also observed at the highest dicamba concentration, 20 $\mu$M. For L. minor strain 8627, callus induction was also observed on 2,4-D and dicamba, but at lower concentrations. For 2,4-D, the most prolific callus induction was observed at 1 and 5 µM, with 5 µM giving the best induction. Useful concentrations of dicamba for callus induction were 5 and 10 µM. Regardless of callus induction treatment, callus formation came only from fronds previously grown on Schenk and Hildebrandt medium without plant growth regulators.

In the cytokinin type and concentration experiment, four cytokinins: BA, kinetin, 2-iP, and thidiazuron were tested, each at five concentrations: 0.05, 0.1, 0.5, 1 and 5 µM, for their ability to induce callus formation from L. minor strains 8744 and 8627. The basal medium used was MS and the media and experimental protocol were basically as described in Example 11. Fronds used in this experiment were grown for 2 weeks prior to plating on callus induction medium under 3 different culture conditions: 1) SH medium without plant growth regulators, 2) F medium with 24 µM 2,4-D and 2 µM 2-iP, and 3) SH medium with 24 µM 2,4-D and 2 µM 2-iP. Fronds were separated, the roots cut off and then plated on induction medium. The fronds were incubated under conditions given in Example 8 for 6 weeks at which time cultures were evaluated for the presence or absence of callus induction, the degree to which the callus proliferated, and the basic morphology of the callus.

For strain 8744, prolific callus induction was observed with either 2-iP or thidiazuron, each at either 0.5 or 1 µM. Callus induction was only observed with fronds grown on F-medium prior to plating on callus induction medium. For L. minor strain 8627, callus induction was also observed with either 2-iP or thidiazuron but at lower concentrations: either 0.1 or 0.5 µM. In this strain, callus induction was also observed using BA at 0.5 and at 1 µM.

Example 13

Basal medium composition was tested for its effect on callus proliferation and long term establishment using L. minor strains 8627 and 8644.

Three basal medium compositions were tested for their ability to maintain healthy callus growth: MS, F-medium and half-strength SH. All media contained 3% sucrose and were gelled with 0.4% Difco Bacto-agar and 0.15% Gelrite. The MS medium was supplemented with 1 µM 2,4-D, 2 µM BA; the half-strength SH medium was supplemented with 1 µM BA; and the F-medium was supplemented with 9 µM 2,4-D and 1 µM 2-iP. Callus cultures from both strain 8744 and strain 8627 proliferated in a previous callus induction medium as in Example 12 were used for this experiment. Callus was grown for a two-week subculture period and scored for growth, color and general health.

For L. minor strain 8744, half-strength SH supplemented with 1 µM BA proved the best for maintaining callus growth and health, with the resulting callus showing areas of organizations and aberrant frond regeneration. Sectors of color, ranging from green to pale yellow were also present on this medium. Culturing callus on MS or F-medium resulted in very fast proliferation, with fresh weight doubling every 6 days. Callus proliferated on these two media showed much less organization and frond regeneration. For strain 8627, there was little effect of basal media, callus proliferation was equally good on all 3 media. As with strain 8744, callus showed more organization when grown on half-strength SH supplemented with 1 µM BA.

Example 14

As Lemna minor showed greater callus induction than Lemna gibba, an additional screening of three more L. minor strains, all exceptional in frond growth rate and protein content, was done to determine if the protocol for callus induction from L. minor 8744 and 8627 would extrapolate to these new strains. The strains are were designated as L. minor 7501, 8626, and 8745.

The callus induction system developed in the previous Examples was followed: Murashige and Skoog basal medium supplemented with 3% sucrose, 5 µM 2,4-D and 2 µM BA, and gelled with 0.4% Difco Bacto-agar and 0.15% Gelrite was used for callus induction. Fronds were grown on liquid SH medium devoid of plant growth regulators and supplemented with 1% sucrose prior to plating on callus induction medium. Fronds were plated onto callus induction medium and scored 5 weeks later for relative frequencies of callus induction and relative rates of callus proliferation.

For strains 8626 and 8745 callus induction did not occur during the 5-week induction period, however subsequent culture did yield a low frequency of callus proliferation. The morphology and color of callus from strains 8626 and 8745 was quite similar to that proliferated from 8744 and 8627 and proliferated quite well when transferred to callus maintenance medium. Strain 7501 showed a low frequency of callus induction, with callus similar in morphology to that produced from strains 8626 and 8745.

Example 15

As Lemna minuscula showed significant callus induction on the first screening (see Example 9), callus induction was repeated with Lemna miniscula strains 6600 and 6747. Callus induction medium was prepared and fronds cultured as described in Example 14.

Both Lemna miniscula strains, 6600 and 6747, showed very high frequencies of callus induction, with callus proliferating from virtually every frond. Callus initiation occurred quickly in these strains with callus first observed 2–3 weeks after plating. Callus was pale in color and proliferated more slowly than that produced from Lemna minor strains 8744 or 8627 (see Example 14).

Example 16

Based on the investigations described in the previous Examples, the preferred methods for callus induction and growth in Lemna are as follows.

Callus induction, growth and frond regeneration from duckweed plants is accomplished through incubation on the appropriate medium and manipulation of the plant growth regulator types and concentrations at specific developmental stages to promote callus formation, growth and reorganization to fully differentiated plants. Typically, for species within the genus Lemna, the preferred media for callus induction are N6 and MS, most preferred is MS. Fronds are incubated in the presence of both an auxin and a cytokinin, the preferred auxins are NAA and 2,4-D and the preferred cytokinins are BA and TDZ. The concentrations of these plant growth regulators vary over a broad range. For the auxins, the preferred concentrations are 5–20 µM, the most preferred are 5–10 µM, and for the cytokinins, the preferred concentrations are 0.5–5 µM, the most preferred are 0.5–1 µM. The fronds are incubated for an induction period of 3–5 weeks on medium containing both plant growth regulators with callus proliferating during this time.

For callus growth, the preferred media are as for callus induction, but the auxin concentration is reduced. For auxins, the preferred concentrations are 1–5 µM, and for cytokinins the preferred concentrations are 0.5–1 µM. The subculture period is also reduced from 4–5 weeks, for callus induction, to 2 weeks for long-term callus growth. Callus growth can be maintained on either solid medium gelled with agar, Gelrite, or a combination of the two, with the preferred combination of 0.4% Difco Bacto-agar and 0.15% Gelrite, or on liquid medium. Callus cultures can be maintained in a healthy state for indefinite periods of time using this method.

Example 17

Strains within Wolffia respond to callus-inducing plant growth regulator concentrations in a manner similar to that for strains within Lemna. Therefore, select Wolffia strains were further investigated for their ability to proliferate callus.

Four *Wolffia arrhiza* strains: 7246, 8853, 9000, 9006 and four *Wolffia brasiliensis* strains: 7393, 7581, 7591, and 8319 were tested for their ability to proliferate callus in response to plant growth regulators. The basal medium used was MS supplemented with 3% sucrose, 5 μM 2,4-D, 5 μM, each BA and kinetin, and 65 μM phenylboric acid. Cultures were plated and incubated on callus induction medium for 5 weeks then scored for callus proliferation.

Callus proliferation was not obtained during the 5-week incubation period from any of the strains tested. However, pre-callus induction morphology was readily apparent in several strains, including *Wolffia arrhiza* 8853, 9000, 9006 and *Wolffia brasilensis* 7581. With these strains, frond thickening was apparent, a response frequently seen in fronds before callus formation becomes apparent and indicates that the auxin concentrations used was insufficient to support callus proliferation.

Transformation

This section covers experiments pertaining to the methods used for actual gene transfer. There are three sections: (1) Transformation of fronds using the gene gun, (2) Agrobacterium-mediated transformation using duckweed fronds, and (3) Agrobacterium-mediated transformation using duckweed callus. The transformation of fronds experiments were used to optimize the parameters affecting actual gene transfer: (a) bacterial growth, (b) inclusion of acetosyringone, (c) bacterial concentration, (d) solution for resuspending bacteria and the effect of osmotic shock, (e) co-cultivation medium for fronds and callus, (f) duration of the time of inoculation, (g) co-cultivation time for fronds and callus, and (h) light conditions during co-cultivation. The protocol developed with fronds was applied to transform the callus cultures obtained using the optimized tissue culture procedure. It is this transformed callus that is taken on to selection and then through regeneration to obtain transformed fronds.

Gene Gun Mediated Transformation

Example 18

Fronds of *Lemna gibba* G3 were subjected to microcarrier bombardment to test their ability to express foreign gene constructs.

For frond proliferation, 60 ml of high salt medium (De Fossard, TISSUE CULTURE FOR PLANT PROPAGATORS 132–52 (1976)) supplemented with 3% sucrose and 0.8% agar was prepared, the pH adjusted to 5.8, autoclaved for 20 minutes at 121° C., cooled, and used to pour 6, 60 mm×15 mm petri dishes. One frond was inoculated to each petri dish. The fronds were grown for two weeks at 23° C. under a 16 hr light/8 hr dark photoperiod with light intensity of approximately 40 μmol/m²·sec.

For bombardment, 1.6 μm gold microcarriers were prepared and DNA from plasmid pRT99 was precipitated on the microcarriers following the manufacturer's (Bio-Rad) gene gun protocols. The plasmid, pRT99 (Topfer et al., *Nucleic Acid Res.* 16, 8725 (1988)) encodes the neomycin phosphotransferase gene and the β-glucuronidase gene (GUS; Jefferson et al., *EMBO J.* 6, 3901 (1987)), both under the control of CaMV35S promoters.

Duckweed fronds were turned abaxial side up and bombarded with the DNA coated microcarriers at four pressure levels of helium: 800, 600, and 400 lbs/sq. inch. Histochemical staining for GUS activity using 5-bromo-4-chloro-3-indolyl-β-D-glucuronic acid (X-gluc) as the substrate following the method of Stomp (*Histochemical localization of beta-glucoronidase,* in GUS PROTOCOLS 103–114 (S. R. Gallagher ed. 1991)) was done 24 hours after bombardment. The frequency of GUS positive staining centers was directly proportional to the pressure used for bombardment, with the greatest number of GUS expressing cells found in the 800 psi treatment, with frequency ranging from 4–20 staining cells/frond. In all treatments, bombardment resulted in the destruction of more than half the fronds.

Example 19

Fronds of *Lemna gibba* G3 were subjected to microprojectile bombardment to test the effect of microcarrier size on the frequency of foreign gene expression.

For frond proliferation, 200 ml of high salt medium supplemented with 3% sucrose and 0.8% agar was prepared, the pH adjusted to 5.8, autoclaved for 20 minutes at 121° C., cooled, and used to pour 20, 60 mm×15 mm petri dishes. One frond was inoculated to each petri dish. All fronds were grown for two weeks at 23° C. under a 16 hr light/8 hr dark photoperiod with light intensity of approximately 40 μmol/m²·sec. Two microcarrier size 1.0 and 1.6 μm were tested at 3 helium pressure levels: 400, 800, and 1200 psi, using a PDS-1000/He gene gun manufactured by DuPont. Gold microcarriers were prepared and pRT99 DNA was precipitated onto the microcarriers following methods supplied by the manufacturer (Bio-Rad).

Bombarded duckweed fronds were assayed for GUS expression 24 hours after bombardment using histochemical staining methods of Stomp (*Histochemical localization of beta-glucoronidase,* in GUS PROTOCOLS 103–114 (S. R. Gallagher ed. 1991)). The greatest frequency of GUS expression was found in fronds bombarded with 1.6 μm microcarriers and a helium pressure of 800 psi. The number of GUS positive events ranged from 1–21 per frond.

Example 20

Transgenic duckweed plants are regenerated from duckweed callus transformed by ballistic bombardment. Type I callus cultures are grown as described in Example 42 below. Typically, 20–30 duckweed callus pieces, approximately 2–4 mm in diameter, are spread evenly across the bombardment area on MS medium (MS medium described in Example 42). Gold particles (1.6 μM in diameter) and bombardment (helium pressure of 800 psi) as described in Example 18 and Example 19 are used. The DNA for bombardment consists of an expression plasmid containing the gene of interest (e.g., GUS, another marker gene, a gene encoding a mammalian protein, or a gene encoding a bacterial, fungal, plant or mammalian enzyme) and a gene encoding a selectable marker gene, e.g., nptII (kanamycin resistance), hptII (hygromycin resistance), sh ble (zoecin resistance), and bar (phosphinotricin resistance), as well as other sequences necessary for gene expression (e.g., promoter sequences, termination sequences). After bombardment at 800 lbs/sq. inch, the callus is incubated in the dark for two days (or longer if necessary), followed by incubation under a light intensity of 3–5 $\mu$mol/m$^2$·sec for 4–6 weeks. Callus is transferred to fresh medium every two weeks, with the selectable agent added to the medium 2–4 weeks post-bombardment. Selection of resistant callus is continued for 8–16 weeks, until fully resistant callus is produced. Regeneration of transgenic fronds and plants is carried out as described in Example 42.

Transformation with Agrobacterium using Duckweed Fronds

Example 21

Duckweed fronds of *Lemna gibba* G3 were used to test the susceptibility of duckweed to *Agrobacterium tumefaciens* using two different media for co-cultivation, Schenk and Hildebrandt and Murashige and Skoog.

*Agrobacterium tumefaciens* strain AT656 and non-virulent *A. tumefaciens* strain A136 were used to inoculate the duckweed fronds. Strain AT656 is constructed from strain EHA105 (Hood et al., *Transgenic Res.* 2, 208 (1993)) which contains the pTiBo542 vir region on a disarmed pTiBo542 plasmid. The T-DNA is carried on a binary plasmid, pCNL56 (Li et al., *Pl. Mol. Biol.* 20, 1037 (1992)). This binary plasmid is derived from pBIN19, and as modified carries a neomycin phosphotransferase gene under the control of the nopaline synthetase promoter and a nopaline synthetase terminator, and a $\beta$-glucuronidase (GUS) gene (Janssen and Gardner, *Plant Mol. Biol.* 14, 61 (1989)) under the control of the mas2'-CaMV35S promoter and an octopine synthetase terminator. The GUS coding region contains an intron within the coding sequence of the gene to prevent bacterial expression of GUS (Vancanneyt et al., *Mol. Gen. Genet.* 220, 245 (1990)). Strain A136 is derived from the broad host range strain, C58. When C58 is grown at temperatures above 30° C. it loses its Ti-plasmid becoming avirulent A136. These two strains, AT656 and A136, were grown overnight on AB minimal medium (Chilton et al., *Proc. Nat. Acad. Sci.* USA 71, 3672 (1974)) solidified with 1.6% agar and supplemented with 100 $\mu$M acetosyringone at 28° C.

Duckweed fronds were grown in liquid Hoagland's medium containing 3% sucrose for two weeks at 23° C. under a 16 hr light/8 hr dark photoperiod with light intensity of approximately 40 $\mu$mol/m$^2$·sec prior to experimentation. For co-cultivation, 500 ml of Schenk and Hildebrandt medium containing 1% sucrose and 0.6% agar was prepared, the pH adjusted to 5.6, autoclaved at 121° C. for 30 minutes, and cooled. Five-hundred ml of Murashige and Skoog medium containing 3% sucrose and 0.6% agar were also prepared, the pH adjusted to 5.8, autoclaved at 121° C. for 30 minutes, and cooled. To both media, a filter-sterilized solution of acetosyringone was added to a final, medium concentration of 20 mg/L. Twenty, 100 mm×15 mm petri dishes were poured from each cooled medium. For each bacterial strain, the bacteria from one, 100 mm×15 mm petri dish were resuspended for at least one hour prior to use in 100 ml of the following solution (Hiei et al., *The Plant J.* 6, 271 (1994)): Gamborg's B5 salts, Murashige and Skoog vitamins, glycine (8 mg/L), aspartic acid (266 mg/L), arginine (174 mg/L), glutamine (876 mg/L), casamino acids (500 mg/L), sucrose (6.85%), glucose (3.6%), and acetosyringone (20 mg/L). The solution was prepared, the pH adjusted to 5.8, and filter sterilized before the addition of the bacteria.

A 2 bacterial strains×2 co-cultivation media, full-factorial experimental design (4 treatments in total) with 5 replications, with 2 petri dish per replication and 20 fronds per petri dish was used. For inoculation, duckweed fronds were floated in the bacterial solution for several minutes. For co-cultivation, the fronds were transferred to either Schenk and Hildebrandt or Murashige and Skoog medium as described above. The fronds were incubated at 23° C. under a 16 hr light/8 hr dark photoperiod with light intensity of approximately 40 $\mu$mol/m$^2$·sec for four days. The fronds were then transferred to fresh medium of the same composition except that acetosyringone was absent and 500 mg/L of timentin and 50 mg/L kanamycin sulfate were added to the medium.

Histochemical staining for GUS activity following the method of Stomp et al. (*Histochemical localization of beta-glucoronidase*, in GUS PROTOCOLS 103–114 (S. R. Gallagher ed. 1991)) was used to confirm gene transfer in fronds. Staining of fronds inoculated with A136 was done as a control to test bacterially inoculated fronds for endogenous GUS activity. Staining done 10 days after inoculation showed no GUS staining in A136 inoculated controls and high frequencies of staining in fronds inoculated with AT656, regardless of what basal medium, MS or SH, was used for co-cultivation. Transformation frequencies of greater than 70% of the original inoculated fronds were observed, showing GUS positive cells somewhere within the fronds.

Example 22

Fronds of *Lemna gibba* G3 were used to determine the effect of wounding on the frequency of GUS expression after co-cultivation.

Duckweed fronds were grown in liquid Schenk and Hildebrandt medium containing 1% sucrose for two weeks at 23° C. under a 16 hr light/8 hr dark photoperiod with light intensity of approximately 40 $\mu$mol/m$^2$·sec prior to experimentation. For co-cultivation, one liter of Murashige and Skoog medium containing 3% sucrose, 0.6% agar, 20 $\mu$M 2,4-D, 2 $\mu$M BA, and 20 mg/L acetosyringone was prepared, the pH adjusted to 5.8, autoclaved at 121° C. for 30 minutes, and cooled. A filter-sterilized solution of acetosyringone was added to a final, medium concentration of 20 mg/L. Forty, 100 mm×15 mm petri dishes were poured from the cooled medium.

For inoculation, *Agrobacterium tumefaciens* strain AT656 was used and was grown overnight at 28° C. on AB minimal medium (Chilton et al., *Proc. Nat. Acad. Sci* USA 71, 3672 (1974)) containing 50 mg/L kanamycin sulfate and 20 mg/L acetosyringone. For inoculation, the bacteria from one 100 mm×15 mm petri dish were resuspended as described in Example 21.

A 2 wounding treatments×2 bacterial inoculations, full-factorial experimental design (four treatments in total) with 5 replications, with 2 petri dish per replication and 20 fronds per petri dish was used. For wounding treatments, clumps of duckweed fronds were removed from SH medium onto moist, sterile filter paper. The clumps were separated into individual fronds, the fronds were turned abaxial side up, and fronds were wounded one of two ways: 1) cut transversely across the frond centrum, thus cutting through the adjacent meristematic regions from left to right, or 2) cut on each side of the centrum, thus cutting longitudinally through each meristematic region. For bacterial treatments, both classes of wounded fronds were floated on: 1) resuspended AT656 or 2) in the resuspension fluid without the bacteria. For inoculation, fronds were left floating for 10–30 minutes.

For co-cultivation, fronds were transferred to Murashige and Skoog medium as described above with 3% sucrose, 20 μM 2,4-D, 2 μM BA, 100 μM acetosyringone, and 0.6% agar. The fronds were incubated at 23° C. under a 16 hr light/8 hr dark photoperiod with light intensity of approximately 40 μmol/m²·sec for four days. A frond subsample was stained for GUS following the procedure of Stomp (*Histochemical localization of beta-glucoronidase*, in GUS PROTOCOLS 103–114 (S. R. Gallagher ed. 1991). Staining of co-cultivated fronds four days after inoculation showed that the direction of wounding did not affect the frequency of fronds with GUS staining, which averaged approximately 70%. Control, wounded fronds inoculated with bacterial resuspension solution without bacteria showed no GUS staining. The number of fronds with staining within the meristematic regions averaged approximately 40%.

Example 23

Fronds of *Lemna gibba* G3 were used to determine the effect of inoculation time for wounded fronds in bacterial resuspension medium on the frequency of GUS expression after co-cultivation.

Duckweed fronds were grown in liquid Hoagland's medium containing 1% sucrose to a density of approximately 120 fronds per 25 ml of medium in a 125 ml flask at 23° C. under a 16 hr light/8 hr dark photoperiod with light intensity of approximately 40 μmol/m²·sec prior to experimentation. For co-cultivation, 1500 ml of Schenk and Hildebrandt medium with 1% sucrose and 0.6% agar was prepared, the pH adjusted to 5.6, autoclaved at 121° C. for 30 minutes, and cooled. A filter-sterilized solution of acetosyringone was added to a final, medium concentration of 20 mg/L. Sixty, 100 mm×15 mm petri dishes were poured from the cooled medium.

A randomized block experimental design with 4 inoculation time treatments, with 3 replications, with 5 petri dish per replication, and 25 fronds per petri dish was used. For inoculation, *Agrobacterium tumefaciens* strain AT656 was used and was grown overnight at 28° C. on AB minimal medium containing 50 mg/L kanamycin sulfate and 20 mg/L acetosyringone. For inoculation, the bacteria from one 100 mm×15 mm petri dish were resuspended as described in Example 21.

For inoculation, individual fronds were separated from clumps, each turned abaxial side up and wounded with a sterile scalpel in the meristematic regions, then transferred to bacterial suspensions and incubated for 15, 30, 45, or 60 minutes. For co-cultivation, fronds were transferred to Schenk and Hildebrandt co-cultivation medium as described above. All 60 petri dishes were incubated at 23° C. under a 16 hr light/8 hr dark photoperiod with light intensity of approximately 40 μmol/m²·sec for six days. The three replicates were done over a four-day period. Subsamples of co-cultivated fronds from each incubation time 15, 30, 45, or 60 minutes) were taken after 2, 3 and 6 days of co-cultivation. Subsampled fronds were stained for GUS expression following the procedure of Stomp (*Histochemical localization of beta-glucoronidase*, in GUS PROTOCOLS 103–114 (S. R. Gallagher ed. 1991)) The results are presented in Table II.

TABLE II

| Co-cultivation time | Incubation time | Replicate | Total # fronds | # staining |
|---|---|---|---|---|
| 2 days | 15 | 1 | 27 | 27 |
|  | 30 | 1 | 27 | 27 |
|  | 45 | 1 | 28 | 26 |
|  | 60 | 1 | 28 | 26 |
| 3 days | 15 | 2 | 30 | 29 |
|  | 30 | 2 | 28 | 28 |
|  | 45 | 2 | 25 | 24 |
|  | 60 | 2 | 27 | 26 |
| 6 days | 15 | 3 | 27 | 24 |
|  | 30 | 3 | 26 | 22 |
|  | 45 | 3 | 23 | 21 |
|  | 60 | 3 | 30 | 28 |

Although GUS staining on wounded stem ends was evident at 2 days, GUS staining within the meristematic regions was not evident at 2 days of co-cultivation. Meristematic staining was greatest at 3 days co-cultivation and decreased by 6 days of co-cultivation. The time of incubation of duckweed fronds in the bacterial suspension solution did not have a significant effect on the frequency of overall GUS expression after co-cultivation.

Example 24

Fronds of *Lemna gibba* G3 were used to determine the effect of Agrobacterium strain and foreign gene construct on the frequency of GUS expression after co-cultivation.

Two *Agrobacterium tumefaciens* strains were used: AT656 and C58sZ707pBI121. C58sZ707pBI121 is a disarmed, broad host range C58 strain (Hepburn et al., *J. Gen. Microbiol.* 131, 2961 (1985)) into which pBI121 has been transferred. The binary plasmid, pBI121 is derived from pBIN19 and its T-DNA encodes a neomycin phosphotransferase gene under the control of the nopaline synthetase promoter and a nopaline synthetase terminator, and a β-glucuronidase (GUS) gene under the control of a CaMV35S promoter and an octopine synthetase terminator. AT656 was streaked on AB minimal medium containing kanamycin sulfate at 50 mg/L and C58sZ707pBI121 was streaked on AB minimal medium containing streptomycin at 500 mg/L, spectinomycin at 50 mg/L and kanamycin sulfate at 50 mg/L. Both bacterial strains were grown overnight at 28° C.

Duckweed fronds were grown in liquid Hoagland's medium containing 1% sucrose for four weeks at 23° C. under a 16 hr light/8 hr dark photoperiod with light intensity of approximately 40 μmol/m²·sec prior to experimentation. For co-cultivation, 500 ml of Schenk and Hildebrandt medium with 1% sucrose and 0.6% agar was prepared, the pH adjusted to 5.6, autoclaved at 121° C. for 30 minutes, and cooled. A filter-sterilized solution of acetosyringone was added to a final, medium concentration of 20 mg/L. Twenty, 100 mm×15 mm petri dishes were poured from the cooled medium.

A randomized block, experimental design with 2 bacterial strain treatments, with 2 replications, with 5 petri dish per replication, and 25 fronds per petri dish was used. For inoculation, bacteria from one AB plate of each strain were resuspended as described in Example 21.

For inoculation, individual fronds were separated from clumps, each turned abaxial side up and wounded with a sterile scalpel in the meristematic regions, then transferred to bacterial suspensions and incubated for 15–30 minutes. For co-cultivation, fronds were transferred to Schenk and Hildebrandt co-cultivation medium as described above. All 20 petri dishes were incubated at 23° C. under a 16 hr light/8 hr dark photoperiod with light intensity of approximately 40 $\mu$mol/m$^2$·sec for six days. A subsample of fronds was taken at 6 days of co-cultivation and stained for GUS expression. With AT656, 12 of the 13 duckweed frond clumps sampled showed GUS staining, however none was seen in the meristematic region. With C58sZ707pBI121, all the duckweed frond clumps showed extensive staining.

Incubation was continued for all remaining fronds for one week after transfer to fresh medium containing kanamycin sulfate. For transfer after co-cultivation, 1500 ml of Schenk and Hildebrandt medium containing 1% sucrose and 0.6% agar was prepared, the pH adjusted to 5.6, autoclaved at 121° C. for 30 minutes, and cooled. Two antibiotics, timentin and kanamycin sulfate were added as filter-sterilized solutions to the cooled medium to a final medium concentration of 500 mg/L and 2 mg/L, respectively. The cooled medium was used to pour 60, 100 mm×15 mm petri dishes.

After one week the fronds were scored for growth on kanamycin and GUS expression. The proliferating fronds showed 3 categories of response to kanamycin: (1) approximately 20% of the fronds arising from those originally co-cultivated with bacterial strain AT656 showed vigorous growth in the presence of kanamycin and approximately 30% of fronds arising from those originally co-cultivated with bacterial strain C58sZ707pBI121 showed vigorous growth in the presence of kanamycin, (2) another group of fronds clearly had not proliferated and were bleached of chlorophyll and were dying, (3) an intermediate group of fronds showed some proliferation in the presence of kanamycin but the fronds were half bleached, indicating sensitivity to kanamycin. Results of GUS staining indicated that active enzyme was still present at high frequency in the originally co-cultivated fronds.

Example 25

Fronds of Lemna gibba G3 were used to determine the effect of Agrobacterium strain, foreign gene construct, and frond pre-treatment on the frequency of GUS expression after co-cultivation.

Two Agrobacterium tumefaciens strains were used: AT656 and EHA101pJR1. EHA101pJR1 is a binary Agrobacterium tumefaciens strain containing a disarmed pTiBo542 plasmid harboring the hypervirulence region of wild-type strain, Bo542, and a small binary plasmid harboring a hygromycin phosphotransferase gene under the control of an alcohol dehydrogenase 1 enhanced, CaMV35S promoter and a β-glucuronidase gene constructed as in AT656. These two strains were streaked on potato dextrose agar with 50 mg/L kanamycin and grown overnight at 28° C.

Duckweed fronds were grown on liquid Schenk and Hildebrandt medium containing 1% sucrose with and without 10 $\mu$M indoleacetic acid (IAA), a concentration sufficient to increase proliferation rate. Fronds were grown in 25 ml aliquots of medium in 125 ml flasks, at 23° C. under a 16 hr light/8 hr dark photoperiod with light intensity of approximately 40 $\mu$mol/m$^2$·sec. For co-cultivation, 500 ml of Schenk and Hildebrandt medium containing 1% sucrose, 0.8% agar, 20 mg/L acetosyringone, and with and without 10 $\mu$M indoleacetic acid was prepared, pH adjusted to 5.6, autoclaved at 121° C. for 30 minutes, and cooled. Filter-sterilized solutions of acetosyringone, and acetosyringone and indoleacetic acid were added to the cooled medium, to the final, appropriate concentrations. Twenty, 100 mm×15 mm petri dishes were poured from the cooled medium.

A randomized block, experimental design with 2 bacterial strain treatments×2 frond growth media, with 5 replications, with one petri dish per replication, and 20 fronds per petri dish was used. For inoculation, bacteria of each strain were separately resuspended as described in Example 21. For inoculation, individual fronds were separated from clumps, each turned abaxial side up and wounded with a sterile scalpel in the meristematic regions, then transferred to bacterial suspensions of either AT656 or EHA101pJR1, and incubated for 10–15 minutes. For co-cultivation, fronds were transferred to solid Schenk and Hildebrandt medium with 1% sucrose, 0.8% agar and 100 $\mu$M acetosyringone with and without 10 $\mu$M indoleacetic acid as described above, abaxial side down.

The fronds were co-cultivated for 4 days at 23° C. under a 16 hr light/8 hr dark photoperiod with light intensity of approximately 40 $\mu$mol/m$^2$·sec. The fronds from two plates from each of the four treatments were stained for GUS expression. Table III presents the results of GUS staining.

TABLE III

| Media | Strain | Total # fronds | Total # Stained |
| --- | --- | --- | --- |
| SH | AT656 | 61 | 12 |
| SH | EHA101pJR1 | 62 | 4 |
| SH + IAA | AT656 | 66 | 32 |
| SH + IAA | EHA101pJR1 | 68 | 2 |

Regardless of the presence or absence of IAA, fronds co-cultivated with EHA101pJR1 had much lower frequencies of fronds showing GUS expression. An effect of IAA in the incubation medium was detected with medium containing IAA giving 48% of co-cultivated fronds showing GUS expression compared to 20% of fronds co-cultivated on medium without IAA.

Example 26

Fronds of Lemna gibba G3 were co-cultivated for five different times: 12.5, 18.5, 40.5, 82, and 112 hours, with bacterial strain AT656 to test the effect of co-cultivation time on GUS expression after co-cultivation.

Duckweed fronds were grown for two weeks on liquid Schenk and Hildebrandt medium containing 1% sucrose and 10 $\mu$M indoleacetic acid at 23° C. under a 16 hr light/8 hr dark photoperiod with light intensity of approximately 40 $\mu$mol/m$^2$·sec prior to experimentation. For co-cultivation, 750 ml of Schenk and Hildebrandt medium with 1% sucrose, 0.8% agar, 10 $\mu$M indoleacetic acid, and 20 mg/L acetosyringone was prepared, the pH was adjusted to 5.6, the medium autoclaved at 121° C. for 30 minutes, and cooled. A filter-sterilized solution of acetosyringone and indoleacetic acid was added to the final medium concentration. Thirty, 100 mm×15 mm petri dishes were poured from the cooled medium. Bacterial Thirty, 100 mm×15 mm petri dishes were poured from the cooled medium. Bacterial strain AT656 was streaked on potato dextrose agar with 50 mg/L kanamycin sulfate and grown overnight at 28° C.

A randomized block, experimental design with 5 incubation time treatments, with 6 replications, with one petri dish per replication, and 60 fronds per petri dish was used. For inoculation, bacteria were resuspended as described in Example 21. For inoculation, individual fronds were separated from clumps and each turned abaxial side up and wounded with a sterile scalpel in the meristematic regions. Fronds were then transferred to the bacterial resuspension solution and incubated for approximately 10–15 minutes.

For co-cultivation, fronds were transferred to solid Schenk and Hildebrandt medium as described above, abaxial side down. The fronds were co-cultivated under a 16 hr light/8 hr dark photoperiod with light intensity of approximately 40 $\mu mol/m^2 \cdot sec$.

At the appropriate times, 10 fronds were removed from each petri dish (6 samples) and histochemically stained for GUS expression. Table IV gives the results of GUS staining:

TABLE IV

| Time (hr) | Total # Fronds | Total # Staining |
|---|---|---|
| 12.5 | 61 | 0 |
| 18.5 | 61 | 0 |
| 40 | 61 | 0 |
| 82 | 75 | 24 |
| 112 | 67 | 25 |

Co-cultivation time had a significant effect on the frequency of fronds with GUS expression. Before 40 hours, no GUS expression was detectable. By 3.5 days (82 hours) GUS expression was readily detectable. Longer co-cultivation did not significantly increase the frequency, intensity, or tissue association pattern of GUS expression in duckweed fronds. It was concluded that 3.5–4 days is the shortest co-cultivation time that will give the maximum frequency of gene transfer in duckweed fronds.

Example 27

Bacteria of strain AT656, grown on three different bacterial media: AB minimal, potato dextrose, and mannitol glutamine Luria broth, were used to co-cultivate *Lemna gibba* G3 fronds, that had been grown with and without indoleacetic acid prior to co-cultivation, in light and in the dark to test the effects of these treatments on GUS expression following co-cultivation.

*Lemna gibba* G3 fronds were grown for two weeks on liquid Schenk and Hildebrandt medium containing 1% sucrose and with or without 10 $\mu$M indoleacetic acid in 25 ml aliquots in 125 ml flasks, at 23° C. under a 16 hr light/8 hr dark photoperiod with light intensity of approximately 40 $\mu mol/m^2 \cdot sec$ prior to experimentation. For co-cultivation, 900 ml of Schenk and Hildebrandt medium containing 1% sucrose, 0.8% agar, with and without 10 $\mu$M indoleacetic acid, and 20 mg/L acetosyringone was prepared, the pH was adjusted to 5.6, the medium autoclaved at 121° C. for 30 minutes, and cooled. Filter-sterilized solutions of acetosyringone and indoleacetic acid were added to the appropriate, final medium concentrations. Thirty-six, 100 mm×15 mm petri dishes were poured from the cooled medium. Three bacterial media: 1) AB minimal containing 1.6% agar (AB), Difco potato dextrose medium with 1.6% agar (PDA), and mannitol glutamine (Roberts and Kerr, *Physiol. Plant Path.* 4, 81 (1974) Luria broth medium with 1.6% agar (MGL; Miller, EXPERIMENTS IN MOLECULAR GENETICS 433 (1972)) were prepared, autoclaved at 121° C. for 20 minutes, and cooled. A filter-sterilized solution of kanamycin sulfate and acetosyringone was added to the cooled media to final medium concentrations of 50 mg/L and 20 mg/L, respectively. AT656 was streaked on these three media and incubated overnight at 28° C.

A full-factorial experimental design with 3 bacterial media×2 plant media×2 light condition treatments (12 treatments in total), with 3 replications, with one petri dish per replication, and 20–25 fronds per petri dish was used. For inoculation, bacteria from each medium were separately resuspended as described in Example 21.

For inoculation, individual fronds were separated from clumps, each turned abaxial side up and wounded with a sterile scalpel in the meristematic regions. Fronds were then transferred to the bacterial resuspension solution and incubated for approximately 10–15 minutes. After inoculation, fronds were transferred to solid Schenk and Hildebrandt co-cultivation medium as described above. The fronds were co-cultivated for 4 days under a 16 hr light/8 hr dark photoperiod with light intensity of approximately 40 $\mu mol/m^2 \cdot sec$ for the light treatment or placed in total darkness for the dark treatment. After co-cultivation, all fronds were stained for GUS expression following the procedure of Stomp et al. (*Histochemical localization of beta-glucoronidase,* in GUS PROTOCOLS 103–114 (S. R. Gallagher ed. 1991)). Table V gives the results of GUS staining:

TABLE V

| Bacterial Medium | Plant Medium | Light or Dark | Total # Fronds | Total # Stained | # Stained Meristem |
|---|---|---|---|---|---|
| PDA | SH | D | 63 | 60 | 5 |
| PDA | SH | L | 67 | 66 | 8 |
| MGL | SH | D | 66 | 65 | 7 |
| MGL | SH | L | 70 | 65 | 9 |
| AB | SH | D | 58 | 58 | 7 |
| AB | SH | L | 62 | 60 | 6 |
| PDA | SH + IAA | D | 61 | 61 | 14 |
| PDA | SH + IAA | L | 68 | 63 | 14 |
| MGL | SH + IAA | D | 62 | 61 | 11 |
| MGL | SH + IAA | L | 46 | 39 | 2 |
| AB | SH + IAA | D | 62 | 61 | 6 |
| AB | SH + IAA | L | 58 | 53 | 3 |

Bacterial medium has a significant effect on the frequency of GUS expression after 4 days of co-cultivation. AB medium gave the lowest frequency of GUS expression and PDA the highest. Growing fronds on indoleacetic acid prior to inoculation increased the frequency of GUS expression after co-cultivation. The presence of light during co-cultivation did not significantly affect the frequency of GUS expression after co-cultivation in treatments using fronds grown without indoleacetic acid, however, co-cultivation in the dark did increase the frequency of GUS expression in treatments that used fronds grown in the presence of indoleacetic acid. Averaging frequencies from PDA and MGL across the duckweed fronds grown on Schenk and Hildebrandt medium with indoleacetic acid gives a frequency of GUS expression in meristematic tissue of approximately 17%.

Example 28

Six co-cultivation times and the presence or absence of light during co-cultivation were examined for their effect on GUS expression following co-cultivation.

*Lemna gibba* G3 fronds were grown for 17 days on Schenk and Hildebrandt medium containing 1% sucrose and 10 $\mu$M indoleacetic acid at 23° C. under a 16 hr light/8 hr dark photoperiod with light intensity of approximately 40 $\mu mol/m^2 \cdot sec$. For co-cultivation, 150 ml of Schenk and Hildebrandt medium containing 1% sucrose, 1% agar, 10 $\mu$M indoleacetic acid, and 20 mg/L acetosyringone was prepared, the pH adjusted to 5.6, autoclaved for 30 minutes, and cooled. Filter-sterilized solutions of acetosyringone and indoleacetic acid were added to the final medium concentrations to the cooled medium. The medium was used to pour 6, 100 mm×15 mm petri dishes. *Agrobacterium tumefaciens* strain AT656 was streaked on AB minimal medium containing kanamycin sulfate at 50 mg/L and 20 mg/L acetosyringone and grown overnight at 23° C.

A randomized block, experimental design with 6 co-cultivation time treatments, with 6 replications, with one petri dish per replication, and 30 fronds per petri dish was used. For inoculation, the bacteria from one petri dish were resuspended as described in Example 21.

For inoculation, individual fronds were separated from clumps, each turned abaxial side up and wounded with a sterile scalpel in the meristematic regions. Fronds were transferred to bacterial suspensions and incubated for 10 minutes. For co-cultivation, fronds were transferred to Schenk and Hildebrandt co-cultivation medium as described above. Three plates were wrapped in aluminum foil to effect complete darkness and all plates were incubated at 23° C. under a 16 hr light/8 hr dark photoperiod with light intensity of approximately 40 $\mu$mol/m$^2$·sec for six time points: 13, 23, 36, 49, 73.5, and 93 hours. After co-cultivation for the appropriate time, 5 fronds were removed from each of 6 plates (3 samples dark and 3 samples light) and stained for GUS expression following the procedure of Stomp et al. (*Histochemical localization of beta-glucoronidase,* in GUS PROTOCOLS 103–114 (S. R. Gallagher ed. 1991)).

The results showed that GUS expression became evident by 23 hours after co-cultivation, with expression detected only at the broken end of stems. By 36 hours, staining was detected in cells surrounding wounds and at the broken ends of stems. Staining was more intense overall, however the level of staining intensity was greater in the fronds incubated in the dark. By 49 hours, the difference in staining intensity and staining pattern were evident in the dark versus light treatments. Staining was more extensive in fronds incubated in the dark, however the frequency of fronds showing GUS expression and the frequency of GUS expressing meristematic regions was not significantly different between light and dark treatments. By 73.5 hours the staining pattern and the frequency of staining did not differ significantly between dark and light treatment except that wounded tissue staining was more prevalent in the dark treatment. By 93 hours (approximately 4 days) the greatest number of GUS expressing, meristematic regions was detected, with the dark treatment definitely superior to the light treatment. Intense staining was still present in wounded cells.

Example 29

Fronds of *Lemna gibba* G3 were used to determine the effect of bacterial resuspension solutions, the osmotic potential of these solutions, and frond wounding on the frequency of GUS expression following co-cultivation.

Fronds were grown on liquid Schenk and Hildebrandt medium containing 1% sucrose at 23° C. under a 16 hr light/8 hr dark photoperiod with light intensity of approximately 40 $\mu$mol/m$^2$·sec. For co-cultivation, 1800 ml of Schenk and Hilderbrandt (SH) medium with 1% sucrose, 0.8% of unwashed agar, and 20 mg/L acetosyringone was prepared, the pH adjusted to 5.6, autoclaved for 30 minutes at 121° C. for 30 minutes, and cooled. Heat labile acetosyringone was added to autoclaved, cooled medium as a filter-sterilized solution. The cooled medium was used to pour 72, 100 mm×15 mm petri dishes. Agrobacterium strain AT656 was streaked onto AB minimal medium containing 20 mg/L acetosyringone and 50 mg/L kanamycin sulfate and grown overnight at 28° C.

A full-factorial experimental design with 12 bacterial resuspension solution×2 wounding treatments (24 treatments in total), with 3 replications, with one petri dish per replication, and 20 fronds per petri dish was used. Ten combinations of two different bacterial resuspension solutions: 1) Gamborg's B5 salts, Murashige and Skoog vitamins, glycine (8 mg/L), aspartic acid (266 mg/L), arginine (174 mg/L), glutamine (876 mg/L), casamino acids (500 mg/L), sucrose (6.85%), glucose (3.6%), and acetosyringone (20 mg/L), and 2) Schenk and Hildebrandt medium with 1% sucrose, each at 5 different mannitol concentrations: 0, 0.2, 0.4, 0.6 and 0.8 M, were tested for their efficacy in gene transfer. In addition, two other solutions were tested: 3) Gamborg's B5 salts, Murashige and Skoog vitamins, glycine (8 mg/L), aspartic acid (266 mg/L), arginine (174 mg/L), glutamine (876 mg/L), casamino acids (500 mg/L), and acetosyringone (20 mg/L), and 4) Schenk and Hildebrandt medium with sucrose (6.85%), glucose (3.6%), and acetosyringone (20 mg/L). All bacterial resuspension solutions were filter-sterilized prior to use. For inoculation, bacteria from one AD plate were resuspended in 100 ml of each of the 12 resuspension solutions at least one hour prior to use.

The importance of wounding fronds prior to inoculation was also tested. For either wounded or unwounded fronds, individual fronds were first separated from clumps. For wounding, fronds were turned abaxial side up and stabbed with a sterile scalpel in the meristematic regions. Unwounded fronds received no further treatment after separation into individual fronds.

For inoculation, 120 fronds, 60 wounded and 60 unwounded, were floated on each of the 12 bacterial resuspension media for 10 minutes, with wounded fronds inoculated separately from unwounded fronds. For co-cultivation, the fronds were transferred to solid Schenk and Hildebrandt medium as described above. All treatments were co-cultivated for 4 days in the dark. After four days of co-cultivation, two plates from each treatment were randomly picked and stained for GUS expression.

The results indicated that regardless of media, 0.6 M of mannitol gave the highest frequencies of GUS expression after co-cultivation. The simpler, Schenk and Hildebrandt medium formulation worked as well as the more complex medium formulation using Gamborg's B5 salts. Wounding gave a measurable, but not statistically significant, increase in the frequency of fronds showing GUS expression and did not increase the frequency of staining in the meristematic region.

Example 30

Fronds of *Lemna gibba* G3 were used to test the effect of bacterial concentrations during inoculation on the frequency of GUS expression following co-cultivation.

Duckweed fronds grown on liquid Schenk and Hildebrandt medium containing 1% sucrose and 10 $\mu$M indoleacetic acid in 25 ml aliquots in 125 ml flasks at 23° C. under a 16 hr light/8 hr dark photoperiod with light intensity of approximately 40 $\mu$mol/m$^2$·sec for two weeks prior to use. For co-cultivation, 750 ml of Schenk and Hildebrandt medium with 1% sucrose, 1% agar, 20 mg/L acetosyringone, and 10 $\mu$M indoleacetic acid was prepared, the pH adjusted to 5.6 autoclaved at 121° C. for 30 minutes, and cooled. Filter-sterilized solutions of acetosyringone and indoleacetic acid were added to the cooled medium to obtain the final medium concentrations. The cooled medium was used to pour 30, 100 mm×15 mm petri dishes. Agrobacterium strain AT656 was streaked on half-strength potato dextrose agar-mannitol glutamine Luria broth medium with 1.6% Difco Bacto-agar, 20 mg/L acetosyringone, and 50 mg/L kanamycin sulfate and grown overnight at 28° C.

A randomized block experimental design with 10 bacterial concentration treatments, with 3 replications, with one petri dish per replication and 20 individual fronds or frond clumps per petri dish was used. For inoculation, bacteria from one petri dish were resuspended as described in Example 21. This bacterial solution constituted the "undiluted" sample and was the beginning of a serial dilution series for the following dilutions: 1/3, $10^{-1}$, 1/33, $10^{-2}$, 1/333, $10^{-3}$, 1/3333, $10^{-4}$, $10^{-5}$. The 1/3 dilution had an OD540 nm of 1.006, which corresponded to approximately $1.6 \times 10^9$ bacteria/ml.

For inoculation, individual fronds were separated from clumps, each turned abaxial side up and wounded with a sterile scalpel in the meristematic regions. Fronds were then transferred to each of the ten different bacterial resuspension solution concentrations and incubated for approximately 10–15 minutes. For co-cultivation, fronds were transferred to solid Schenk and Hildebrandt co-cultivation medium described above, abaxial side down. The fronds were co-cultivated for 4 days at 23° C. in the dark. After co-cultivation, all fronds were stained for GUS expression following the procedure of Stomp et al. (*Histochemical localization of beta-glucoronidase*, in GUS PROTOCOLS 103–114 (S. R. Gallagher ed. 1991)).

The results showed that the frequencies of GUS expression varied ten-fold across bacterial concentration. The greatest frequency of GUS expression was observed at the highest bacterial concentration tested. At dilutions greater than $10^{-3}$, no GUS expression was detected.

Example 31

Fronds of *Lemna gibba* G3 were used to test the effect of four co-cultivation media on GUS expression using an optimized transformation protocol.

Fronds were grown on liquid Schenk and Hildebrandt medium containing 1% sucrose and 10 $\mu$M indoleacetic acid at 23° C. under a 16 hr light/8 hr dark photoperiod with light intensity of approximately 40 $\mu$mol/m$^2$·sec. For co-cultivation, four media were used: 1) Murashige and Skoog medium (MS) with 20 $\mu$M 2,4-D and 0.1 $\mu$M BA (MS1), 2) MS medium with 20 $\mu$M 2,4-D and 1 $\mu$M BA (MS2), 3) MS medium with 1 $\mu$M 2,4-D and 2 $\mu$M BA (MS3), and 4) Schenk and Hilderbrandt medium (SH). For each medium, 100 ml containing the appropriate plant growth regulators containing 3% sucrose, 0.15% Gelrite and 0.4% Difco Bacto-agar was prepared, the pH adjusted to 5.6, autoclaved at 121° C. for 20 minutes, and cooled. A filter-sterilized acetosyringone solution was added to each cooled medium to a final concentration of 20 mg/L. Each medium was used to pour 4, 100 mm×15 mm petri dishes. Bacterial strain AT656 was streaked on potato dextrose agar with 20 mg/L acetosyringone and 50 mg/L kanamycin sulfate and grown overnight at 28° C.

A randomized block experimental design with 4 media treatments with four replications, with one petri dish per replication and 20 fronds per petri dish was used. For inoculation, the bacteria from one petri dish were resuspended for one hour prior to use in 100 ml of filter-sterilized SH medium with 0.6 M mannitol and 20 mg/L acetosyringone at pH 5.6. For inoculation, individual fronds were separated from clumps and floated in the resuspended bacteria for 8–10 minutes. For co-cultivation, the fronds were transferred to co-cultivation medium described above (MS1, MS2, MS3, SH). Fronds were co-cultivated at 23° C. in the dark for four days. After four days of co-cultivation, all fronds were stained for GUS expression.

The frequency of fronds showing GUS expression ranged from 80–90% across all treatments. Co-cultivation medium did not have a significant effect on this frequency. The intensity of GUS staining ranged from light to intense. Staining was associated with root tips, stems, broken ends of stems and wounds, meristematic regions, and the frond margins.

Example 32

Frond transformation using Agrobacterium is accomplished through manipulation of the cell division rate of the fronds prior to inoculation, the medium on which the Agrobacteria are grown, optimization of co-cultivation parameters including secondary metabolites such as acetosyringone, the concentration of the Agrobacteria, the osmolarity of the inoculation fluid, the duration of the co-cultivation period, and the light intensity of the co-cultivation period.

Based on the studies described in the previous Examples, a preferred method of frond transformation and selection is as follows. Typically, fronds are grown on medium containing an auxin that increases the proliferation rate of the fronds, with NAA, IBA and IAA being the preferred auxins and the preferred concentrations ranging from 0.2–1 $\mu$M. Agrobacteria are grown on a medium without rich nutrient supplements and including such secondary metabolites as acetosyringone, with potato dextrose agar and mannitol glutamine Luria broth as preferred media. The frequency of transformation is determined by the composition of the inoculating fluid, with the preferred fluid being MS or SH basal salts supplemented with 0.6 M mannitol and 100 $\mu$M acetosyringone. The concentration of Agrobacteria resuspended in this inoculating fluid also affects the frequency of transformation, with the preferred concentration on the order of $1 \times 10^9$ bacteria per ml. Inoculation time can vary with the preferred time ranging from 2–20 minutes. Co-cultivation time also affects the frequency of transformation, with a time of 3–4 days being preferred. Co-cultivation can be carried on under light or dark conditions, with darkness (e.g., subdued light) being preferred.

Growth of transformed fronds is also dependent on preferred conditions. MS and SH are the preferred media. Decontamination of the fronds from infecting Agrobacteria is done using the appropriate antibiotics at high concentrations, typically 100–500 mg/L, with frequent transfer of infected tissue, the preferred method being transfer to fresh medium with antibiotic every 2–4 days. Incubation under low light intensity, the preferred range being 1–5 $\mu$mol/m$^2$·sec, for an initial resting/recovery period of 3–6 weeks is preferred.

Selection by growth in the presence of the selection agent can be initiated at variable times, with the preferred time being 1–3 weeks after inoculation. Initial selection under reduced light levels and low selection agent concentration is also preferred, with light levels of 1–5 $\mu$mol/m$^2$·sec and low concentration ranges appropriate for the selection agent as determined from toxicity studies for the specific agent. For kanamycin sulfate, the typical range is 2–10 mg/L.

Example 33

Fronds from strains within 10 species of duckweed: *Lemna trisulca* 7315, *Lemna minor* 7101, *Lemna japonica* 7427, *Lemna turionifera* 6601, *Lemna gibba* G3, *Lemna valdiviana* 7002, *Lemna aequinocitalis* 7001, *Lemna miniscula* 6711, *Lemna obscura* 7325, and *Spirodela punctata* 7273, were tested for their ability to give GUS expression following co-cultivation using the transformation protocol developed with *Lemna gibba* G3.

All duckweed strains except *L. gibba* G3 were grown on liquid Schenk and Hildebrandt medium with 1% sucrose in 25 ml aliquots in 125 ml flasks. *Lemna gibba* G3 was grown on Schenk and Hildebrandt medium with 1% sucrose and 10 $\mu$M indoleacetic acid. All duckweed cultures were incubated at 23° C. under a 16 hr light/8 hr dark photoperiod with light intensity of approximately 40 $\mu$mol/m$^2$·sec. For co-cultivation, 400 ml of Schenk and Hildebrandt medium containing 1% sucrose, 0.9% agar, and 20 mg/L acetosyringone was prepared, the pH adjusted to 5.6, autoclaved at 121° C. for 30 minutes and cooled. A filter-sterilized solution of acetosyringone was added to the cooled medium to obtain the final medium concentration. The cooled medium was used to pour 10, 100 mm×15 mm petri dishes. *Agrobacterium tumefaciens* strain AT656 was streaked on half-strength potato dextrose agar mixed with half-strength mannitol glutamine Luria broth medium containing 20 mg/L acetosyringone and 50 mg/L kanamycin sulfate overnight at 28° C.

A randomized block experimental design with 10 duckweed strain treatments, with one replication, with one petri dish per replication and 20–25 fronds per petri dish was used. For inoculation, bacteria from one petri dish were resuspended as described in Example 21.

For inoculation, individual fronds were separated from clumps, each turned abaxial side up and wounded with a sterile scalpel in the meristematic regions. Fronds were transferred to bacterial suspensions and incubated for approximately 10 minutes. For co-cultivation, fronds were transferred to Schenk and Hildebrandt co-cultivation medium described above and incubated at 23° C. in the dark for four days.

After co-cultivation the fronds were stained for GUS expression. Of the 10 strains tested, 8 showed GUS expression in a pattern identical to *L. gibba* G3 and at frequencies ranging from 14% to 80%.

Example 34

Twenty strains of duckweed from the 4 genera of the Lemnaceae were tested for their ability to give GUS expression following co-cultivation with Agrobacterium strain AT656 using the transformation protocol developed with *L. gibba* G3. The twenty strains were: *Wolffiella lingulata* strains 8742 and 9137, *Wl. neotropica* strains 7279 and 8848, *Wl. oblongata* strains 8031 and 8751, *Wolffia arrhiza* strains 7246 and 9006, *Wa. australiana* 7317, *Wa. brasiliensis* strains 7397, 7581, and 8919, *Wa. columbiana* strains 7121 and 7918, *Spirodela intermedia* 7178, *S. polyrrhiza* strains 7960 and 8652, *S. punctata* strains 7488 and 7776, and *L. gibba* G3.

All strains were grown on liquid Schenk and Hildebrandt medium with 1% sucrose, pH of 5.6 for two weeks prior to experimentation. For co-cultivation, 1500 ml of Schenk and Hildebrandt medium containing 1% sucrose, 0.8% agar, and 20 mg/L acetosyringone was prepared, the pH adjusted to 5.6, autoclaved at 121° C. for 30 minutes, and cooled. A filter-sterilized solution of acetosyringone was added to the cooled medium to obtain the final medium concentration. The cooled medium was used to pour 60, 100 mm×15 mm petri dishes. The bacterial strain, AT656 was streaked on potato dextrose agar with 20 mg/L acetosyringone and 50 mg/L kanamycin sulfate and grown overnight at 28° C. For inoculation, the bacteria from one petri dish were resuspended for at least one hour prior to use in Schenk and Hildebrandt medium with 0.6 M mannitol, 20 mg/L acetosyringone, pH of 5.6 that was filter-sterilized before use.

A randomized block experimental design with 20 duckweed strain treatments, with 3 replications, with one petri dish per replication and 20 individual fronds or frond clumps per petri dish was used. For inoculation, individual fronds of Spirodela and Wolfiella strains and *L. gibba* G3 were separated from clumps. For Wolffia strains, fronds were inoculated as clumps because their small size made individual frond separation difficult. For inoculation, fronds of each duckweed strain were floated in the bacterial suspension solution for 2–5 minutes. For co-cultivation, the fronds were transferred from bacterial solution to solid Schenk and Hildebrandt co-cultivation medium described above. For Spirodela and Wolfiella strains and for *L. gibba* G3, 20 individual fronds were transferred to each of 3 replicate dishes; for Wolffia strains, 20 small frond clumps were transferred to each of 3 replicate plates. All strains were co-cultivated in darkness at 23° C. for four days.

After co-cultivation, 2 plates from each strain were stained for GUS expression. Staining results showed that all but one species tested and the majority of duckweed strains within species gave some GUS expression 4 days after co-cultivation. Of the 4 Wolffia species tested, all showed varying frequencies of GUS expression. The three strains of *Wolffia brasiliensis* showed the highest frequencies of GUS expression, ranging from 50–75%. Across the 6 strains within the genus Wolfiella, the frequency of GUS expression was lower, ranging from 5–12%. Two of the three Spirodela species gave GUS expression of 10 and 35%; the third gave no indication of GUS expression. *Lemna gibba* G3, serving as the positive control had a GUS expression frequency of approximately 50%.

Transformation by Agrobacteria using Callus Cultures

Example 35

Type I callus produced from *Lemna gibba* G3 fronds was used to test its ability to give GUS expression using the optimized transformation protocol developed with *L. gibba* G3 fronds and to test the effect of vacuum infiltration.

Type I callus was produced by growing fronds on solid Murashige and Skoog medium containing 3% sucrose, 0.15% Gelrite, 0.4% Difco Bacto-agar, 5 $\mu$M 2,4-dichlorophenoxyacetic acid (2,4-D), and 2 $\mu$M benzyladenine (BA). Callus induction and all subsequent culture was at 23° C. and under a 16 hr light/8 hr dark photoperiod with light intensity of approximately 40 $\mu$mol/m$^2$·sec. After 4 weeks of callus induction, Type I callus clumps were separately cultured on the same medium with the 2,4-D concentration reduced to 1 $\mu$M. The callus was subcultured to fresh medium every two weeks until sufficient callus was proliferated for experimentation.

For co-cultivation, 400 ml of solid Murashige and Skoog medium (MS) with 3% sucrose, 0.15% Gelrite, 0.4% Difco Bacto-agar, 1 $\mu$M 2,4-D, and 2 $\mu$M BA was prepared, the pH adjusted to 5.6, autoclaved at 121° C. for 20 minutes, and cooled. A filter-sterilized solution of acetosyringone was added to a final, medium concentration of 20 mg/L. The cooled medium was used to pour 16, 100 mm×15 mm petri dishes. Agrobacterium strain AT656 was streaked on potato dextrose agar with 20 mg/L acetosyringone and 50 mg/L kanamycin sulfate and grown overnight at 28° C.

A randomized block experimental design with two vacuum infiltration treatments with four replications with two petri dishes per replication and ten callus pieces per petri dish was used. For inoculation, the bacteria were resuspended in filter-sterilized Schenk and Hildebrandt medium containing 0.6 M mannitol and 20 mg/L of acetosyringone at pH 5.6 for at least one hour before use. Inoculation with bacteria was done with and without vacuum infiltration. Without vacuum infiltration, small pieces of Type I callus were placed in the bacterial solution for 10 minutes, then blotted and transferred to MS co-cultivation medium as described above. With vacuum infiltration, the callus was placed in bacterial solution, a vacuum of 10 inches of mercury applied for 10 minutes, then the callus was blotted and transferred to MS co-cultivation medium. All dishes were co-cultivated in the dark at 23° C.

After four, six and nine days of co-cultivation, approximately 40, 20 and 20 callus pieces, respectively, were stained for GUS expression. Results showed that the frequencies of callus pieces showing GUS expression did not vary with respect to vacuum infiltration treatment nor did the frequencies vary with the time of co-cultivation. Without vacuum infiltration across all time points, GUS staining ranged from 25–78% and with vacuum infiltration the frequencies ranged from 25–74%. The intensity of GUS staining varied from dark to light blue and had no correlation with treatment.

Example 36

Four different co-cultivation media were tested for their effect on the frequency of GUS expression following co-cultivation of Type I callus with Agrobacterium strain AT656.

Type I callus was produced by growing *Lemna gibba* G3 fronds on solid Murashige and Skoog medium containing 3% sucrose, 0.15% Gelrite, 0.4% Difco Bacto-agar, 5 $\mu$M 2,4-D, and 2 $\mu$M BA. Callus induction and all subsequent culture was at 23° C. and under a 16 hr light/8 hr dark photoperiod with light intensity of approximately 40 $\mu$mol/m$^2$·sec. After 4 weeks of callus induction, Type I callus clumps were separately cultured on the same medium with the 2,4-D concentration reduced to 1 $\mu$M. The callus was subcultured to fresh medium every two weeks until sufficient callus was proliferated for experimentation.

For co-cultivation, four media were tested: Murashige and Skoog medium (MS) with 20 $\mu$M 2,4-D and 0.1 $\mu$M BA (MS 1), MS medium with 20 $\mu$M 2,4-D and 1 $\mu$M BA (MS2), MS medium with 1 $\mu$M 2,4-D and 2 $\mu$M BA (MS3), and Schenk and Hilderbrandt medium (SH) without plant growth regulators. Fifty milliliters of each media were prepared containing 3% sucrose, 0.15% Gelrite and 0.4% Difco Bacto-agar, the pH adjusted to 5.6, autoclaved at 121° C. for 20 minutes, cooled and a filter-sterilized solution of acetosyringone added to the cooled medium to a final concentration of 20 mg/L. The media were used to pour 24, 100 mm×15 mm petri dishes. Agrobacterium strain AT656 was streaked on potato dextrose agar containing 20 mg/L acetosyringone and 50 mg/L kanamycin sulfate and grown overnight at 28° C.

A randomized block experimental design with 4 co-cultivation media treatments with two replications with one petri dish per replication and 20 callus pieces per petri dish was used. For inoculation, the bacteria from one petri dish were resuspended in filter sterilized SH medium containing 0.6 M mannitol and 20 mg/L acetosyringone at pH 5.6 for at least one hour prior to use. For inoculation, Type I callus pieces were placed in bacterial solution for 8 minutes, blotted and then transferred to the four different co-cultivation media. All plates were co-cultivated at 23° C. in the dark for four days. After co-cultivation, all callus was stained for GUS expression following the procedure of Stomp et al. (*Histochemical localization of beta-glucoronidase*, in GUS PROTOCOLS 103–114 (S. R. Gallagher ed. 1991)).

The co-cultivation medium did not have a significant effect on the frequency of callus pieces showing GUS expression. Across all treatments, the frequency of GUS expression ranged from 70–85%. The intensity of GUS expression varied, with staining ranging from dark to light blue.

Example 37

Two different co-cultivation times, two and four days, were tested for their effect on the frequency of GUS expression following co-cultivation of Type I callus with Agrobacterium strain AT656.

Type I callus was produced by growing *Lemna gibba* G3 fronds on solid Murashige and Skoog medium containing 3% sucrose, 0.15% Gelrite, 0.4% Difco Bacto-agar, 5 $\mu$M 2,4-D, and 2 $\mu$M BA. Callus induction and all subsequent culture was at 23° C. and under a 16 hr light/8 hr dark photoperiod with light intensity of approximately 40 $\mu$mol/m$^2$·sec. After 4 weeks of callus induction, Type I callus clumps were separately cultured on the same medium with the 2,4-D concentration reduced to 1 $\mu$M. The callus was subcultured to fresh medium every two weeks until sufficient callus was proliferated for experimentation.

For co-cultivation, 400 ml of solid Murashige and Skoog medium (MS) with 3% sucrose, 0.15% Gelrite, 0.4% Difco Bacto-agar, 1 $\mu$M 2,4-D and 2 $\mu$M BA was prepared, the pH adjusted to 5.6, autoclaved at 121° C. for 20 minutes, and cooled. A filter-sterilized solution of acetosyringone was added to the cooled medium to a final concentration of 20 mg/L. The cooled medium was used to pour 16, 100 mm×15 mm petri dishes. Agrobacterium strain AT656 was streaked on potato dextrose agar with 20 mg/L acetosyringone and 50 mg/L kanamycin sulfate and grown overnight at 28° C.

A randomized block experimental design with two co-cultivation time treatments with two replications with four petri dishes per replication and 10 callus pieces per petri dish was used. For inoculation, the bacteria were resuspended in filter-sterilized Schenk and Hildebrandt medium containing 0.6 M mannitol and 20 mg/L acetosyringone at pH 5.6 for at least one hour before use. For inoculation, Type I callus pieces were placed in bacterial solution. For co-cultivation, the pieces were blotted, then transferred to MS co-cultivation medium described above. All plates were co-cultivated in the dark at 23° C. for either two or four days. After either two or four days of co-cultivation, all callus was stained for GUS expression.

The results showed that the frequencies of GUS expression did not vary with respect to co-cultivation time. Across all treatments, the frequencies of GUS expression ranged from 50–70%. The intensity of GUS staining ranged from dark to light blue. However, heavy bacterial overgrowth was present after four days of co-cultivation and this bacterial coating was found to inhibit GUS staining.

Example 38

A different gene construct was used to test the efficacy of the Type I callus co-cultivation protocol with another Agrobacterium strain, C58sZ707pBI121.

Type I callus was produced by growing *Lemna gibba* G3 fronds on solid Murashige and Skoog medium containing 3% sucrose, 0.15% Gelrite, 0.4% Difco Bacto-agar, 5 $\mu$M 2,4-D, and 2 $\mu$M BA. Callus induction and all subsequent culture was at 23° C. and under a 16 hr light/8 hr dark photoperiod with light intensity of approximately 40 μmol/m²·sec. After 4 weeks of callus induction, Type I callus clumps were separately cultured on the same medium with the 2,4-D concentration reduced to 1 μM. The callus was subcultured to fresh medium every two weeks until sufficient callus was proliferated for experimentation.

For co-cultivation, 400 ml of solid Murashige and Skoog medium (MS) with 3% sucrose, 0.15% Gelrite, 0.4% Difco Bacto-agar, 1 μM 2,4-D and 2 μM BA was prepared, the pH adjusted to 5.6, autoclaved at 121° C. for 20 minutes, and cooled. A filter-sterilized solution of acetosyringone was added to the cooled medium to a final concentration of 20 mg/L. The cooled medium was used to pour 16, 100 mm×15 mm petri dishes. Agrobacterium strain C58sZ707pBI121 was streaked on potato dextrose agar with 20 mg/L acetosyringone, 500 mg/L streptomycin sulfate, 50 mg/L spectinomycin, and 50 mg/L kanamycin sulfate and grown overnight at 28° C.

A randomized block experimental design with one bacterial strain treatment with four replications with four petri dishes per replication and 10 callus pieces per petri dish was used. For inoculation, the bacteria from one petri dish were resuspended in filter-sterilized Schenk and Hildebrandt medium containing 0.6 M mannitol and 20 mg/L of acetosyringone at pH 5.6 for at least one hour before use. For inoculation, Type I callus pieces were placed in bacterial solution for 8–10 minutes. For co-cultivation, the pieces were blotted and then transferred to MS co-cultivation medium described above. All callus was co-cultivated in the dark at 23° C. for two days. After co-cultivation, two callus pieces were selected from one plate per replication (8 pieces in total) and stained for GUS expression.

All callus pieces showed GUS expression ranging from dark to pale blue. The remaining callus was transferred from MS co-cultivation medium to identical MS medium that contained 500 mg/L of cefotaxime for the first two weeks and 500 mg/L, each, cefotaxime and carbenecillin, thereafter, to rid the tissue of the bacterial contaminant. All callus tissue was transferred to fresh MS medium containing cefotaxime and carbenecillin at two-week intervals. At each transfer, a subsample of callus pieces were stained for GUS expression. The frequencies of GUS expression decreased slightly but remained high with 70–95% of pieces showing some GUS expression. Visual inspection of callus on antibiotic medium showed no indication of bacterial contamination after 4 weeks of culture.

Example 39

Type II callus and Type III callus were tested for their ability to give GUS expression following co-cultivation in the presence of Agrobacterium strain AT656.

Both callus types were induced by culturing *Lemna gibba* G3 fronds on solid Murashige and Skoog medium containing 3% sucrose, 0.15% Gelrite, 0.4% Difco Bacto-agar, 30 μM 2,4-D and 0.02 μM BA at 23° C. under a 16 hr light/8 hr dark photoperiod with light intensity of approximately 40 μmol/m²·sec. After four weeks, Type II callus and Type III callus were separated from the original fronds and transferred to solid Murashige and Skoog medium containing 3% sucrose, 0.15% Gelrite, 0.4% Difco Bacto-agar, 10 μM 2,4-D, and 0.01 μM BA for callus maintenance under the same temperature and light conditions. The callus was subcultured to fresh medium every two weeks until sufficient callus was proliferated for experimentation.

Agrobacterium strain AT656 was streaked on potato dextrose agar containing 20 mg/L acetosyringone and 50 mg/L kanamycin sulfate and grown overnight at 28° C. For co-cultivation, 200 ml of Murashige and Skoog medium (MS) with 3% sucrose, 0.15% Gelrite and 0.4% Difco Bacto-agar, 10 μM 2,4-D and 0.02 μM BA was prepared, the pH adjusted to 5.6, autoclaved at 121° C. for 20 minutes, and cooled. A filter-sterilized solution of acetosyringone was added to the cooled medium to a final concentration of 20 mg/L. The cooled medium was used to pour 8, 100 mm×15 mm petri dishes.

A randomized block experimental design with two callus type treatments was used. Forty clumps of green callus, transferred evenly to 4 petri dishes, and 9 clumps of white callus, transferred evenly to 4 petri dishes, were inoculated. For inoculation, bacteria were resuspended in filter-sterilized Schenk and Hildebrandt medium containing 0.6 M mannitol and 20 mg/L acetosyringone at pH 5.6 for at least one hour before inoculation. For inoculation, pieces of green callus and white callus were dipped in the bacterial solution for 2–5 minutes. For co-cultivation, callus pieces were blotted then transferred as clumps to MS co-cultivation medium described above. All callus was incubated at 23° C. in the dark for two days.

After co-cultivation, all white callus and 3 pieces of green callus per plate were randomly picked and stained for GUS expression. Out of nine clumps of white callus, 7 clumps showed GUS expression of varying intensity. Out of 12 pieces of green callus, 6 showed GUS expression of varying intensity.

Example 40

Type I callus established from two different fast-growing strains of *Lemna gibba* (strain 6861 and 7784) and one strain of *Lemna minor* were co-cultivated with AT656 to determine the frequency of transformation with the protocol established using *Lemna gibba* G3.

Agrobacterium strain AT656 was streaked on potato dextrose agar containing 20 mg/L acetosyringone and 50 mg/L kanamycin sulfate and grown overnight at 28° C. For co-cultivation, 200 ml of Murashige and Skoog medium (MS) with 3% sucrose, 0.15% Gelrite and 0.4% Difco Bacto-agar, 10 μM 2,4-D and 0.02 μM BA was prepared, the pH adjusted to 5.6, autoclaved at 121° C. for 20 minutes, and cooled. A filter-sterilized solution of acetosyringone was added to the cooled medium to a final concentration of 20 mg/L. The cooled medium was used to pour 8, 100 mm×15 mm petri dishes.

For inoculation, bacteria were resuspended in filter-sterilized Schenk and Hildebrandt medium containing 0.6 M mannitol and 20 mg/L acetosyringone at pH 5.6 for at least one hour before inoculation. For inoculation, approximately 10–15 pieces of Type I callus from the 3 different duckweed strains and from *L. gibba* G3 (positive control) were dipped in the bacterial solution for 2–5 minutes. For co-cultivation, callus pieces were blotted, then transferred as clumps to two plates (for each duckweed strain) of co-cultivation medium, as described above. All callus was incubated at 23° C. in the dark for two days.

After co-cultivation, all callus pieces of the two *Lemna gibba* strains and 3 pieces of callus from the *Lemna minor* strain were randomly picked and stained for GUS expression. All callus pieces showed multiple small spots of GUS staining cells two weeks after co-cultivation, consistent with successful transformation.

Selection using Fronds

Example 41

*Lemna gibba* G3 fronds were used to test the effect of three co-cultivation media on rescue of fronds expressing GUS and growing on kanamycin selection medium.

Fronds were grown for 3 days on liquid Schenk and Hildebrandt medium containing 1% sucrose, and 10 μM indoleacetic acid prior to use. The bacterial strain, AT656, was grown overnight on potato dextrose agar containing 20 mg/L acetosyringone and 50 mg/L kanamycin sulfate at 28° C. Three solid media were used for co-cultivation: 1) Schenk and Hildebrandt medium (SH) containing 1% sucrose, 1% agar, 20 mg/L acetosyringone, and 10 μM indoleacetic acid, 2) Murashige and Skoog medium (MS) containing 3% sucrose, 1% agar, 20 mg/L acetosyringone, and 50 μM 2,4-dichlorophenoxyacetic acid (2,4-D), and 3) Murashige and Skoog medium containing 3% sucrose, 1% agar, 20 mg/L acetosyringone, 5 μM 2,4-D, 10 μM naphthaleneacetic acid, 10 μM giberrellic acid G3, and 2 μM benzyladenine. The media were prepared, the pH adjusted to 5.6 (SH) or 5.8 (both MS types), autoclaved, cooled, heat labile components acetosyringone, indoleacetic acid and giberrellic acid added as filter-sterilized solutions, and the medium poured into 100 mm×15 mm petri dishes. For each medium, 20 petri dishes (500 ml) were prepared.

A randomized block experimental design with three co-cultivation media treatments with 4 replication with 5 petri dishes per replication and 20 fronds per petri dish was used. For inoculation, the bacteria on one petri dish were resuspended as described in Example 21.

For inoculation, individual fronds were separated from clumps, each turned abaxial side up and wounded with a sterile scalpel in the meristematic regions. Fronds were transferred to bacterial suspensions and incubated for 10 minutes. For co-cultivation, fronds were transferred to the three co-cultivation media described above. All plates were incubated for 5.5 days in the dark at 23° C.

After 5.5 days of co-cultivation, the fronds from two petri dishes per medium were stained for GUS expression. The results showed that GUS expression was present to a large extent on fronds co-cultivated on Schenk and Hildebrandt medium, less staining was seen with fronds on Murashige and Skoog media. The remaining fronds from the other 18 plates of each medium (18 plates×3 media=54 plates) were transferred to both solid and liquid media of the same composition without acetosyringone, and with 500 mg/L of timentin. The fronds from 3 plates were transferred into 3 flasks with 25 ml of liquid media and were grown under 23° C. under a 16 hr light/8 hr dark photoperiod with light intensity of approximately 40 μmol/m$^2$·sec. The fronds on 15 plates of solid media were divided into 2 groups: 1) the fronds from 10 original plates were transferred to 12 new plates and incubated in the dark (12 plates), 2) the fronds from 5 original plates were transferred to 6 new plates and incubated under subdued light conditions of less than 5 μmol/m$^2$·sec.

After 11 days of growth, subsamples of fronds were taken to stain for GUS expression. The results showed that regardless of light treatment or medium treatment, GUS expression was still present. All fronds, regardless of media, incubated under subdued light showed the highest intensity of GUS expression. Fronds incubated in the dark showed an intermediate level of GUS expression and fronds incubated in the light showed very low levels. Fronds incubated on Shenk and Hildebrandt medium showed the highest frequencies of GUS positive tissue, however no GUS expression was associated with newly expanding fronds.

On Murashige and Skoog media formulated to induce callus, the staining pattern was restricted to single cells and very small regions. Fronds on MS medium containing 2,4-D, NAA, GA3 and BA showed more intense staining than those incubated on MS medium containing only 2,4-D. Callus formation on both MS based media, with plant growth regulators adjusted to induce callus, did not occur in the dark, but had started on MS medium with 2,4-D, NAA, GA3 and BA under subdued light. Based on these results, fronds on Schenk and Hildebrandt medium were dropped from the experiment. All remaining fronds on MS media in darkness were transferred to subdued light conditions to continue incubation. All tissue was kept on the same medium formation but transferred to fresh medium with timentin and incubation was continued under subdued light conditions for about 5 weeks.

Seven weeks after co-cultivation all remaining tissue was again transferred to fresh medium and kanamycin sulfate at either 10 mg/L (about 25% of the tissue) or 2 mg/L (about 75% of the remaining tissue) was included. One week later, a subsample of tissue from both kanamycin treatments was stained for GUS expression. Three types of staining was present: 1) staining associated with the original, co-cultivated fronds, 2) staining associated with Type I callus, and 3) staining associated with Type III callus. The frequency of callus staining was not high, estimated at about 5–8 fronds giving rise to a kanamycin resistant culture per hundred fronds co-cultivated. Incubation and subculturing of the tissue was continued for another 5 weeks under subdued light.

At twelve weeks, all tissue remaining was from cultures on MS medium containing 2,4-D, NAA, GA3 and BA. The tissue was transferred to Murashige and Skoog medium with 1 μM 2,4-D, 2 μM BA, 0.15 g/L Gelrite, 0.4 g/L Difco Bacto-agar, 500 mg/L timentin and 10 mg/L kanamycin sulfate. Heat labile components were filter-sterilized and added to autoclaved, cooled medium. Healthy tissue that had proliferated from each originally co-cultivated frond was transferred to an individual petri dish. All tissue was incubated at 23° C. and shifted from subdued to full light intensity of approximately 40 μmol/m$^2$·sec and a 16 hr light/8 hr dark photoperiod. At this time a small subsample of tissue was stained for GUS expression and the results showed a low frequency of GUS staining associated with Type III callus. After two weeks it became obvious from visual observation that transfer to full light had enhanced the segregation of kanamycin resistant callus from kanamycin sensitive tissue. Growth of callus on kanamycin was continued for another 4 weeks (to 16 weeks total) by transfer of all living tissue to fresh medium.

Between sixteen and twenty weeks after co-cultivation, kanamycin resistant callus lines became established. These compact Type I callus and Type III callus cultures were characterized by growth on 10 mg/L kanamycin in the light. Eight kanamycin resistant callus cultures were proliferated from 360 original co-cultivated fronds. As these eight lines developed, subsamples of the callus were transferred to half-strength Schenk and Hildebrandt medium containing 0.5% sucrose to regenerate fronds. Of these eight, three regenerated fronds in the absence of kanamycin, frond regeneration would not occur in the presence of kanamycin. None of these fronds showed GUS expression when stained.

Selection of Callus Cultures and Regeneration of Transformed Fronds

Example 42

Type I callus was tested for its ability to give GUS expression and kanamycin sulfate resistant cultures following co-cultivation in the presence of Agrobacterium strain C58sZ707pBI121.

Type I callus was produced by growing *Lemna gibba* G3 fronds on solid Murashige and Skoog medium containing 3% sucrose, 0.15% Gelrite, 0.4% Difco Bacto-agar, 5 μM 2,4-D, and 2 μM BA. Callus induction and all subsequent culture was at 23° C. and under a 16 hr light/8 hr dark photoperiod with light intensity of approximately 40 μmol/m$^2$·sec. After 4 weeks of callus induction, Type I callus clumps were separately cultured on the same medium with the 2,4-D concentration reduced to 1 μM. The callus was subcultured to fresh medium every two weeks until sufficient callus was proliferated for experimentation.

For co-cultivation, 400 ml of solid Murashige and Skoog medium (MS) with 3% sucrose, 0.15% Gelrite, 0.4% Difco Bacto-agar, 1 μM 2,4-D and 2 μM BA was prepared, the pH adjusted to 5.6, autoclaved at 121° C. for 20 minutes, and cooled. A filter-sterilized solution of acetosyringone was added to the cooled medium to a final concentration of 20 mg/L. The cooled medium was used to pour 20, 100 mm×15 mm petri dishes. Agrobacterium strain C58sZ707pBI121 was streaked on potato dextrose agar with 20 mg/L acetosyringone, 500 mg/L streptomycin, 50 mg/L spectinomycin, and 50 mg/L kanamycin sulfate and grown overnight at 28° C.

A randomized block experimental design with one bacterial strain treatment with one replication with 20 petri dishes per replication and approximately 10 callus pieces per petri dish was used. For inoculation, the bacteria were resuspended in filter-sterilized Schenk and Hildebrandt medium containing 0.6 M mannitol and 20 mg/L acetosyringone at pH 5.6 for at least one hour before use. For inoculation, Type I callus pieces were placed in bacterial solution. For co-cultivation, the pieces were blotted then transferred to MS co-cultivation medium described above. All callus pieces were co-cultivated for two days at 23° C. in the dark. After co-cultivation, a subsample of callus pieces were histochemically stained for GUS expression. The results showed a high frequency of GUS expression of varying intensity.

The approximately 200 remaining callus pieces were transferred to decontamination medium. For decontamination, 500 ml of solid MS medium containing 3% sucrose, 0.15% Gelrite, 0.4% Difco Bacto-agar, 1 μM 2,4-D, and 2 μM BA was prepared, the pH adjusted to 5.6, autoclaved for 20 minutes at 121° C., and cooled. A filter-sterilized solution containing cefotaxime was added to the cooled medium to a final medium concentration of 500 mg/L. The cooled medium was used to pour 20 plates. Approximately 10 callus pieces, each, were transferred to the 20 petri dishes of decontamination medium. All petri dishes were incubated at 23° C. in the dark. Weekly subcultures of the callus pieces to identical fresh medium were done and the callus was incubated under the same conditions. At week 5, a small subsample of callus tissue was stained for GUS expression. Expression was present at high frequency and at varying intensity.

On week 5, the remaining callus pieces were transferred to selection medium. For selection, 500 ml of MS with 3% sucrose, 0.15% Gelrite and 0.4% Difco Bacto-agar, supplemented with 1 μM 2,4-D and 2 μM BA was prepared, the pH adjusted to 5.6, autoclaved for 20 minutes at 121° C., and cooled. A filter-sterilized solution containing cefotaxime, carbenicillin, and kanamycin sulfate was added to the cooled medium to a final medium concentration of 500, 500 and 2 mg/L, respectively. The cooled medium was used to pour 20 plates. Approximately 9–10 callus pieces were transferred to the 20 petri dishes of selection medium. All callus was incubated at 23° C. under a 16 hr light/8 hr dark photoperiod of subdued light intensity of approximately 3–5 μmol/m$^2$·sec. After one week of incubation, the callus was transferred to the same medium except that the kanamycin concentration was increased to 10 mg/L. Callus culture was continued under the same incubation conditions for another week, subcultured once to fresh medium of identical composition. At the end of this two-week, kanamycin selection period, approximately 25% of the original callus pieces showed healthy callus growth with the remainder in decline.

On week seven, 64 of the healthiest callus pieces were transferred to solid MS medium with 3% sucrose, 0.15% Gelrite, 0.4% Difco Bacto-agar, 1 μM 2,4-D, 2 μM BA, 500 mg/L, each, carbenecillin and cefotaxime, and four different concentrations of kanamycin sulfate: 10, 20, 40, and 80 mg/L. 160 ml of the medium was prepared, the pH adjusted to 5.6, autoclaved, and cooled. Filter-sterilized solutions of the heat labile antibiotics were added to the appropriate concentrations. The cooled media were then used to pour 16, 60 mm×15 mm petri dishes. Approximately 4 callus pieces were transferred to each plate and 4 plates were prepared of each kanamycin concentration (16 callus pieces per kanamycin concentration). Incubation of the callus continued at 23° C. under subdued light. At weekly intervals, 4 plates, one from each of the kanamycin concentrations, were transferred to a higher light intensity of 40 μmol/m$^2$·sec. On week nine, regardless of light conditions, all callus was transferred to fresh medium of identical composition as the previous subculture. By week 12, all callus was under the higher light intensity of 40 μmol/m$^2$·sec. Callus culture was continued for another four weeks (to week 16), with subculture to fresh medium at two-week intervals.

On week 16, a small subsample of the remaining healthy callus was stained for GUS expression. All healthy callus pieces showed GUS expression with whole callus pieces showing uniform staining indicating segregation of GUS expressing callus from non-expressing callus. Most of the callus had died by this time, but greater than 10% showed varying degrees of healthy callus proliferation. Three callus lines, A, B, and C were identified and transferred to medium to promote frond regeneration. Upon further subculture of growing callus pieces on selection medium, 6 more callus lines, D–I, were identified and transferred to regeneration medium. Eight of the 9 lines were found on medium containing 10 mg/L kanamycin. The exception was line D which showed good growth on 40 mg/L kanamycin. Upon subsequent subculture, six callus lines continued to grow: A, B, D, F, H, and I.

Two of the nine identified lines went on to regenerate fronds that were positive for GUS expression when stained and that would proliferate readily in the presence or absence of kanamycin. For regeneration, water agar was prepared from 100 ml of distilled water with 0.4% Difco Bacto-agar and 0.15% Gelrite, the pH was adjusted to 5.6, and the medium autoclaved for 18 minutes at 121° C. This medium was used to pour 10, 60 mm×15 mm petri dishes. Small pieces of callus from lines A, D, F, H, and I were transferred to two petri dishes, each, of medium. The callus was incubated at 23° C. under a 16 hr light/8 hr dark photoperiod with light intensity of approximately 40 μmol/m$^2$·sec. Callus culture on water agar was continued for six weeks, with subculture to fresh water agar at two-week intervals. By week six, the callus from all lines had turned yellowish and brown. The callus was transferred at the end of week 6 to either solid or liquid, half-strength Schenk and Hildebrandt medium containing 0.5% sucrose and 0.8% Difco Bacto-agar (solid medium only). After 4–6 weeks the callus had organized green nodules that differentiated into thickened, frond like structures. As fronds could be detached from the callus clumps they were transferred to full-strength Schenk and Hildebrandt medium containing 1% sucrose, with incubation at 23° C. under a 16 hr light/8 hr dark photoperiod with light intensity of approximately 40 μmol/m$^2$·sec. These fronds proliferated in liquid SH medium indefinitely. The fronds proliferated equally well on SH medium with or without kanamycin. Bleaching of fronds was not seen in the presence of kanamycin. Frond subsamples were taken periodically and stained for GUS expression. All fronds showed GUS expression.

To confirm transformation, Southern hybridization analysis was done on DNA isolated from lines A and D. Duckweed DNA preparations were prepared from untransformed L. gibba G3 and from transformed lines A and D using the CTAB procedure of Doyle and Doyle (Amer. J. of Botany 75, 1238 (1988)). Isolated DNA was digested with restriction enzymes EcoR1 and Hind III, and with both enzymes, and fragments were electrophoretically separated on a 0.7% agarose gel. The gel was blotted to a nylon membrane following the methods of Sambrook. SAMBROOK ET AL., MOLECULAR CLONING: A LABORATORY MANUAL (1989). For probe, plasmid DNA from pBI121 was isolated using an alkali SDS procedure of Sambrook. Id. The 12.8 kb plasmid DNA was digested with restriction enzymes EcoR1 and Hind III to produce a 3.2 kb fragment consisting of the β-glucuronidase gene and an approximately 9 kb fragment containing the neomycin phosphotransferase gene. Both fragments were isolated from the agarose gel and radioactively labeled by random priming using the Prime-a-Gene kit (Promega). Using these probes, hybridization was done with blots carrying untransformed duckweed DNA and either DNA from transformed line A or transformed line D. The hybridization reaction was carried out at 65° C. overnight in a hybridization oven. The membrane was washed under stringent conditions of 0.1×SSC, 0.1% SDS. The blot was then placed in contact with BIOMAX MS film (Kodak), and the autoradiograph exposed for 2 days at −70° C.

The results of the hybridization experiments showed that GUS and NPTII hybridizing DNA was present in duckweed lines A and D, but not in DNA from untransformed duckweed (results for line D shown in FIG. 1). Double digestion of transformed duckweed DNA gave hybridization at the expected molecular weight. Single digestion showed that hybridization was associated with DNA fragments of unexpected molecular weight, indicating that the hybridizing DNA was not of bacterial origin and was integrated into plant DNA. Probing the same blots with labeled virulence region probe showed the absence of hybridization, indicating that the positive GUS and NPTII signals came from plant, not bacterial origin.

Example 43

Type I callus was tested for its ability to give GUS expression and kanamycin sulfate resistant cultures following co-cultivation in the presence of Agrobacterium strain C58sZ707pBI121.

Type I callus was produced by growing Lemna gibba G3 fronds on solid Murashige and Skoog medium containing 3% sucrose, 0.15% Gelrite, 0.4% Difco Bacto-agar, 5 μM 2,4-D, and 2 μM BA. Callus induction and all subsequent culture was at 23° C. under a 16 hr light/8 hr dark photoperiod with light intensity of approximately 40 μmol/m$^2$·sec. After 4 weeks of callus induction, Type I callus clumps were separately cultured on the same medium with the 2,4-D concentration reduced to 1 μM. The callus was subcultured to fresh medium every two weeks until sufficient callus was proliferated for experimentation.

For co-cultivation, 750 ml of solid Murashige and Skoog medium (MS) with 3% sucrose, 0.15% Gelrite, 0.4% Difco Bacto-agar, 1 μM 2,4-D and 2 μM BA was prepared, the pH adjusted to 5.6, autoclaved at 121° C. for 20 minutes, and cooled. A filter-sterilized solution of acetosyringone was added to the cooled medium to a final concentration of 20 mg/L. The cooled medium was used to pour 30, 100 mm×15 mm petri dishes. Agrobacterium strain C58sZ707pBI121 was streaked on potato dextrose agar with 20 mg/L acetosyringone, 500 mg/L streptomycin, 50 mg/L spectinomycin, and 50 mg/L kanamycin sulfate and grown overnight at 28° C.

A randomized block experimental design with one bacterial strain treatment with one replication with 30 petri dishes per replication and approximately 5 callus pieces per petri dish was used. For inoculation, the bacteria were resuspended in filter-sterilized MS medium containing 0.6 M mannitol and 20 mg/L acetosyringone at pH 5.8 for at least one hour before use. For inoculation, Type I callus pieces were placed in bacterial solution. For co-cultivation, the pieces were blotted then transferred to MS co-cultivation medium described above. All callus pieces were co-cultivated for two days at 23° C. in the dark. After co-cultivation, a subsample of callus pieces were histochemically stained for GUS expression. The results showed a high frequency of GUS expression.

The approximately 150 remaining callus pieces were transferred to decontamination medium. For decontamination, 750 ml of solid MS medium containing 3% sucrose, 0.15% Gelrite, 0.4% Difco Bacto-agar, 1 μM 2,4-D, and 2 μM BA was prepared, the pH adjusted to 5.8, autoclaved for 20 minutes at 121° C., and cooled. A filter-sterilized solution containing cefotaxime and carbenicillin was added to the cooled medium to a final medium concentrations of 500 mg/L, each. The cooled medium was used to pour 30 plates. Approximately 5 callus pieces were transferred to each of the 30 petri dishes of decontamination medium. The callus was then incubated at 23° C. in the dark. Weekly subcultures of the callus pieces to identical fresh medium were done and the callus was incubated under the same conditions.

Selection for kanamycin resistant callus lines was begun on week 5. For selection, 750 ml of solid MS medium containing 3% sucrose, 0.15% Gelrite, 0.4% Difco Bacto-agar, 1 μM 2,4-D, and 2 μM BA was prepared, the pH adjusted to 5.8, autoclaved for 20 minutes at 121° C., and cooled. A filter-sterilized solution containing cefotaxime, carbenicillin, and kanamycin was added to a final medium concentration of 500 mg/L, 500 mg/L, and 2 mg/L, respectively. The cooled medium was used to pour 30 plates. Approximately 5 callus pieces were transferred to each of the 30 petri dishes of selection medium. The callus was then incubated at 23° C. in the dark.

For weeks 6 and 7, the callus was transferred to identical fresh medium with the kanamycin concentration increased to 10 mg/L. Incubation was continued in the dark at 23° C. At the beginning of week 8 the kanamycin concentration was increased. Murashige and Skoog medium with composition identical to that of previous subcultures was prepared with half the medium containing kanamycin at 10 mg/L and the other half with kanamycin at 40 mg/L. Approximately half of the remaining callus was transferred to each kanamycin concentration. The light conditions of incubation were changed as well. All callus was incubated at 23° C.

under a 16 hr light/8 hr dark photoperiod with light intensity of approximately 3–5 $\mu$mol/m$^2$·sec. The callus was maintained under these medium and incubation conditions for two weeks. After two weeks at the subdued light level, the callus was transferred to fresh medium of identical composition containing kanamycin at either 10 or 40 mg/L, and the light intensity was increased to 40 $\mu$mol/m$^2$·sec. The callus was maintained on a two-week subculture regime on identical medium and incubation conditions.

By week 12, approximately 10% of the callus remained healthy and growing. Of the 15 proliferating callus lines remaining, half were growing on 10 mg/L kanamycin and the remainder on 40 mg/L. Histochemical staining of small subsamples of callus from 6 lines showed GUS expression in sectors of the callus pieces.

Fronds were regenerated following the procedure of Example 42. Frond proliferation was normal when grown in the presence or absence of kanamycin sulfate, and no bleaching of the fronds was observed. Fronds also showed intense GUS histochemical staining. Southern hybridization analysis showed the presence of DNA sequences of the expected fragment size for both the GUS and neomycin phosphotransferase genes, and the absence of DNA sequences from the vir region. Appropriate restriction enzyme analysis was carried out as in Example 42, and the results were consistent with a finding of integration of foreign genes into the plant genome.

Example 44

Based on the previous Examples, the following method is preferred for transforming duckweed callus with Agrobacterium, followed by selection and regeneration of transformed plants. Overall, *Lemna minor* has a particularly vigorous callus system, which makes it easier to regenerate transformed plants from this species.

Typically, callus transformation, selection, and frond regeneration is dependent upon a well-established callus system and a number of parameters optimized for each step of the process. A vigorously growing callus culture is maintained as described in Example 16. Agrobacteria are grown (on Potato Dextrose Agar with appropriate antibiotics and 100 $\mu$M acetosyringone) and resuspended as in Example 32, except that the preferred resuspension medium is MS rather than SH. Callus pieces are inoculated by immersing in the solution of resuspended bacteria for a minimum of 3–5 minutes, blotted to remove excess fluid, and plated on co-cultivation medium consisting of MS supplemented with auxin and cytokinin optimized to promote callus growth and 100 $\mu$M acetosyringone. Inoculated callus is incubated in darkness for 2 days.

After co-cultivation, callus is transferred to fresh media containing antibiotics to decontaminate the cultures from infecting Agrobacteria. The preferred medium is MS with 3% sucrose, 1 $\mu$M 2,4-D, 2 $\mu$M BA, gelled with 0.15% Gelrite and 0.4% Difco Bacto-agar and antibiotic(s). The callus is incubated under subdued light of 3–5 $\mu$mol/m$^2$·sec. The callus is transferred every 2–5 days, 3 days is preferred, to fresh medium of the same composition. The total recovery period lasts for 2–3 weeks, 3–6 subcultures.

Callus selection follows after the recovery period. Callus is transferred to MS medium supplemented with 1 $\mu$M 2,4-D, 2 $\mu$M BA, 3% sucrose, 0.4% Difco Bacto-agar, 0.15% Gelrite, and 10 mg/L kanamycin sulfate. The callus is incubated under subdued light of 3–5 $\mu$mol/m$^2$·sec, with transfer to fresh medium of the same composition every 2 weeks. The callus is maintained in this way for 4–6 weeks.

Then the callus is incubated under full light of 40 $\mu$mol/m$^2$·sec on the same medium. Selection is considered complete when the callus shows vigorous growth on the selection agent.

Callus showing vigorous growth on callus maintenance medium in the presence of the selection agent is transferred to regeneration medium to organize and produce plants. In general, duckweed regenerates on lean media. For *L. minor* it is half-strength SH medium with 1% sucrose; for *L. gibba* it is water agar. Typically, the selection agent is not present in the regeneration medium. The callus is incubated, under full light, on regeneration medium for 2–4 weeks until fronds appear. Fully organized fronds are transferred to liquid SH medium with 1–3% sucrose and no plant growth regulators and incubated under full light for further clonal proliferation.

Example 45

The effect of light intensity and kanamycin sulfate concentration were tested for its effect on the frequency of transformation of *Lemna minor* callus cultures.

*Lemna minor* fronds were grown in liquid Schenk and Hildebrandt medium containing 1% sucrose for two weeks at 23° C. under a 16 hr light/8 hr dark photoperiod with light intensity of approximately 40 $\mu$mol/m$^2$·sec prior to callus induction. Callus induction was accomplished as in Example 14 using fronds from *Lemna minor* strain 8744. Callus was maintained on MS medium containing 3% sucrose, 1 $\mu$M 2,4-D, 2 $\mu$M BA, 0.4% Bacto-agar and 0.15% Gelrite for 13 weeks prior to co-cultivation. Callus was subcultured to fresh medium every 2 weeks during this 13-week period.

Agrobacterium strain C58sz707 harboring the T-DNA containing binary plasmid from strain AT656, as described in Example 21, was grown on PDA containing 50 mg/L kanamycin sulfate, 50 mg/L spectinomycin, and 500 mg/L streptomycin for 2 days at 28° C. For co-cultivation, solid MS medium with 3% sucrose, 1 $\mu$M 2,4-D, 2 $\mu$M BA, 0.4% Bacto-Agar, and 0.15% Gelrite was prepared, the pH was adjusted to 5.6, the medium was autoclaved at 121° C. for 20 minutes, and cooled. A filter-sterilized solution of acetosyringone was added to the cooled medium to a final concentration of 100 $\mu$M. The cooled medium was used to pour 8, 100 mm×15 mm petri dishes.

For inoculation, the Agrobacteria were resuspended in filter-sterilized, MS medium containing 0.6 M mannitol and 100 $\mu$M acetosyringone at pH 5.6 for at least one hour before inoculation. For inoculation, approximately 160 pieces of Type I callus were dipped in the bacterial solution for 2–5 minutes in batches of 20 callus pieces. For co-cultivation, callus pieces were blotted, then transferred as clumps to co-cultivation medium, 20 callus clumps per 100 mm×15 mm petri dish. All inoculated callus was incubated at 23° C. in the dark for 2 days.

For selection, 200 ml of MS medium containing 1 $\mu$M 2,4-D, 1 $\mu$M BA, 3% sucrose, 500 mg/L carbenicillin, 500 mg/L cefotaxime, 10 mg/L kanamycin sulfate, 0.4% Bacto-Agar and 0.15% Gelrite was prepared, the pH was adjusted to 5.6, the medium was autoclaved at 121° C. for 20 minutes and 8, 100 mm×15 mm petri dishes were poured. The antibiotics were added to cooled, autoclaved medium as a filter-sterilized solution just prior to pouring. Co-cultivated callus clumps were transferred to the fresh selection medium, 20 callus clumps per petri dish. Eighty callus clumps (4 plates) were incubated under subdued light of less than 5 $\mu$mol/m$^2$·sec and the other 80 callus clumps (4 plates) were transferred to a higher light intensity of 40 $\mu$mol/ m²·sec. For 3 weeks, callus was subcultured to fresh, antibiotic-containing medium every week. On week 4, half (40 callus clumps) of the callus from each light treatment was transferred to fresh medium in which the kanamycin concentration was increased from 10 mg/L to 40 mg/L. The remaining 40 callus clumps were transferred to fresh medium maintaining the original kanamycin concentration of 10 mg/L. Incubation under identical subdued or full light conditions and low or high kanamycin concentrations was continued for 2 more weeks, with weekly subcultures. At 6 weeks post-inoculation, all samples were transferred to fresh medium and incubated under full light intensity. From this point onward, subculture was at 2-week intervals.

After 12 weeks of culture on kanamycin, vigorously growing callus was transferred to fresh, regeneration medium. Frond regeneration medium consisted of half-strength Schenk and Hildebrandt medium containing 1% sucrose, 0.4% Bacto-agar, and 0.15% Gelrite. Callus clumps were transferred to fresh medium of the same composition every 2 weeks. Fronds regenerated from callus clumps 3–6 weeks after transfer to regeneration medium.

Two transformed, clonal frond lines were regenerated from this experiment. Both lines showed GUS histochemical staining, had different levels of GUS enzyme activity (0.31% and 0.14% of extractable protein) as measured in a soluble assay using methylumbelliferone-glucuronic acid (MUG) as the substrate, and had detectable levels of neomycin phosphotransferase enzyme as measured using and ELISA assay. Southern hybridization analysis confirmed the presence of foreign DNA sequences in high molecular weight DNA, which when digested with the appropriate restriction enzymes gave the expected fragment sizes. Re-probing of the stripped blot with DNA sequences representing the virulence region of the original Agrobacterium failed to give detectable hybridization.

Example 46

The effect of *Lemna minor* genotype of the frequency of rescue of transformed fronds was tested using *Lemna minor* callus cultures from strain 8627.

Callus maintenance prior to inoculation, bacterial strain, bacterial growth for inoculation, bacterial resuspension, callus inoculation procedure, and co-cultivation for 2 days in darkness were performed as in Example 45.

For kanamycin selection, following co-cultivation, 180 callus clumps were transferred to MS medium containing 1 $\mu$M 2,4-D, 2 $\mu$M BA, 500 mg/L carbenicillin, 500 mg/L cefotaxime and 10 mg/L kanamycin sulfate. All callus was incubated under subdued light levels of less than 5 $\mu$mol/ m²·sec. On the second week after inoculation, half the callus pieces were transferred to fresh selection medium in which the kanamycin sulfate concentration was increased from 10 mg/L to 40 mg/L, the rest were transferred to fresh selection medium containing 10 mg/L of kanamycin sulfate. Weekly subculture was continued through week 5, post-inoculation at which time subcultures were done every two weeks.

To regenerate transformed fronds, callus lines growing vigorously on kanamycin and showing GUS expression using histochemical staining after 12 weeks were transferred to frond regeneration medium containing half-strength Schenk and Hildebrandt medium with 1% sucrose, 0.4% Bacto-agar and 0.15% Gelrite. Fronds regenerated after 3–4 weeks on regeneration medium. Regenerated fronds were maintained on SH medium with 1% sucrose.

Three transformed, clonal frond lines were regenerated in this experiment. All 3 lines showed GUS histochemical staining, variable levels of GUS activity as measured by the MUG assay (0.2–0.3% of extractable protein), and detectable levels of neomycin phosphotransferase protein as measured in an ELISA assay. Southern hybridization was used to confirm transformation and integration of foreign DNA sequences into duckweed DNA.

Example 47

The effect of medium composition on frond regeneration from *L. minor* callus cultures was also tested. Seven media formulations were tested: (1) water agar, (2) water agar with 100 $\mu$M adenine sulfate, (3) water agar with 10 $\mu$M BA, (4) water agar with 10 $\mu$M BA and 1 $\mu$M IBA, (5) half-strength SH, (6) half-strength SH with 10 $\mu$M BA, and (7) half-strength SH with 10 $\mu$M BA and 1 $\mu$M IBA. Callus cultures from both strain 8744 and strain 8627 proliferated in a previous callus induction medium as in Example 12 were used for this experiment. Callus was incubated on the seven different media for 8 weeks, with continual observation for the development of fronds.

Frond regeneration was only achieved on the half-strength SH treatments. When half-strength SH was supplemented with 10 $\mu$M BA only, callus growth was faster than that plated on half-strength SH without plant growth regulators, however, regeneration took longer than on half-strength SH. The addition of IBA to the medium had no effect on the timing or ability of callus to regenerate fronds.

Example 48

The efficiency of the duckweed system for mammalian gene expression was tested using a human β-hemoglobin gene construct and a P450 oxidase construct.

Two Agrobacterium strains were used to inoculate Type I callus of *Lemna minor* strain 8627. For β-hemoglobin transformations, strain C58 C1, harboring 3 plasmids: pGV3850, pTVK291, pSLD34 was used. pTVK291 contains the supervirulence G gene from pTiBo542. pSLD34 is an Agrobacterium binary plasmid, derived from pBIN19, consisting of a neomycin phosphotransferase gene under the control of CaMV35S promoter, and a human β-hemoglobin gene driven by the super-mac promoter.

For P450 oxidase transformations, strain C58 C1, harboring 3 plasmids: pGV3850, pTVK291 and pSLD35 were used. The T-DNA is carried on the binary plasmid, pSLD35, which is similar in structure to pSLD34, with the exception that pS:D35 does not contain the β-hemoglobin gene and instead contains DNA sequences encoding 3 proteins: a human P450 oxidase, an oxidoreductase, and a cytochrome B5. Each gene is driven by a super-mac promoter. The pSLD35 plasmid contains both hygromycin and kanamycin selectable marker genes.

Several experiments with the basic experimental design of 2 bacterial strains×2 light intensities during early selection×2 kanamycin concentrations during selection experimental design (8 treatments in total) with 3 replications, with 2 petri dishes per replications and 10 callus pieces per petri dish was used. Callus cultures produced from *Lemna minor* strains 8627 and 8744 and *Lemna gibba* strain G3 were used in these experiments. Callus maintenance prior to inoculation, bacterial strain, bacterial growth for inoculation, bacterial resuspension, callus inoculation procedure, and co-cultivation for 2 days in darkness were performed as in Example 45, with the exception that bacteria were grown on PDA containing 50 mg/L kanamycin, 50 mg/L gentamycin, 100 mg/L carbenicillin, and 100 $\mu$M acetosyringone prior to inoculation.

For kanamycin selection, following co-cultivation, callus clumps were transferred to MS medium containing 1 µM 2,4-D, 2 µM BA, 500 mg/L carbenicillin, 500 mg/L cefotaxime and two concentrations of kanamycin: 10 mg/L and 40 mg/L. The callus cultures were further divided during incubation with half of the callus pieces on each kanamycin concentration going to subdued light and the other half being incubated under full light. Callus was subcultured to fresh medium of the same composition at weekly intervals for the first four weeks after co-cultivation. At week 5, all cultures were incubated under full light intensity for another 6 weeks, with subculture to fresh medium every two weeks.

Frond regeneration was accomplished using the appropriate media for frond regeneration from *L. gibba* G3 or *L. minor* strains as described in Example 42 and Example 47. Fronds regenerated after 3–4 weeks on regeneration medium. Regenerated fronds were maintained on SH medium with 1% sucrose.

Across all experiments, more than 20 transformed clonal frond lines were rescued. More lines were found using 10 mg/L kanamycin as the selection concentration, as opposed to 40 mg/L. Subdued light intensity during selection proved advantageous. All lines showed vigorous callus growth on kanamycin, had detectable and variable levels of neomycin phosphotransferase protein as measured by an ELISA test. The presence of the P450 oxidase and β-hemoglobin DNA, RNA and/or protein is detected in stably transformed duckweed plants by any method known in the art, e.g., Southern, Northern and Western hybridizations, respectively.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A method for stably transforming duckweed tissue with a nucleotide sequence of interest, the method comprising the steps of:
   (a) inoculating a duckweed plant tissue with Agrobacterium comprising a vector which comprises a nucleotide sequence of interest; and
   (b) co-cultivating the tissue with the Agrobacterium to produce stably transformed tissue.

2. The method according to claim 1, further comprising the step of culturing the transformed tissue in a medium comprising an antibiotic sufficient to inhibit the growth of Agrobacterium.

3. The method according to claim 1, further comprising the step of culturing the transformed tissue in a medium comprising the selection agent.

4. The method according to claim 3, further comprising the step of regenerating stably transformed duckweed plants from the stably transformed tissue.

5. The method according to claim 1, wherein the tissue is callus tissue.

6. The method according to claim 1, wherein the tissue is meristematic tissue.

7. The method according to claim 1, wherein the tissue is frond tissue.

8. The method according to claim 1, wherein the duckweed tissue is selected from the group consisting of the genus Spirodela, genus Wolffia, genus Wolfiella, and genus Lemna.

9. The method according to claim 1, wherein the duckweed tissue is selected from the group consisting of *Lemna minor, Lemna miniscula,* and *Lemna gibba.*

10. The method according to claim 1, wherein the Agrobacterium is *Agrobacterium tumefaciens.*

11. The method according to claim 1, wherein the Agrobacterium is *Agrobacterium rhizogenes.*

12. The method according to claim 1, wherein the vector is a super-binary vector.

13. The method according to claim 1, wherein the vector is a C58-derived vector.

14. The method according to claim 1, wherein the gene which confers resistance to a selection agent is selected from the group consisting of neo, bar, pat, ALS, HPH, HYG, EPSP and Hm1.

15. The method according to claim 1, wherein the nucleotide sequence comprises two genes of interest.

16. The method according to claim 1, wherein the nucleotide sequence encodes a protein or peptide selected from the group consisting of insulin, growth hormone, α-interferon, β-glucocerebrosidase, retinoblastoma protein, p53 protein, angiostatin, leptin, and serum albumin.

17. The method according to claim 1, wherein the nucleotide sequence encodes at least one protein or peptide subunit of a multimeric protein selected from the group consisting of hemoglobin, collagen, P450 oxidase, and a monoclonal antibody.

18. A stably transformed duckweed tissue culture produced according to the method of claim 3.

19. A stably transformed duckweed plant produced according to the method of claim 4.

20. A stably transformed duckweed plant comprising a heterologous nucleic acid of interest incorporated in its genome wherein said plant is produced via an Agrobacterium-mediated method.

21. The stably transformed duckweed plant according to claim 20, wherein said heterologous nucleic acid of interest is flanked by T-DNA border sequences incorporated in its genome.

22. The stably transformed duckweed plant according to claim 21, wherein said duckweed plant comprises fewer than 5 copies of said heterologous nucleic acid of interest.

23. The stably transformed duckweed plant according to claim 20 or claim 21, wherein said duckweed plant is selected from the group consisting of the genus Spirodela, genus Wolffia, genus Wolfiella, and genus Lemna.

24. The stably transformed duckweed plant according to claim 21, wherein said duckweed plant is selected from the group consisting of *Lemna minor, Lemna miniscula,* and *Lemna gibba.*

25. The stably transformed duckweed plant according to claim 21, wherein said heterologous nucleic acid comprises at least one expression cassette comprising a gene which confers resistance to a selection agent.

26. The stably transformed duckweed plant according to claim 25, wherein said gene which confers resistance to a selection agent is of neo, bar, pat, ALS, HPH, HYG, EPSP and Hml.

27. The stably transformed duckweed plant according to claim 21, wherein said heterologous nucleic acid comprises two genes of interest.

28. The stably transformed duckweed plant according to claim 21, wherein said heterologous nucleic acid encodes a protein or peptide selected from the group consisting of insulin, growth hormone, α-interferon, β-glucocerebrosidase, retinoblastoma protein, p53 protein, angiostatin, leptin, and serum albumin.

29. The stably transformed duckweed plant according to claim 21, wherein said heterologous nucleic acid encodes at least one protein or peptide subunit of a multimeric protein selected from the group consisting of hemoglobin, collagen, P450 oxidase, and a monoclonal antibody.

30. A method of producing recombinant proteins or peptides, comprising the steps of
   (a) culturing a stably transformed duckweed plant that expresses at least one heterologous protein or peptide; and
   (b) collecting the at least one heterologous protein or peptide from the duckweed cultures.

31. The method according to claim 30, wherein the stably transformed duckweed plant is grown on wastewater.

32. The method according to claim 30, wherein the stably transformed duckweed plant expresses and assembles all of the subunits of a multimeric protein.

33. The method according to claim 32, wherein the multimeric protein is selected from the group consisting of collagen, hemoglobin, P450 oxidase, and a monoclonal antibody.

34. The method according to claim 30, wherein the stably transformed duckweed plant is grown in a bioreactor vessel.

35. The method according to claim 30, wherein one recombinant protein or peptide is produced.

36. The method according to claim 30, wherein the at least one heterologous protein or peptide is a therapeutic protein or peptide.

37. The method according to claim 30, wherein the at least one protein or peptide is selected from the group consisting of insulin, growth hormone, α-interferon, β-glucocerebrosidase, retinoblastoma protein, p53 protein, angiostatin, leptin, and serum albumin.

38. The method according to claim 30, wherein the at least one heterologous protein or peptide is an enzyme.

39. The method according to claim 30, wherein the at least one heterologous protein or peptide is secreted from the stably transformed duckweed plant.

40. The stably transformed duckweed plant according to claim 30, wherein said duckweed plant is selected from the group consisting of the genus Spirodela, genus Wolffia, genus Wolfiella, and genus Lemna.

41. The stably transformed duckweed plant according to claim 30, wherein said duckweed plant is selected from the group consisting of *Lemna minor, Lemna miniscula,* and *Lemna gibba.*

42. The method according to claim 1, wherein the vector is not a super-binary vector.

43. The method according to claim 1, wherein the Agrobacterium comprises an inducible vir gene.

44. The method according to claim 1, wherein the vector comprises a Cauliflower Mosaic virus 35S promoter.

45. The method according to claim 1, wherein the vector is a pBIN19 derivative.

46. The method according to claim 5, wherein said co-cultivating step is carried out for a time of about 1 to about 3 days.

47. The method according to claim 1, wherein the vector comprises a mas promoter.

48. A method for stably transforming duckweed tissue from the genus Lemna with a nucleotide sequence of interest, the method comprising the steps of:
   (a) inoculating a duckweed plant tissue with Agrobacterium comprising a vector which comprises a nucleotide sequence of interest, wherein the duckweed plant tissue is from the genus Lemna; and
   (b) co-cultivating the tissue with the Agrobacterium to produce stably transformed tissue.

49. The method according to claim 48, further comprising the step of regenerating stably transformed duckweed plants from the transformed tissue.

50. The method according to claim 48, wherein the duckweed plant tissue is from a species of *Lemna minor.*

51. The method according to claim 48, wherein the tissue is a callus tissue.

52. The method according to claim 51, wherein said co-cultivating step is carried out for a time of about 1 to about 3 days.

53. The method according to claim 48, wherein the vector is not a super-binary vector.

54. The method according to claim 48, wherein the Agrobacterium comprises an inducible vir gene.

55. The method according to claim 48, wherein the vector comprises a Cauliflower Mosaic virus 35S promoter.

56. The method according to claim 48, wherein the vector is a pBIN19 derivative.

57. The method according to claim 48, wherein the vector comprises a mas promoter.

58. A stably transformed duckweed plant produced according to the method of claim 48.

59. A stably transformed duckweed plant from the genus Lemna comprising a heterologous nucleic acid sequence incorporated in its genome wherein said plant is produced via an Agrobacterium-mediated method.

60. The stably transformed duckweed plant according to claim 59, wherein said heterologous nucleic acid sequence is flanked by T-DNA border sequences incorporated in its genome.

61. The stably transformed duckweed plant of claim 58, wherein said stably transformed duckweed plant is from a species of *Lemna minor.*

62. A method of producing recombinant proteins or peptides, comprising:
   (a) culturing a stably transformed duckweed plant from the genus Lemna that expresses at least one heterologous protein or peptide; and
   (b) collecting the at least one protein or peptide from the duckweed cultures.

63. The method of claim 62, wherein said stably transformed duckweed plant is a species of *Lemna minor.*

64. The method of claim 1, wherein said nucleotide sequence of interest is a gene which confers resistance to a selection agent.

65. The method of claim 1, wherein said nucleotide sequence of interest is a gene which confers resistance to a selection agent.

* * * * *

UNITED STATES PATENT AND TRADEMARK OFFICE
CERTIFICATE OF CORRECTION

PATENT NO. : 6,040,498
DATED : March 21, 2000
INVENTOR(S) : Stomp et al.

It is certified that error appears in the above-identified patent and that said Letters Patent is hereby corrected as shown below:

Title page,
Item [56], References Cited, U.S. PATENT DOCUMENTS,

Please insert:

| | | | |
|---|---|---|---|
| -- 4, 459, 355 | 7/1984 | Cello et al. | 435/469 |
| 4, 536, 475 | 8/1985 | Anderson | 435/469 |
| 4, 588, 693 | 5/1986 | Strobel | 435/469 |
| 4, 658, 082 | 4/1987 | Simpson et al. | 800/294 |
| 4, 762, 785 | 8/1988 | Comai | 435/469 |
| 4, 940, 838 | 7/1990 | Schilperoort et al. | 800/294 |
| 4, 954, 442 | 9/1990 | Gelvin et al. | 435/469 |
| 5, 164, 310 | 11/1992 | Smith et al. | 435/469 |
| 5, 187, 073 | 2/1993 | Goldman et al. | 435/469 |
| 5, 272, 072 | 12/1993 | Kaneko et al. | 435/468 |
| 5, 464, 763 | 11/1995 | Schilperoort et al. | 435/469 |
| 5, 569, 597 | 10/1996 | Grimsley et al. | 435/469 |
| 5, 612, 487 | 3/1997 | Lam et al. | 800/278 |
| 5, 635, 381 | 6/1997 | Hooykaas et al. | 435/440 |
| 5, 639, 947 | 6/1997 | Hiatt et al. | 800/278 |
| 5, 650, 307 | 7/1997 | Sijmons et al. | 435/468 |
| 5, 677, 474 | 10/1997 | Rogers | 800/278 |
| 5, 679, 558 | 10/1997 | Göbel et al. | 435/4698 |
| 5, 693, 512 | 12/1997 | Finer et al. | 435/173.5 |
| 5, 874, 265 | 2/1999 | Adams et al. | 435/470 |
| 5, 886, 244 | 3/1999 | Tomes et al. | 800/293 |
| 5, 888, 789 | 3/1999 | Rodriguez | 435/468 |
| 5, 914, 123 | 6/1999 | Arntzen et al. | 424/439 |

UNITED STATES PATENT AND TRADEMARK OFFICE
CERTIFICATE OF CORRECTION

PATENT NO. : 6,040,498
DATED : March 21, 2000
INVENTOR(S) : Stomp et al.

It is certified that error appears in the above-identified patent and that said Letters Patent is hereby corrected as shown below:

Item [56], References Cited, FOREIGN PATENT DOCUMENTS,

Please insert:

WO 97/17429   5/1997   WIPO . . . . . . . . . . . C12N  5/04

Column 61, claim 3,
Line 56, "claim 1" should read -- claim 64 --.

Column 62, claim 14,
Line 16, "claim 1" should read -- claim 64 --.

Column 62, claim 26,
Line 61, "selection agent is of" should read -- selection agent is selected from the group consisting of --.

Column 64, claim 58,
Line 33, "claim 48" should read -- claim 49 --.

Column 64, claim 65,
Line 57, "claim 1" should read -- claim 48 --.

Signed and Sealed this

Twelfth Day of February, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

| | | |
|---|---|---|
| PATENT NO. | : 6,040,498 | Page 1 of 1 |
| APPLICATION NO. | : 09/132536 | |
| DATED | : March 21, 2000 | |
| INVENTOR(S) | : Stomp et al. | |

It is certified that error appears in the above-identified patent and that said Letters Patent is hereby corrected as shown below:

<u>In the Claims</u>:

Column 63, line 43 should read -- The method according to --.

Column 63, line 47 should read -- The method according to --.

Signed and Sealed this

Twentieth Day of February, 2007

JON W. DUDAS
*Director of the United States Patent and Trademark Office*